(12) United States Patent
Johnson et al.

(10) Patent No.: US 11,612,506 B2
(45) Date of Patent: Mar. 28, 2023

(54) UNLOADING KNEE-ANKLE-FOOT ORTHOTIC APPARATUS WITH CONFORMING AND DISTRACTING HINGE

(71) Applicant: Icarus Medical, LLC, Charlottesville, VA (US)

(72) Inventors: David T. Johnson, Charlottesville, VA (US); Evan Eckersley, Charlottesville, VA (US); Benjamin Scire, Hopkinton, MA (US); Philip Miller, Charlottesville, VA (US); Nicholas Yantiss, Charlottesville, VA (US)

(73) Assignee: Icarus Medical, LLC, Charlottesville, VA (US)

( * ) Notice: Subject to any disclaimer, the term of this patent is extended or adjusted under 35 U.S.C. 154(b) by 0 days.

(21) Appl. No.: 17/902,683

(22) Filed: Sep. 2, 2022

(65) Prior Publication Data

US 2022/0401245 A1 Dec. 22, 2022

Related U.S. Application Data

(60) Continuation of application No. 17/700,479, filed on Mar. 21, 2022, now Pat. No. 11,458,034, which is a
(Continued)

(51) Int. Cl.
*A61F 5/01* (2006.01)

(52) U.S. Cl.
CPC .... *A61F 5/0125* (2013.01); *A61F 2005/0139* (2013.01); *A61F 2005/0165* (2013.01)

(58) Field of Classification Search
CPC ............ A61F 5/0125; A61F 2005/0139; A61F 2005/0165; A61F 13/048; A61F 13/107;
(Continued)

(56) References Cited

U.S. PATENT DOCUMENTS

| 4,520,804 A | 6/1985 | DiGeorge |
| 5,458,565 A | 10/1995 | Tillinghast, III et al. |

(Continued)

FOREIGN PATENT DOCUMENTS

| EP | 3352711 A1 | 8/2018 |
| JP | 6595965 B2 | 10/2019 |

(Continued)

OTHER PUBLICATIONS

DonJoy, "Knee Osteoarthritis Relief—Arthritis Knee Braces", (https://www.youtube.com/watch?v=1fPC3YPfmOY; Uploaded on Oct. 26, 2011).

(Continued)

*Primary Examiner* — Tarla R Patel
(74) *Attorney, Agent, or Firm* — Woods Rogers Vandeventer Black PLC; Nathan A. Evans

(57) ABSTRACT

An adjustable knee ankle foot orthosis for unloading weight from a knee joint afflicted with osteoarthritis, thus reducing pain and improving mobility, comprising: an upper and lower frame connected by an unloading hinge assembly, optionally comprising a sensor and processor allowing for remote or automatic control of brace tension. In embodiments, the brace includes a user mechanism that is capable of adjusting a tensioning element while the brace is being worn. In other embodiments, electronic motors, sensors, and indicators may be included in the brace to improve brace performance and user interaction.

26 Claims, 21 Drawing Sheets

Related U.S. Application Data continuation-in-part of application No. 17/537,476, filed on Nov. 29, 2021, which is a continuation-in-part of application No. 17/211,635, filed on Mar. 24, 2021, which is a continuation of application No. 17/074,542, filed on Oct. 19, 2020, which is a division of application No. 15/585,968, filed on May 3, 2017, now Pat. No. 10,806,619, application No. 17/902,683, which is a continuation of application No. 17/074,571, filed on Oct. 19, 2020, and a continuation of application No. 17/211,590, filed on Mar. 24, 2021, now Pat. No. 11,135,081, and a continuation of application No. PCT/US2020/047904, filed on Aug. 26, 2020, and a continuation of application No. PCT/US2022/021822, filed on Mar. 24, 2022.

(60) Provisional application No. 62/331,315, filed on May 3, 2016, provisional application No. 63/394,530, filed on Aug. 2, 2022.

(58) Field of Classification Search
CPC .. A61F 2013/49096; A61F 5/01; A61F 5/026; A61F 5/028; A61F 2/30; A61F 2002/30624
See application file for complete search history.

(56) References Cited

U.S. PATENT DOCUMENTS

| | | | |
|---|---|---|---|
| 5,807,294 A | 9/1998 | Cawley et al. | |
| 6,953,442 B2 | 10/2005 | Yamasaki et al. | |
| 7,201,728 B2 | 4/2007 | Sterling | |
| 7,553,289 B2 | 6/2009 | Cadichon | |
| 7,608,051 B1 | 10/2009 | Nace | |
| 7,927,299 B2 | 4/2011 | Krause | |
| 8,057,414 B2 | 11/2011 | Nace | |
| 8,123,709 B2 | 2/2012 | DeHarde et al. | |
| 8,308,669 B2 | 11/2012 | Nace | |
| 8,376,974 B2 * | 2/2013 | Nace | A61F 5/0123 601/35 |
| 8,444,583 B2 | 5/2013 | Phillips | |
| 8,945,035 B2 | 2/2015 | Nace | |
| 10,070,983 B2 | 9/2018 | Garrish | |
| 10,188,539 B2 | 1/2019 | Garrish et al. | |
| 10,682,249 B2 | 6/2020 | Kazerooni et al. | |
| 10,744,020 B2 | 8/2020 | Garrish | |
| 10,893,959 B2 | 1/2021 | Boiten et al. | |
| 2004/0068215 A1 | 4/2004 | Adelson et al. | |
| 2010/0056967 A1 | 3/2010 | Nace | |
| 2011/0009787 A1 * | 1/2011 | Pallari | A61F 5/0127 602/16 |
| 2011/0105969 A1 | 5/2011 | Nace | |
| 2012/0271211 A1 | 10/2012 | Bledsoe | |
| 2013/0035623 A1 | 2/2013 | Nace | |
| 2013/0190669 A1 | 7/2013 | Rokosz et al. | |
| 2014/0180185 A1 | 6/2014 | Zachariasen | |
| 2015/0173929 A1 | 6/2015 | Kazerooni et al. | |
| 2016/0143763 A1 | 5/2016 | Hsu et al. | |
| 2018/0333285 A1 | 11/2018 | Thor et al. | |
| 2020/0170821 A1 | 6/2020 | Lurssen et al. | |
| 2021/0022901 A1 | 1/2021 | Garrish | |
| 2021/0100673 A1 | 4/2021 | Siewert | |

FOREIGN PATENT DOCUMENTS

| | | |
|---|---|---|
| WO | 1996020659 A1 | 7/1996 |
| WO | 2005046536 A1 | 5/2005 |
| WO | 2005107659 A2 | 11/2005 |
| WO | 2015018340 A1 | 2/2015 |
| WO | 2022197280 A1 | 9/2022 |

OTHER PUBLICATIONS

"Design, Construction and Evaluation of an Electromechanical Stance-Control Knee-Ankle-Foot Orthosis", Terris Yakimovich, Terris and Edward D. Lemaire; 2005 IEEE Engineering in Medicine and Biology 27th Annual Conference (2005): 6934-6941.

"Medi M4s OA Knee Brace for Arthritis at DME-Direct.com", (https://www.youtube.com/watch?v=u8I9yrYLaMs, Published on Sep. 9, 2015).

Ramsey and Russell, "Unloader Braces for Medial Compartment Knee Osteoarthritis: Implications on Mediating Progression", Sports Health, vol. 1, No. 5: 416-426.

"Custom Adjustable OF Defiance", Donjoy, http://www.djoglobal.com/products/donjoy/custom-adjustable-oa-defiance.

Johnson, SA et al., "Gait and clinical improvements with a novel knee brace for knee OA," J Knee Surg. Jun. 2013; 26(3): 173-8. Abstract.

Spring A, Kofman J, Lemaire E. Knee-extension-assist for knee-ankle-foot orthoses. Annu Int Conf IEEE Eng Med Biol Soc. 2011;2011:8259-62. doi: 10.1109/IEMBS.2011.6092036. PMID: 22256260.

https://fillauer.com/products/knee-extension-assist/ as downloaded on Nov. 7, 2022.

https://www.beckerorthopedic.com/Product/CustomFabricationServices/CustomStanceControl/318 as downloaded on Nov. 7, 2022.

https://www.oandplibrary.org/popup.asp?frmItemId=847D97D3-E6E9-4A16-8B87-130579F3C6E2&frmType=image&frmId=4 as downloaded on Nov. 3, 2022.

"KAFO with Extension Assist to prevent knee buckle", (https://www.youtube.com/watch?v=psex38WmwxM; Published on Aug. 14, 2013).

"Fullstride KAFO Mechanism.AVI", (https://www.youtube.com/watch?v=594bp-YL9Gw; Published on Sep. 5, 2010).

"Design and Analysis of a Stance-Control Knee-Ankle-Foot Orthosis"; Kieran J. Eveleigh, Marc Doumit; University of Ottawa, Mechanical Engineering Department; 2019; https://www.resna.org/sites/default/files/conference/2019/wheelchair_seating/Eveleight.html.

https://shop.ottobock.us/Orthotics/Custom-Orthotics/KAFO-KO---Knee-Ankle-Foot-Orthosis-Knee-Orthosis/C-Brace/C-Brace/p/17KO1 as downloaded on Nov. 7, 2022.

"Engineering design review of stance-control knee-ankle-foot orthoses", Terris Yakimovich, Edward D. Lemaire, Jonathan Kofman; Journal of Rehabilitation Research and Development, vol. 46 No. 2, 2009 pp. 257-268; https://www.rehab.research.va.gov/jour/09/46/2/yakimovich.html.

* cited by examiner

Figure 5a
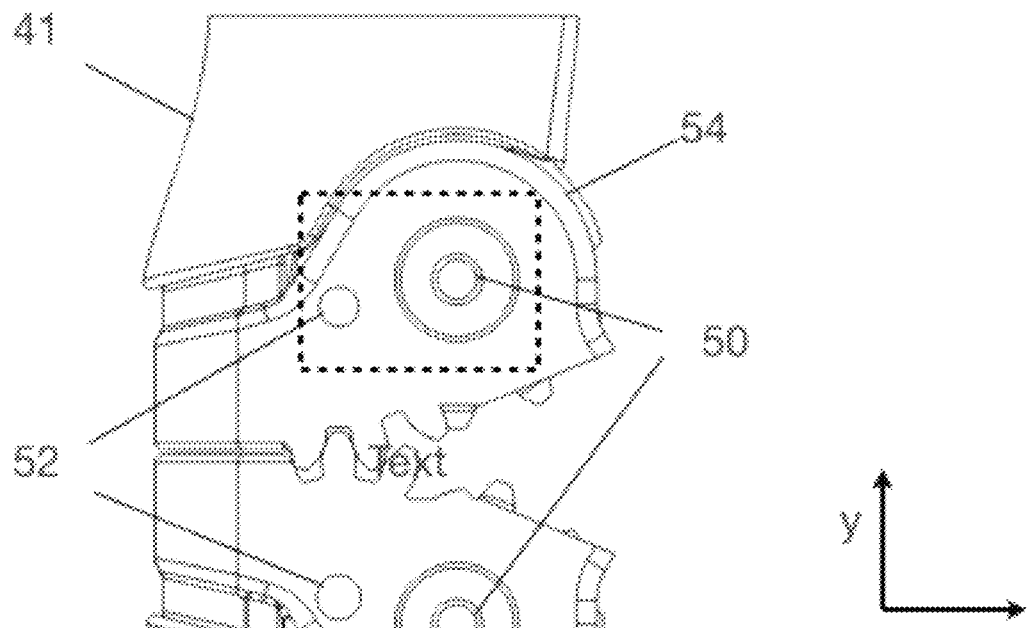
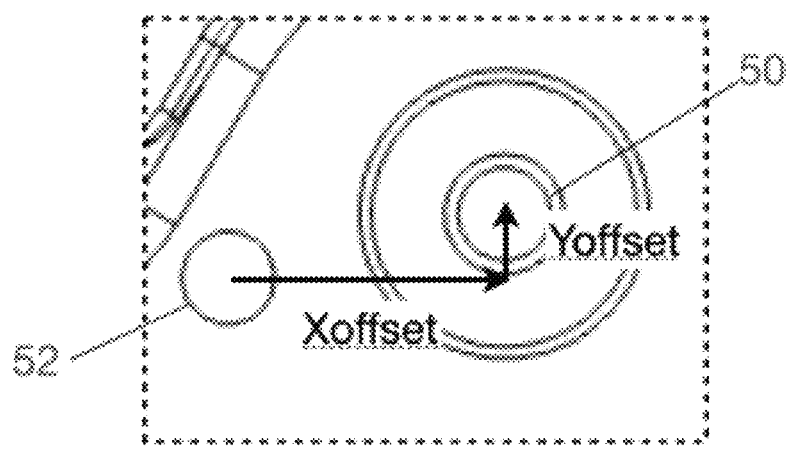

UNLOADING KNEE-ANKLE-FOOT ORTHOTIC APPARATUS WITH CONFORMING AND DISTRACTING HINGE

CROSS-REFERENCE TO RELATED APPLICATIONS

The present application is a child application of and relies on the disclosures of and claims priority to and the benefit of the filing dates of the following, and the disclosures of the following applications and other applications/patents/literature cited herein are hereby incorporated by reference herein in their entirety:

U.S. patent application Ser. No. 17/700,479, filed Mar. 21, 2022,
U.S. patent application Ser. No. 17/537,476, filed Nov. 29, 2021,
U.S. patent application Ser. Nos. 17/211,590 and 17/211,635 filed Mar. 24, 2021,
U.S. patent application Ser. Nos. 17/074,571 and 17/074,542, filed Oct. 19, 2020,
U.S. patent application Ser. No. 15/585,968, filed May 3, 2017,
U.S. Provisional Patent Application No. 62/331,315 filed on May 3, 2016,
PCT Application No. PCT/US2020/047904, filed Aug. 26, 2020,
PCT Application No. PCT/US2022/021822, filed Mar. 24, 2022, and
U.S. Provisional Patent Application No. 63/394,530, filed Aug. 2, 2022.

BACKGROUND OF THE INVENTION

Field of the Invention

The present invention disclosed herein relates generally to knee-ankle-foot orthoses to relieve pain and discomfort by unloading the joint by redistributing the weight on the knee joint to other parts of the body and/or providing assistance in extension of the joint.

Description of Related Art

Osteoarthritis (OA) is a degenerative joint disease characterized by chronic inflammation, breakdown, and eventual loss of the joint cartilage, causing deterioration of the underlying bone. The patellofemoral compartment, in particular, is one of the most frequent points of knee pain experienced by those with OA. While unloading braces have been used as inexpensive therapeutic solutions for knee OA, they have been overwhelmingly ineffective in preventing and reducing joint pain. The various embodiments of the present invention aim to design a knee orthosis that unloads the knee joint and reduces pain on a knee joint impaired by OA. The orthoses described herein are, among other things, focused on the transfer of forces away from an injured region of the knee, or unloading weight from the anterior region of the knee for patients suffering from patellofemoral pain (PFP) or patellofemoral arthritis.

Arthritis is currently the most common cause of disability among adults in the United States. More than one hundred different rheumatic conditions fall under arthritis, the most common of which is osteoarthritis (OA), a degenerative joint disease marked by a chronic deterioration of joint cartilage and the underlying bone. OA is one of the most common joint disorders in the United States, and the number of those afflicted is only projected to increase in the midst of an aging population and increasing levels of obesity. Twenty-seven million adults in the U.S. alone are affected by the disease. As the most typical type of arthritis, the disorder has commonly affected the knee, and the patellofemoral (PF) compartment within the knee joint in particular has been one of the most frequent points of knee pain in the outpatient setting. The PF compartment performs a key role in daily movement and activity, enabling mobility over a large range of motion through flexion, extension, and rotation of its associated components. One of the most non-invasive and widely accepted methods for prevention of further deterioration of the articular cartilage within the knee joint is by using a knee orthosis. The joint itself, including its underlying cartilage, can only support a certain amount of force before the cartilage begins to wear away. An unloading knee orthosis can decrease the amount of force on the joint.

According to the American Academy of Orthopedic Surgeons and the U.S. Center for Disease Control and Prevention, nearly half of Americans develop symptoms due to knee OA by the age of 85, and the incidence rate for PF pain syndrome has been reported to be approximately 22 adults for every 1000 adults per year. In addition, up to 10 percent of the U.S. population suffers from pain and loss of function from patella arthritis and cartilage wear. The high prevalence of these injuries suggests that the condition affects a significantly large portion of the adult population and will have a growing impact on healthcare systems in the future. On average, total knee arthroplasty, or knee replacement surgery, costs between $10,000 and $30,000, and over 600,000 surgeries are performed each year. Other surgical procedures such as articular cartilage restoration, osteotomy, and unicompartmental knee replacement, as well as corticosteroid and hyaluronic acid injections to reduce inflammation and absorb shock, respectively, are also very expensive. Thus, preventative treatments that reduce the amount of stress, pressure, and invasive procedures on the knee are necessary for improving the quality of life for patients and for reducing potential medical costs.

In addition, robust braces enable those with severe joint injuries to remain active when joint replacement is not appropriate. It is estimated that 27 million adults in the U.S. are suffering from osteoarthritis, and 454,652 patients with severe joint injuries and arthritis received knee replacement surgeries in 2004. Currently, nonpharmacological approaches, such as physical therapy, and pharmacological methods are primarily used to treat knee OA. When these are proven to be ineffective, the treatment method culminates in surgery, and drawbacks involve internal joint bleeding, bone healing failure, nerve or tissue damage, and infection. Thus, the development of a knee orthosis that significantly unloads force on afflicted joints, prevents pain and disability, and does not require many other treatments in conjunction is necessary to address the challenges associated with establishing a purely non-pharmacological, orthotic approach to treating knee OA. An aim of the various embodiments of the present invention is to develop a knee orthosis that significantly unloads force from the patellofemoral compartment of a knee joint afflicted with osteoarthritis in order to relieve pain and disability.

Other conditions such as knee flexion contracture (KFC), quadriceps weakness, and neurological conditions that impact proper muscle and joint function, are also lacking in treatment options. A brace according to the current invention that can transfer forces away from the knee joint and quadriceps has promise to uniquely benefit patients who may suffer from these conditions. Transferring forces away from the joint may also allow the patient to delay or prevent surgical procedures such as a joint replacement.

OA Knee Orthosis

Osteoarthritic knee orthosis primarily comprise a rigid, or semi-rigid, frame with an upper frame member called an "upper cuff" situated across the anterior thigh, and a "lower cuff" across the anterior or posterior tibia; and, straps are on the opposing side of the cuffs to secure the frame onto the user's leg.

In OA, the disease process includes degradative enzymes that erode the articular cartilage, leading to bone-on-bone contact, which is the primary source of the user's knee pain. OA knee orthosis classified as "unloading" braces pull the femur and tibia apart so that there is not bone-on-bone contact when the user is load bearing, such as walking, standing, exercising, etc. This is accomplished by the brace lifting the femur, and/or pulling down the tibia, or otherwise keeping the femur and tibia condyles from making direct contact through the actions of the upper and lower cuffs locking the femur and tibia in positions relative to the other.

Unloading knee orthosis may also comprise hinge assemblies that exert a force in the medial to lateral direction to push the knee joint inward, thus separating the femur and tibia condyles. For example, there may be one hinge assembly in the brace, such as for a brace to treat OA in the left medial compartment with a hinge assembly on the medial side of the knee joint; or hinge assemblies on both sides. The hinge assembly may comprise a component (e.g. an inflatable pad) that pushes the knee joint laterally, e.g. inward and/or apart, to unload forces on the medial side of the knee, and thus reduce the user's pain.

The hinges in unloading knee orthosis may also comprise components similar to a built-in braking system where the user experiences an increase in tension as the knee is bent to prevent the user's knee from collapsing while bending. The hinge assembly and cuffs engage in a majority of the work that the leg muscles would otherwise do to stabilize the knee joint through its entire range of motion.

More recently, a number of OA knee orthoses have been marketed to consumers who wish to maintain an active life-style in spite of their medical condition. OA knee orthosis are now available that comprise hinge assemblies with the ability to exert forces to assist the user in movement, otherwise known as "swing assistance" or "knee extension assistance". The hinge's exerted restoring forces can be counter to the user's original direction of movement, such as propelling the user's knee from a flexed to an extended position after the user has bent down. The restoring force generated from the compression or stretching is used to assist the user when they move to extend their leg.

However, the current industry requires a knee orthosis, and a knee ankle foot orthosis that effectively both unloads the user's weight off of the affected joint while dampening downward forces and generating restorative resistance forces that provide stability and support to weakened muscles. It would also be beneficial if the knee orthosis provides knee or ankle extension assistance to the active user. There is also a need for an improved mechanism of unloading that does not require pushing the knee inward, but instead relies upon a well-fitting rigid or semi-rigid frame and straps, and/or hinge assemblies that are of an adjustable tension that can be activated by the user as needed, and of significantly higher tension levels than the existing state-of-the-art to engage in the mechanical work that is normally done by the muscles of the knee while pulling the femoral and tibial condyles apart.

Full and Partial Leg Orthotics

Knee-Ankle-Foot-Orthotics (KAFOs) and Hip-Knee-Ankle-Foot-Orthotics (HKAFOs) are braces that include the knee joint but also provide support to the ankle and/or hip joint for patients who have additional joint mobility needs. A health study in 1997 found that over a million people in the United States were using KAFOs. There are many types of KAFOs and HKAFOs made to treat the various combinations and permutations of hip, knee, and ankle-joint disorders. A subset of patients who suffer from knee OA have other joint orthosis needs that would be served by a KAFO or HKAFO rather than just a knee orthosis. Thus there is also a need to provide an OA unloading solution for KAFOs and HKAFOs, which is addressed according to the current invention.

SUMMARY OF THE INVENTION

Various embodiments of the present invention provide a novel type of unloading KAFO or HKAFO that has been designed to reduce the amount of pain that patients experience as a result of PFP or knee joint OA. The knee orthosis elements and knee hinge assemblies of the KAFO or HKAFO disclosed herein work by using one or a combination of the following mechanisms:

1) mechanisms of generating a force or forces opposing the bending or contracting/flexion of the knee joint and thereby unloading the joint, 2) hinges that distract forces from one or both sides of the knee in the tibiofemoral compartments, 3) adjustable tensioning systems designed to control forces around the knee, hip, or ankle joint to provide stability and improve gait based on the user's need, and/or 4) devices that are personalized to the user to address their specific indication, including adjustable tensioning mechanisms, 3D scan to fabrication methods, and modularity of the knee orthosis (KO), ankle-foot-orthosis (AFO) and hip orthosis (HO) components.

As described in U.S. Pat. No. 10,806,619, the hinge assemblies described therein are suitable for a knee joint, an elbow joint, an ankle joint, a shoulder joint, a hip joint, or a wrist joint; while application of this technology for the knee joint for a KAFO or HKAFO will be presented here in detail, one of ordinary skill in the art could readily apply this disclosure and teachings herein to other multi joint orthotics (e.g., a shoulder-elbow brace) where the unloading hinge assembly is incorporated into at least one of the joint elements.

The KAFO or HKAFO described herein effectively unloads an amount of force within the knee by using a low- to high-tension resistance mechanism, and by distributing the force to other areas of the body. This results in reduced contact pressure in areas of the knee afflicted with OA, and therefore less pain. Other braces are described that have different mechanisms of unloading or distracting pressure in joints as well.

Some embodiments described herein allow the user to quickly (e.g., in aspects from about 1-5 seconds, for example) engage and disengage tension in each joint mechanism as needed, including in aspects while the brace is being worn; adjust the amount of tension, including while the brace is being worn and without the need for a medical professional's assistance; allow for tension to increase with increasing degrees of flexion; and limit the range of extension and flexion in the joint. The unloading device when incorporated in a KAFO or HKAFO is particularly suitable for people afflicted with patellofemoral osteoarthritis (OA), cartilage damage, meniscus damage, knee stability issues, and other types of knee conditions for which pain intensifies during the bending or contracting of the knee. It may also provide improved assistance for patients who lack the strength (e.g., due to quadriceps weakness, stroke or neurological deficiency) to extend their knees either during exercise or simple life functions, such as standing from a seated position. The various embodiments of the KAFO or HKAFO and hinge assemblies disclosed herein provide enhanced support for stabilizing the knee joint, and they can enhance the user's physical performance by providing extension assistance. Another version of the KAFO or HKAFO may have the tensioning elements oriented such that the brace resists extension and assists with flexion. The tensioning system may be integrated in the KO, AFO, or HO component to control forces in a desired direction around the desired joint or joints.

Unloading Brace Vertical Support

The various embodiments of the present disclosure comprise a KAFO or HKAFO that effectively unloads the user's weight off the knee joint via a KO component with a rigid or semi-rigid vertical support that, in aspects, partially or completely connects to the user's femur and tibia, and with a pivoting hinge assembly connecting an upper and lower portion of the vertical support wherein an ankle-foot and/or hip orthotic is connected, attached, or extended to/from the vertical supports. In some embodiments, the at least one lower vertical support extends beyond one to three straps on the lower portion to connect or attach to an ankle-foot orthotic. In other embodiments, the at least one upper vertical support extends beyond the one to three straps to connect or attach to a hip orthotic. In yet other embodiments, the at least one lower and at least one upper support connects or attaches to both an ankle-foot orthotic and a hip orthotic, respectively. Similarly, the supports of the unloading hinge element may extend beyond the straps of, for example, an elbow joint, to connect to, for example, a shoulder orthotic. In this manner, the unloading hinge assembly described in U.S. Pat. No. 10,806,619 can be incorporated into one or more joints of a multi joint orthotic.

The various embodiments of the unloading hinge assembly disclosed in U.S. Pat. No. 10,806,619 are incorporated herein by reference. Where the supports for the unloading joint orthotic comprise an arcuate, curved, semi-circular rigid or semi-rigid unit situated above and below the knee it is advantageous that the ankle-foot orthosis, hip orthosis, or both connect or attach to the said supports. In the case that the rigid or semi-rigid supports are connected or contained within an elastic sleeve or support that partially or fully encompasses the knee, the ankle-foot and/or hip orthotic may be connected or attached to the unloading knee hinge assembly by either the rigid or semi-rigid supports, the elastic sleeve or support, or combinations thereof. Likewise, for unloading hinge assemblies for joints other than the knee, similar combinations of connecting or attaching to the rigid or semi-rigid supports or elastic sleeve or support are disclosed.

The KAFO of HKAFO may incorporate a distracting hinge comprised of teethed gears, cams, or articulating members of variable radii, wherein the distance between the gear centers increases or decreases through flexion and extension. The gears may be connected by a hinge cap and may contain slots and pins to guide the path of distraction. Alternatively, the distraction hinge may incorporate a series of two or more gear systems, wherein a second gear system engages and articulates at a specific range of flexion and provides a greater distance, therefore a distracting force, between the upper and lower portions of the orthosis. Similar distraction hinge mechanisms may be present in an ankle foot orthosis component of the KAFO or within the hip orthosis component of an HKAFO to provide distraction across the intended joint or joints. The distracting hinge provides a distracting force between the upper and lower portions of the KO, AFO, or HO in order to separate or unload the joint. For example, a KAFO may comprise a distracting hinge on the lateral side of the KO component to unload an arthritic lateral tibiofemoral compartment.

Furthermore, the distracting hinge may be aligned with the patient anatomy in a way where the distraction engages and or increases in the areas of joint flexion corresponding with the patients' varying need for unloading, creating a dynamic unloading system that is proportional with anatomical unloading necessity. The various configurations of KAFOs and HKAFOs comprise a vertical support with an upper frame and a lower frame that are connected via a hinge assembly on one side (for a medial or lateral brace), or via two hinge assemblies (for a full brace). Likewise, medial, lateral, or full KAFOs/HKAFOs can benefit from unloading knee hinge elements for patients who have knee OA in one or more compartments, for which embodiments are disclosed herein.

AFO Component

The KAFO or HKAFO may comprise a multi-axis rotational control ankle-foot orthosis (AFO). The AFO component may comprise an adjustable tensioning system or systems to stabilize, support or prevent movement of the ankle joint in one or more axes. The AFO portion of the system may include a tensioning system that is linked to the KO or HKO, or isolated to the ankle or AFO. The tensioning system is meant to assist desired movement and/or resist undesired movement, and so tensioning elements and the tensioning system may be placed at different positions around the ankle or foot. The AFO portion may or may not have a hinge or joint. A geared joint may be used to distract parts of the ankle away from other parts as the ankle cycles through the range of motion, depending on what is desirable for the user. One such method of distraction involves the components of the hinge, such as at least one gear or curved surface that articulates with another gear or curved surface about a center that has a non-uniform radius or radii. This results in joint distraction and/or joint compression, which can be tailored in terms of sizing, placement, materials, flexibility, orientation, for example, to improve function and/or reduce pain in the joint.

The KO of HKO may be continuous with the AFO, or include a joint, or include a version of the rotation joint described above. One version of the rotation joint may be built into "struts" traversing down the leg, and another may allow the AFO to rotate about a partially and/or approximately cylindrical joint with the KO. The joint may also be entirely rigid, or such that some flexibility is allowed. The AFO may be attached to the KO with typical attachment mechanisms known in the art of prosthetics fabrication, using a snap-lock, dovetail system, pin-lock, or rotation lock, for example.

In addition to controlling forces around the ankle joint in the AFO component, the mechanism of multi-axis rotational control may be achieved across the hip, knee or ankle joint depending on the positioning of tensioning systems, the anchoring of tensioning systems, and the position and design of hinges (and corresponding rotational degrees of freedom) throughout the device. For example, replacement of the previously described polycentric hinge with a ball and socket hinge would allow rotational control along multiple axes of the knee joint, rather than one. Alternatively, a pivoting hinge in the vertical member above or below the polycentric hinge of the KO component would allow for rotational control around the longitudinal axis. Rotation of the joint around any axis may be limited, controlled, prevented, or supported at different stages of gait to better mimic the natural function of the joint, improve user comfort, or provide the desired outcome of joint unloading while minimizing limitations to the user's natural range of motion. The magnitude of rotational control around each axis may change dynamically with varying degrees of flexion in order to control gait in a highly precise manner. In aspects, the rotation control mechanism and function may be performed by a modular attachment, which can be combined with the KO, AFO, or HO component, or any other joint brace comprising adjustable tensioning systems, including existing braces that lack rotation control mechanisms.

Hip Orthosis Component

An HKAFO may comprise a hip orthosis component that contains an adjustable tensioning mechanism, separate from or continuous with the tensioning systems described in the KO and AFO components. In other embodiments, the unloading and assistive KO described may be extended upward to the hip to secure the orthosis to the body but also to optionally employ a similar hinge system in the KO to the hip, wherein the hip joint can experience assistance and/or resistance that is optionally adjustable by the user with an adjustment mechanism. The position and orientation of the tensioning or compression system may be modified based on the type, location, and the severity of the body injury. The device may optionally be extended beyond the knee to an ankle orthosis, or AFO, where the knee-AFO attachment is rigid, semi-rigid, or has a built-in rotation system to allow for natural rotation between the knee and foot. The assistance and resistance may be fixed, dynamic with flexion, or adjustable and/or variable at any point in the system of the orthoses. The rotation mechanism may also be fixed, dynamic, or adjustable and/or variable, and all can be tailored to the needs of the patient. The tensioning system of the hip component may be applied as in a hip abduction brace to prevent dislocation of the femur from the hip socket. It may also allow tensioning to further assist with gait, and work synergistically along with the KO and AFO components.

In embodiments, the tensioning systems of the HO, KO and AFO components may be connected directly or indirectly. For example, the user may add tension to the KO component to further assist extension of the knee, which also tensions the AFO system to support dorsiflexion, therefore preventing foot-drop. The connected tensioning systems may optionally contain pulley or gear systems that determine the relationship of forces and/or distance moved by the connected tensioning systems. For example, a gear system between the KO and AFO tensioning systems could allow for a lesser force applied around the ankle joint and a greater force applied around the knee joint while adjusting only one interconnected tensioning system. Additionally, gear, ratchet or other mechanisms may be used to engage the KO and/or AFO tensioning systems at specific points, for example at a certain range of flexion. This could be achieved by using a distracting hinge in one of the hinge mechanisms for either the AFO or KO component, allowing for additional unloading forces based on the flexion of one of the joints, while still maintaining an interconnected tensioning system between the two joints. For example, a linear ratchet mechanism could be applied so that when a specific level of tension is sustained by the KO tensioning system, the AFO tensioning system will engage to support dorsiflexion. Tailored differences in the forces applied or path length of the tensioning elements may be achieved by applying different types of tensioning elements, for example elastic bands of different material properties, in each tensioning system to achieve the desired properties for the application. For example, use of an elastomer or spring with a lower Young's Modulus in the AFO tensioning system and an elastomer or spring with a higher Young's Modulus in the KO tensioning system would lead to different magnitudes of applied force around the knee and ankle joints while using one continuous, in-line adjustment mechanism.

Elements of an Assistive Orthosis

An assistive orthosis with an energy storage system comprises: a hinge that includes an energy storage system along with an adjustment mechanism, such as a rotary tensioning dial, an inelastic wire or lace, and optionally a spring or elastic band; gears or curved surfaces that articulate to create a pulling or tensioning force; and a means to attach the hinge to the joint or body part. The energy storage system may be either a tensioning system (e.g., wherein energy is stored by the system under tension) or a compression system (e.g., wherein energy is stored by the system under compression). This system also comprises unique housing and structure to contain a system that may be subjected to high tension or compression. The structure may be comprised of blocks or segments that can flex and/or articulate around to conform to a body part, or into a desired shape. These blocks or segments may make contact or articulate about each other. The system, in aspects, may optionally comprise one or more "tubes" or channels to house the tensioning bands (when used), shaping elements including but not limited to bendable plastics and wires, and another "tube" to contain the wire or lace that exerts tension or force required to achieve the desired effect in each joint. These materials should be sized properly to meet the torque and tension requirements, as well as compact to make the device wearable, and in aspects they should have high strength and low friction to meet the durability requirements of a high-quality product. This amounts to a unique tensioning hinge and system, which may be embodied by a hinge kit, that contains blocks or segments that can articulate around and/or with the aforementioned "tubes" that can optionally have wires contained within the parts to allow for shaping or structuring the blocks or segments, and that can slide or move along the blocks or segments. In aspects, at least one block or segment can house the tensioning mechanism or dial, which then connects to the tensioning wire or lace, which may or may not include a tensioning band. This system can include gears or curved surfaces that articulate around each other that may increase or decrease tension with joint articulation. This system may be added to existing devices to convert a device into a tensioning or assistive device, or may constitute the basis of a device in and of itself. This system may be glued together to hold components in place, and/or may be covered, wrapped, or structured with another material or combination of materials to improve usability, such as carbon fiber, fiberglass, or other plastic materials. This system can create a resistive or assistive hinge or system depending on the arrangement of the components and selection of components. For example, assembling the hinge with an in-line spring at the anterior region of the joint would serve an assistive function, while placing the same spring at the anterior region of the joint would serve a resistive function with regards to knee extension. This system may be utilized in either the upper frame, lower frame, a portion of either the upper frame or lower frame, or both the upper frame and lower frame.

KAFO Hinge

The unloading function of a knee orthosis described herein occurs when several components work in concert such that the combined contributions of components generate an unloading force that is transmitted to the wearer's knee. As designed, in aspects, the components have multiple functions and interact with each other to produce the desired result. For example, the frame component's primary function is to transmit the unloading forces generated to the wearer's leg, but it also serves to anchor the adjustment component and contributes to the camming action of the hinge component, by way of example.

There are instances when a traditional knee orthotic frame is not desired or cannot be worn. In embodiments, in order to achieve the same patellofemoral compartment unloading, there is a need to design the unloading components of a knee orthosis described herein such that they are modular—that is, independent yet function together when assembled into an article (such as a prosthetic or orthotic.)

Hinge Module

In embodiments, the hinge module comprises an eccentric cam, a tension element pathway, and a hinged connection between the frame elements above the knee and below the knee. In one embodiment the hinged connection is a polycentric hinge. In other embodiments, the hinged connection is a distracting hinge. In yet another embodiment, the hinged connection is a combination rotational/glide motion that mimics the natural motion of the knee when flexed.

In other embodiments, the actual element (for example, a Teflon™ tube of specific dimension) can be incorporated into the finished part.

In this manner, a hinge module could be incorporated, fabricated, or combinations thereof, into a prosthetic or other orthotic that enables proper hinging action and yet will interact as intended with the modular tension and adjustment components.

Tension Module

The tension module comprises an energy storage element and a linking element that connect the portions of the prosthetic or other orthotic below and above the knee. (In a traditional knee orthotic the lower frame corresponds to the below the knee element and the upper frame corresponds to the above the knee element.) Optionally, the tension module also comprises a guide element to constrain the linking element.

In aspects, the energy storage element may be one or more of elastomeric bands, webs or other geometries, springs (including but not limited to linear springs, leaf springs, torsion springs, garter springs, and spiral springs) torsion bars, pneumatic elements or springs, electromagnetic elements or springs, pressurized air chambers, coils, hydraulic elements or springs, piezo electric materials, biomimetic materials, or any component that may act as a mechanical energy storage element/spring, or combinations thereof.

The linking element is preferably substantially inelastic to effectively transmit the forces generated by the energy storage element. The linking element may comprise a line, cable, braided cord, chain, lace, string, band, or the like. The linking element serves to connect the tensioning element to either the adjustment module, the structure of the prosthetic or orthotic, or both.

If the path from the adjustment module to the tensioning element is a straight line then a guide element for the linking element may not be needed. However, if the path needs to follow a curve then a guide element for the linking element is preferred. For example, if the adjustment module is positioned in front of the wearer's thigh and the tensioning element is positioned laterally to the wearer's knee, the straight-line path between the two elements would intercept the wearer's leg. Thus, in this example, a guide element to define the curved path for the linking element may be required.

In some embodiments, the guide element can be built into the prosthetic or orthotic structure directly. For example, a channel or tunnel could be created during the composite layup of a prosthetic that could be used as a guide element for the linking element. In other embodiments, a tube or other structure that defines the path of the linking element could be incorporated into the composite layup. In yet other embodiments, a sacrificial or temporary material (e.g., a wax tube, a PTFE cord, etc.) could be incorporated during the composite layup to define the guide element in the structure, but would be removed from the article once it had set.

If the force vectors applied to the linking element by the tensioning element and the adjustment element are not in-line (as will be common in practice), there can be an orthogonal vector on the tensioning element forcing it into the guide element. Thus the material that makes up the guide element needs to be strong enough to withstand those orthogonal forces. In addition, the guide element should provide a low friction, durable surface for the linking element along which to move.

If the guide element is to be incorporated into the prosthetic or orthotic, it should bond well to the materials being used to make the prosthetic or orthotic. The guide element should not kink or pinch the linking element. Likewise, if the materials used to make the prosthetic or orthotic need to be cured or set at a temperature above ambient temperature, the guide element should withstand those elevated temperatures.

Examples of guide elements are cable guides such as used for bicycle brake cables, ball and socket connectors, tubing, and the like.

In some aspects, it may be desirable to provide a unitary tensioning and linking element. For example, a plug or anchor could be incorporated into at least one end of an elastic tensioning element. If the plug or anchor is mated with a receptacle in the prosthetic or orthotic then that would provide a linking element to the structure of the prosthetic or orthotic.

In other aspects, a tube, string, pipe, cable, or lace-like structure could be incorporated into at least one end of an elastic tensioning element. The lace-like appendage would act as the linking element to be affixed to the adjustment module.

As mentioned above, the linking element connects the energy storage element to the adjustment module and/or the structure of the prosthetic or orthotic. In some aspects the linking elements that connect the energy storage element to the structure and to the adjustment module are the same (e.g., the linking element that connects the energy storage element to the structure and the linking element that connects the energy storage element to the adjustment module are braided cord). In other aspects the linking elements may differ (e.g., the linking element that connects the energy storage element to the structure is a unitary plug and the linking element that connects the energy storage element to the adjustment module is a braided cord.)

Adjustment Module

The adjustment module allows the wearer to tailor the unloading force to their needs while the prosthetic or orthotic is being worn. In embodiments, the adjustment module comprises the adjustable element and an anchor element. In aspects, the adjustable element can have two modes: an increasing of unloading force mode and a releasing of the unloading force mode. In some aspects a third mode is provided: a decreasing of the unloading force mode.

There are examples of mechanisms that can serve as the adjustable element including lever arms, rotating dials, ratcheting handles, pulleys, rack and pinion assemblies, wedges, cams as well as switches, buttons, potentiometers, slides to control powered components such as motors, servos, actuators, and the like. Methods for tailoring the unloading force such as adding or subtracting elastic elements are also possible. Similarly, notched or perforated band/belt could be positioned on a peg, post, or other receptacle to provide the adjustment function.

A non-limiting example of a suitable adjustment module is a tensioning dial (such as those manufactured by BOA™ Technologies of Colorado Springs, Colo.) as the adjustable element and a socket adapted to secure the tensioning dial as the anchoring element. Twisting the tensioning dial winds a lace onto an internal spool. In aspects, the device may require a tensioning dial with greater durability and the ability to generate and maintain greater torque than current on-market tensioning dials. In such cases, embodiments of the device may comprise a high-torque tensioning dial (capable of maintaining over 200 in-lb of torque after repeated applications, for example), which is designed to achieve, in aspects, greater degrees of mechanical advantage of at least four-to-one. Such a system may include combinations of multiple planetary gear systems, compound gear systems, or torsion gears. In other aspects, applications of the device may require a tensioning dial or adjustment mechanism that is easier to engage and disengage than current on-market technologies while being capable of maintaining high torque. For example, a tensioning dial that can be disengaged with a push-button mechanism to move pawls or the gear system itself could allow for easier use by individuals suffering from dexterity limitations due to neurological disorder or stroke. In the case where the other end of the lace is connected to an elastic energy storage element, twisting the dial increases the unloading force generated by the Hinge Module, Tension Module, and Adjustment Module assembly, for example. Pulling on the dial releases the internal ratcheting mechanism of the tensioning dial. In order to secure the adjustable element to the prosthetic or orthotic, a socket can be incorporated in the frame or support of the prosthetic or orthotic. Preferably the socket has a pathway or guide for the linking element of the Tensioning Module (a lace, in this example) and optionally a means to secure one end of the guide element.

The design of the adjustment module, as well as the positioning on the KAFO or HKAFO itself, allows for the user to adjust the tension in the device, the weight unloaded from the joint and the stability provided in real time during activity. This is important in order to accommodate the user's desired activity at a given point in time. For example, the adjustment mechanism may be adjusted to low tension while the user is walking, medium tension while the user is biking, and high tension while the user is performing a squat. The tension may be released rapidly altogether disengaging the energy storage system by, for example, pulling the adjustment dial out or pressing a button. The user is able to rapidly adjust the level of support based on their current pain level, allowing for an instant feedback loop by which the device's level of support can be optimized to the user need.

Distraction Hinge for Unloading

A "distraction hinge" as described herein may also be integrated to create a system that reduces inter-joint forces by pushing a joint apart, for example by using a variable-radii hinge, or a hinge that relies on gears with different radii and/or different pitch and size characteristics, through different ranges of motion, resulting in a force that intentionally distracts a joint through a preferred range of motion, which may be tailored by the hinge designer. Similarly, joint compression may be achieved in an opposite manner if this is desired to improve joint function, or to induce distraction in one aspect of a joint by compressing another.

Individual components, energy storage systems, strap systems or adjustment mechanisms may contain motors and or sensors to cause activation, modulate the amount of energy stored within the energy storage system in tension or compression, in order to support or augment the user's gait. Inclusion of motors may allow for better control of high-power energy storage systems, including pneumatic and hydraulic springs or systems for high-torque applications, for example in exoskeletons. The activation may be responsive to the device itself via sensors, for example sensors that track the amount of in-line tension within a tensioning system or sensors that track a range of motion of a hinge of the device. Alternatively, sensors may be used to capture user information that drives the activation of motors or other outputs on the device. The device may be, for example, Bluetooth or Wi-Fi enabled to communicate with a mobile device, smart wearable technology, other orthopedic device, or any computer enabled system. The device may be automatically or passively operating through a series of motors or sensors, with tension or compression in the energy storage element being modulated dependent on specific sensory inputs, potentially including acceleration or motion of part of the joint, movement through a specific range of motion, a specific pattern of motion in general, EMG output of one or more muscles interfacing with the device or sensors, in-line tension, external temperature, or other biometric data. Alternatively, the device may be activated by a mobile device, smart watch, or any bluetooth or wifi-enabled device that can be paired. In the case in which the device comprises a tensioning system, the device may include an in-line tensiometer in order to detect the amount of energy stored in the tensioning system, and therefore the amount of force expected to be generated around or unloaded from the joint. The tensiometer, by way of example, may provide outputs on the amount of force applied specifically, or may indicate a "low", "medium," or "high," tension setting for the user to select the specific level of support desired. The output may be presented on the device, on a paired mobile device, or on any other graphical user interface. The user may be able to further adjust the tension setting using the interface on the orthotic device itself, or on the paired mobile device. Alternatively, the graphical user interface may provide reports of activity or recommendations on device usage and activities for exercise or rehabilitation purposes. Such reports may be provided remotely to the user's doctor to provide real-time insights into patient recovery, activity and compliance with prescribed device usage regimen. A pressure sensor incorporated in-line with the energy storage element, either a tensioning or compression element, may provide the same function and data outputs to the user as described. One skilled in the art would understand that various sensors and corresponding sensory outputs would provide analogous function to the in-line tension meter described. Electronic components of the device may be charged through external power sources, or may be charged as a function of movement of elements of the device (for example, by articulation of the hinge component during gait).

Personalized Design and Fabrication

The KAFO or HKAFO can be fully or semi-automatically designed by software that generates a digital model based on a 3D scan consisting of 3D point-cloud data sets, and optionally accompanied by information on the user such as the type of indication, severity of their indication, information on joint misalignment based on radiographic measurements, measurements extrapolated from 3D scans, other user biometric data such as height, weight, and age, or any combination of this information. The model developed can also use this information to develop implantable devices within the joint to improve joint function, which may perform synergistically or within a treatment scheme with the designed orthosis. The intelligent design of the orthosis, implant or combination may, for example, create a desired mechanical environment for cartilage growth on the implant or to guide how cartilage grows in the joint in a desired way. Artificial intelligence or machine learning can be used with or without finite element analysis to determine the shape of an effective or assistive orthosis or implant, and AI, machine learning, and FEA, or combinations thereof may consider all of the input data above to improve overall body mechanics. This approach may be applied to more than just the knee, but also the ankle and hip, and how these joints relate to each other to improve biomechanical function. Such methods may be applied to the shoulder, elbow, wrist, back, and neck joints, or combinations thereof.

In another embodiment, only the unloading knee joint assembly of a KAFO or HKAFO and/or the rigid or semi-rigid connecting or attachment elements can be fully or semi-automatically designed as described in the paragraph above, and they can be compatible for attachment with other AFO and HO components designed through alternate means.

Brace Materials

In embodiments, the vertical support of the unloading knee joint assembly is made from rigid and/or semi-rigid plastic, metal, other lightweight materials, such as carbon fiber or another suitable material that are mostly inelastic yet flexible, and thus distribute weight-load knee forces. 3D printing with common thermoplastics are preferable materials for fabricating the brace described herein. In embodiments, 3D printing may provide a scaffold over which carbon fiber can more easily be wrapped to yield a highly lightweight and durable device. The incorporation of 3D printing from digital design as a scaffold may further allow for the automated application of carbon fiber based on the form of the 3D printed scaffold and in combination with instructions or specifications from the digital design. In embodiments, the vertical support of the entire KAFO or HKAFO is made of substantially the same material. In other embodiments, the vertical support of the KAFO or HKAFO is made of different materials. For example, the unloading knee hinge assembly and proximate supports can be made from a 3D printed thermoplastic and can be connected or attached to a carbon fiber ankle-foot orthosis. Additionally, the quantity and/or shape and or/type of at least one material may be optimized by an AI software, or algorithm to control the rigidity of specific sections of the brace corresponding to an individual joint's mechanical needs.

The hinge assemblies, tensioning elements, flexion-extension stops, methods of engaging and disengaging tension, additional applications, motors and sensors, disclosed in U.S. Pat. No. 10,806,619 are incorporated herein by reference and may likewise be included into a KAFO or HKAFO.

Modularity

In embodiments, the KAFO or HKAFO is designed modularly so that the KO component may attach to a range of custom or off-the-shelf hip or ankle braces. In embodiments, it may also be able to be attached to a lower limb prosthetic. In other embodiments, any of the HO, KO, or AFO component may be modularly designed to incorporate other standard orthosis components. The modularity can be achieved by an adapter mechanism that provides a functional connection between the adjustable tension, unloading KO component and the HO or AFO component. Alternatively, the invention provides a functional connection between an adjustable tension unloading KO component and a lower-limb prosthetic. In embodiments, the adapter mechanism may be built into the knee orthosis component on the vertical support, or on the arcuate support, using for example strapping or padding components, or it may be a separate component that attaches to the vertical support and interfaces uniquely with the specific AFO (or HO in aspects). For example, the vertical support may contain a series of slots, which can be fastened to the upper portion of the selected AFO using rivets. The form of the vertical support can match the dimensions of a region of the AFO component, providing a complementary interface that can be rigidly and securely connected. The adapter mechanism may be designed to optimize strength for the specific user and application. For example, the knee orthotic component may be designed with an adapter mechanism that has increased interfacial surface area with which to attach to the selected AFO when used for a patient requiring swing-assist. Alternatively, a different adapter mechanism may be selected for a patient requiring a different AFO to address foot-drop. The adapter mechanism design may be selected based on the patient's target indication, the selected AFO, patient morphology or biometric data (e.g. BMI), or intended time and intensity of use. Additionally, the rigidity of the adapter mechanism may be selected to address the user need, for example providing a more flexible polymer for a patient with foot-drop and a more rigid polymer for a patient with instability issues.

The adapter mechanism may comprise, by way of example, mechanical slots, rivets, threaded holes, hook and loop, straps, buckles, clasps, screws, rivets, adhesives, fasteners, interlocking members, and/or other conventional attachment mechanisms. It may comprise 3D printed molds, in combination with these exemplary attachment mechanisms in order to provide a secure connection, and may include other similar attachment mechanisms that could be envisioned by one of ordinary skill in the art.

The adapter mechanism can be suitable for joining an adjustable tension unloading KO with an AFO, HO or a lower-limb prosthetic, and can be beneficial when a wearer has a need for a specialized function provided by a KO or a specialized function provided by an AFO that is not provided by another commercially available KAFO. In essence, the modularity of the invention allows for scalable production of KAFOs and HKAFOs with a great degree of functional and fit selection and specificity, with the ability to produce thousands of KAFO designs through combination of any current on-market and emerging digitally designed component using the described mechanisms and methods.

Beyond the modularity of the adapter mechanisms at the interface of the orthosis components themselves, regions of the orthosis may be modular and modifiable. Other embodiments include features for the adjustability of the device during the fabrication and fitment process. Such methods may be digital or manual. In some embodiments, all or part of the brace frame may be constructed as a flexible series of subunits or "building blocks" that may functionally attach to other components and can pivot or flex relative to the adjacent subunits. For example, a series of repeating nylon subunits may be connected internally by a wire or cable with space between them. The subunits can therefore be adjusted into a desired orientation and relative position in order to determine the overall path of the orthosis component, which is comprised of these subunits. The subunits can be permanently or reversibly fixed together using male and female ends, e.g., buckles or slots, and can be further fixed using adhesive, sonic welding or attachment methods. The result can be a custom-fit shape to accommodate the user, which can be quickly and easily designed at low cost, and which can avoid traditional time-consuming methods (e.g., casting and molding).

The formable subunit mechanism may also house features that allow for further device functionality such as adjustable energy storage mechanisms, where ports for tensioning elements and tensioning wires or lace run through the subunits. The brace can be built from any number of parts to achieve the shape, size, and/or function of the brace. The parts may be identical, or vary in size and shape. The brace can also be made to accommodate electronic components, such as sensors and motors. The building blocks can be connected with adhesive and/or covered with carbon fiber, fiberglass, or another material suitable for stabilizing the built orthosis and/or enabling a finished surface.

Sections of the brace lock, slide, or snap into place to create the shape that is desired. For example, parts of the brace may be removed after a surgical procedure to allow for swelling, but may then be re-inserted once swelling goes down. The process may be reversible, allowing for adjustments to be made in the event of a change of morphology or if desired for a treatment schedule. The same features may allow for the brace to accommodate different rehabilitation protocols. For example, one component, either one of the orthosis components or a mechanism such as a drop lock, may be added or removed at different stages of rehabilitation to accommodate a prescribed regimen.

The fit of the device material may be designed to allow for other methods of adjustment. For example, thermoplastics such as polypropylene or nylon may be selected to allow thermoformability of the frame during the fabrication process.

The modular design of the KAFO or HKAFO at the interface of hip, knee and ankle components and within the frame of each component itself allows for reduced fabrication time and cost as well as improved patient outcomes. The ability to highly tailor the adapter mechanism and to do so using digital methods, automated design, and applications of artificial intelligence allows for a wider selection of AFO components to meet the patient's specific need. It also reduces the degree of modification and adjustment required to either the KO or AFO in order to achieve the desired biomechanical outcomes. Additionally, by applying digital design, a library of data on biomechanics, user biometrics, and user outcomes can be applied to a specific patient case to achieve a more optimized outcome driven by outcomes data. It can also be extrapolated to help other patients.

Such modularity can provide for ease of manufacturing and to lower both manufacturing cost as well as cost to consumers and insurance companies by making the brace more adaptable to changing morphologies and changing needs of wearers. It also allows for a brace to be modified to accommodate multiple stages of use, either with changes to morphology or changing patient condition, therefore extending the useful lifetime of the brace without requiring a new brace to be fabricated.

A system that connects the hip and knee or the hip, knee and ankle may be desired for a user suffering from complications from a stroke, a neurological disease or arthritis, CMT, EDS, or another disorder, and may benefit from a system of assistive mechanisms and/or restraints to assist with mobility and/or stability. In aspects, under high tension levels in the knee, the brace resists flexion and offers stance control, helping the user maintain an upright posture, or may enhance mobility by moving forward and then letting gravity translate tension or resistance in the orthosis joints to swing the joint forward when desired, or resist movement when otherwise desired. The amount of tension or resistance can be tailored to the desired amount of swing or resistance, and one such adjustable tensioning system involves the Boa™ dial or a similar rotary reel, although this is not a limitation of or to the current invention. The ankle of the foot relative to the leg or tibia can also be controlled, either fixed or dynamically with the use of tensioning or elastic bands. Similarly, the swing of the leg below the hip can be assisted or resisted as desired with the described tensioning system. Such a system can be isolated for individual joints with individual controls (such as, but not limited to, a Boa™ dial) or a system that has one or more joints interconnected with one or more tension controllers, such as a Boa™ dial. For example, an assistance and resistance system translating from the hip to the foot, and any joint in between, may be controlled by a single tensioning system or more than one tensioning system, and the system may involve a series of cams and/or pulleys to achieve the desired movement, resistance, or assistance in each joint and between each joint.

BRIEF DESCRIPTION OF THE DRAWINGS

The above and other features, aspects, and advantages of the present invention will become better understood with regard to the following description, appended claims, and accompanying drawings where:

FIGS. 5a-5c are illustrations of a multi-axis distracting hinge, according to the present invention.

DETAILED DESCRIPTION OF VARIOUS EMBODIMENTS

As used herein, the term "proximal" is synonymous with top or upper, as in above the knee, or the side closest to the user's torso. Likewise, the term "distal" is synonymous with bottom or lower, as in below the knee, or the side furthest from the user's torso.

As used herein, the term "anterior" refers to the front of the knee and/or brace, and "posterior" the back. As seen in the figures when the hinge is oriented up-down, anterior is upward, and posterior is downward.

Throughout the following Detailed Description section, the same reference numbers refer to the same elements in all of the Figures.

Knee Foot Ankle Orthotic

Figure 1:
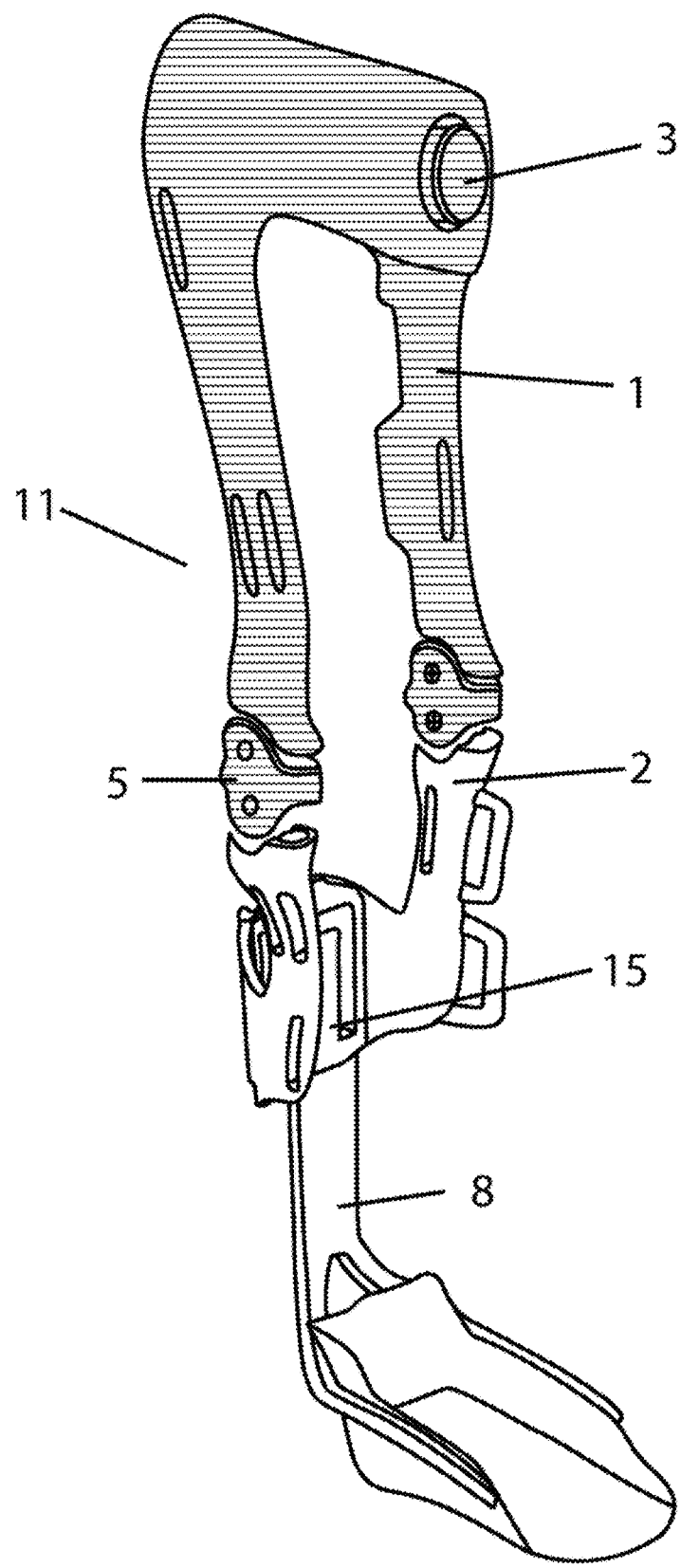
FIG. 1 is an illustration of a perspective view of the knee ankle foot orthosis (KAFO) in extended position, according to the present invention.
Figure 2:
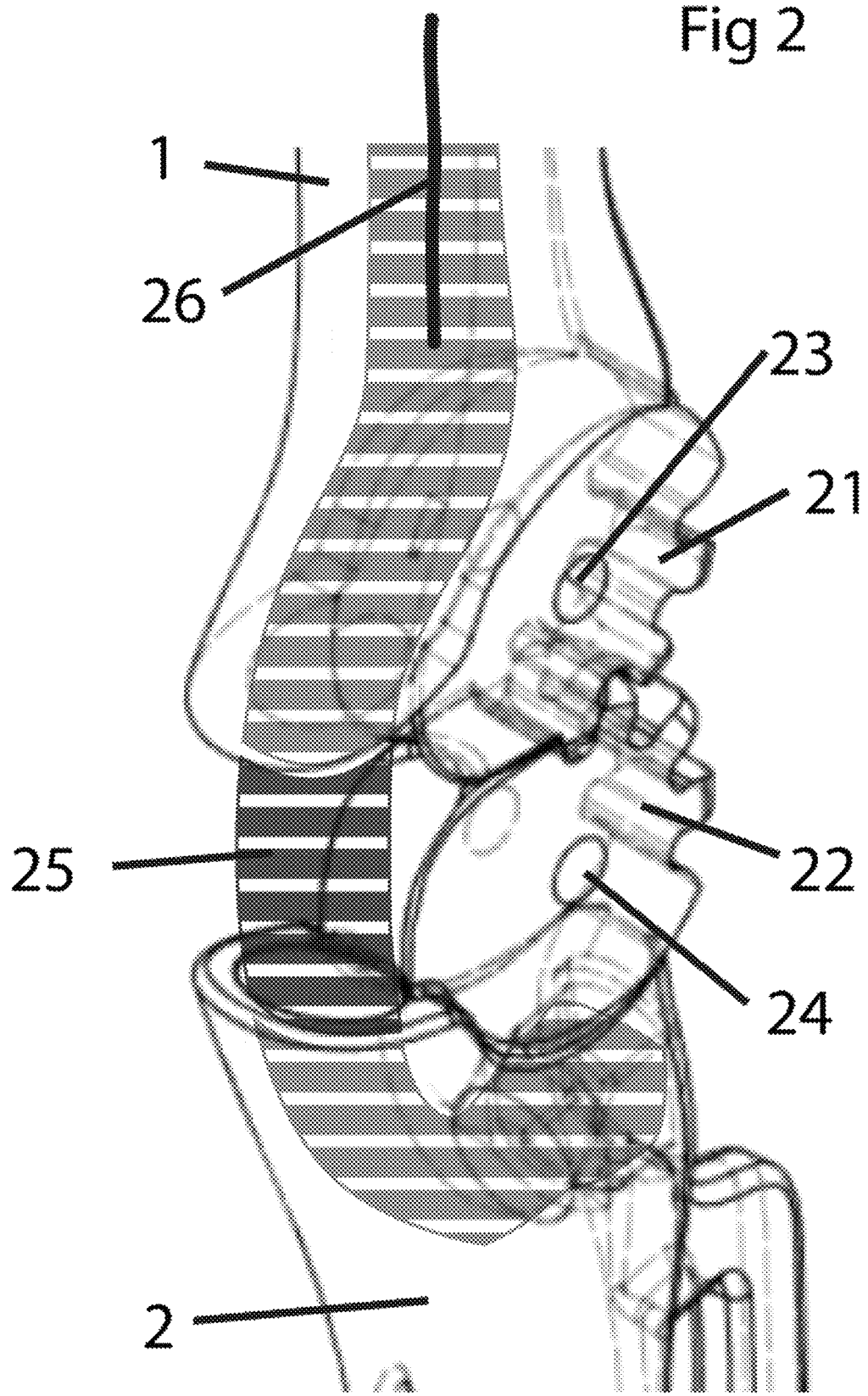
FIG. 2 is an illustration of the hinge assembly of the knee portion of a KAFO or HKAFO, according to the present invention.

FIG. 1 is a perspective view of a KAFO 11 comprising a knee orthosis (KO) frame, a geared pivoting hinge assembly 5, and an adjustable tensioning mechanism 3. As illustrated in FIG. 2, the KO frame comprises: an upper (proximal) frame 1, and a lower frame 2. In this particular embodiment, both portions 1 and 2 fit to the front side, or anterior surface, of a user's leg just above and below their knee. In an embodiment, the KAFO 11, such as in FIG. 1, is sized small, medium, or large, depending upon the outer circumference of the user's thigh; or, the knee orthosis is custom designed and fabricated to fit a specific patient's knee, which can be performed by an electric digital scan. Normally, the diameter and circumference of the upper frame 1 is larger than that of the lower frame 2. The ankle-foot portion of the KAFO, 8 in FIG. 1, is connected to the knee orthosis lower frame 2 using a connection 15.

Hinge Assembly

FIG. 2 is an illustration of one aspect of the hinge assembly of the knee orthotic element of a KAFO or HKAFO. In aspects, the present disclosure comprises at least five different pivoting hinge assemblies, in aspects comprising at least one tensioning element 25, and two geared teeth, comprising a proximal gear 21 and a distal gear 22. Each type of hinge assembly can be used to generate tension in a one-sided brace (hinge medial or lateral side) or a full knee orthosis (hinge medial and lateral sides). In embodiments, the hinge assembly proximal end is connected to the brace upper frame 1, and the hinge assembly distal end to the lower portion 2, or in a manner that would be understood by one of skill in the art.

The two opposing gears (21, 22) of the hinge assembly, can be connected via a center cap (not shown); the frame can have a proximal opening and a distal opening that houses the tensioning element 25 and allows it to stretch across the intermeshing gears, resisting flexion. As shown in FIG. 2, the polycentric teethed gears have central holes 23, 24, upon which the upper and lower frame elements 1, 2 rotate, respectively. Matching holes in the center cap are in line with the gear central holes 23, 24, which are functionally attached to allow for rotation around the gears while generating tension (or a breaking force, or a counter-restorative force), thus allowing the wearer of the brace to more easily flex and extend. The gears and the center cap may be functionally attached using screws, bolts, or another method known in the art. The center cap is able to function to, in aspects: pin the subunits together while enabling the gears to rotate in unison; protect the gears and tensioning element; and/or limit a maximum degree of flexion of the hinge assembly. In another embodiment, the element may be stretched under the gears, to assist with flexion; this may be used in a brace that is designed to help rehabilitate the knee after an injury. As shown in FIG. 2 the connection element, 26, ties the tensioning element 25 to the adjustable tensioning mechanism, e.g., 3 in FIG. 1. In other aspects, additional connection elements may connect the adjustable tensioning mechanism 3 to tensioning elements in the ankle-foot orthotic 8 portion of the KAFO.

The teethed gears can further provide a mechanism to limit the maximum extension of the tensioning elements and hinge assembly to prevent hyperextension of the knee using extension and flexion stops and, in aspects, radially oriented slots. The slots can allow for insertion of extension flexion stops, which can be pre-made inserts that restrict the range of motion of the joint. The extension and flexion stops will, in aspects, not permit the gears or hinge to rotate further once contact is made with the stops. The allowable surface angle between the gears' point of contact is a design variable that can be modified to satisfy user requirements. Additionally, the extension and flexion stops may be designed in a way not present in the drawings; for example, the extension and flexion stops can be designed to fit between the gears on either the posterior or anterior side of the hinge assembly in order to limit the range of motion of the joint.

The hinge assembly may incorporate at least one tensioning element 25 that is attached on each side of the upper and lower hinge assembly. The tensioning element stores energy when it is drawn across the hinge upon knee flexion by the wearer of the knee orthosis. The tensioning element(s) can be ported through holes in the hinges or support members and can be fixed in place in the brace on either the proximal or distal end, or both. Alternate designs are based on the needs of the user and include one or multiple tensioning elements within the hinge assembly on either or both the medial or lateral side of the knee orthosis, or above or below the hinge. These alternate designs also include bands of varying sizes or other parameters that generate different amounts of resistance. Using more than one band can be tailored to engage and increase in tension as the degree of flexion is increased. In other aspects, the tensioning element is fixed at the ankle-foot orthotic. In yet other aspects the tensioning element for the knee orthotic, 25, can be connected to at least one other tensioning element in an ankle-foot orthotic or the hip component of a Hip-Knee-Ankle-Foot orthotic, or both.

Figure 3:
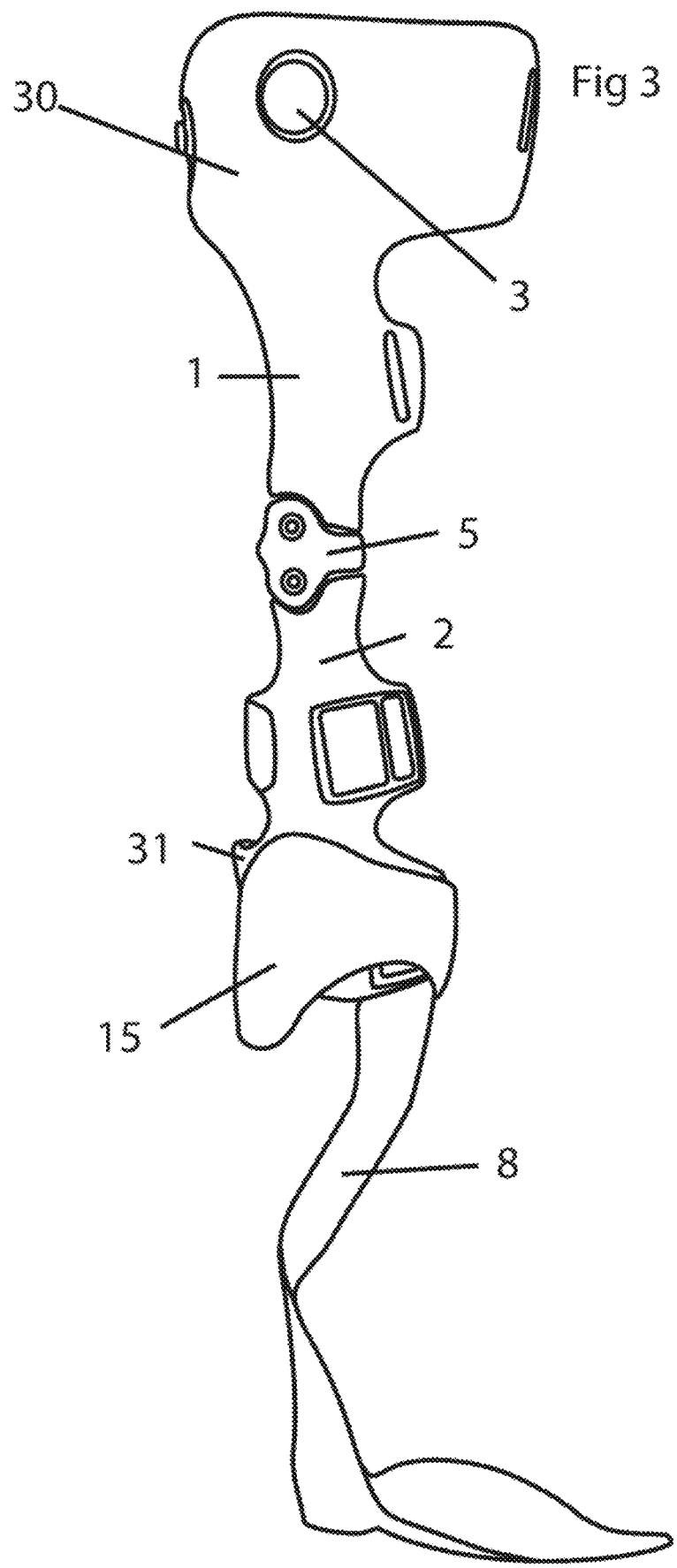
FIG. 3 is an illustration of a KAFO with a single upright knee orthotic, according to the present invention.

As seen in FIG. 3, a KAFO utilizing a single upright knee orthosis element may include a tensioning system 3. A single upright knee orthosis element may provide valgus or varus unloading support by utilizing material flexibility, rigidity, and/or strength characteristics to apply forces in the desired location(s). For example, a brace designed to treat varus to relieve medial compartment osteoarthritis may apply a lateral or medial force in the center of the brace at the hinge assembly 5. The curvature of the frames (1, 2) away from the leg will apply a medial or lateral force above and below the user's knee, resulting in a corrective or distracting force that will reduce pressure in the medial or lateral compartment.

The single upright brace frame can be comprised of a proximal frame 1 and distal frame 2 connected with a hinge assembly 5. In aspects, a combination of rigid or semi-rigid proximal and distal supports (30, 31) can be used and in aspects may be required. In aspects, the brace can be worn on the medial or lateral side of the leg. In aspects, the brace can treat varus or valgus from either the inside or outside of the leg. For the unloading variant, the tensioning element (e.g., 25 in FIG. 2) may be drawn over the hinge and tensioned using one or more elastic bands and a tension-locking mechanism 3 in FIG. 3, such as a BOA™ dial or other tension-adjusting mechanism that may be placed on the upper 1 or lower portion 2 of the frame. The brace may be contoured around the leg and patella to prevent or minimize rotation around the leg and migration down the leg with rigid or semirigid supports (30, 31). An alternative version of this brace has a fixed tensioning element. A strapping system may be incorporated into the brace frame. In aspects, an ankle-foot orthotic, 8, is connected to the lower frame 2 by a mechanical element 15 (see, e.g., FIG. 1 and FIG. 3).

An embodiment of the invention includes hinge assemblies, 5, with gears of variable radii as a means of distraction. A variable radius gear or cam is one where the distance from the pivot point to the face or teeth (the radius) changes with the angle of rotation. When employed in a polycentric hinge, the distance between axes of rotation changes with the angle of flexion/extension of the frame elements, for example, 1, 2. The proximal and distal gear radii on one side of the brace can differ from the gear radius on the other side. This means of distraction is also applicable for a single upright knee orthosis. In other embodiments, the distracting gears or cams can be employed in the ankle-foot pivot point and/or the hip pivot point of KAFOs or HKAFOs. In embodiments, the KAFO or HKAFO contains an energy storage system (either a tensioning system or compression system) in combination with a distraction hinge assembly to provide for multi-compartment or tri-compartment unloading of the knee joint. Such a multi-compartment unloader achieves force reduction in multiple compartments of the knee simultaneously through synergistic mechanisms. The energy storage system reduces force applied by the quad during extension, reducing net forces on both the patellofemoral and tibiofemoral compartments. In addition, the distraction hinge provides a force across the joint which opposes the ground reaction force, therefore providing for further unloading. Both systems can be tuned to optimize the amount of unloading of the desired compartment(s) based on the individual's need.

An embodiment of the invention includes a hinge assembly that conforms to the shape of the wearer's leg to reduce the bulk and improve aesthetics. In addition, a conformable hinge assembly may be tailored to achieve a desirable loading profile. The conforming hinge assembly may be comprised of proximal and distal gears, cam inserts, and hinge caps. The assembly may be curved to fully or partially conform to the user's joint or limb as opposed to a flat shape which will generate an increasing amount of tension per degree of flexion and the tensioning element will travel further over the cam or gear mechanism. This embodiment may or may not have an adjustable tensioning element.

In aspects, the adjustable tensioning system may be incorporated on the knee orthosis component to apply dynamic and functional forces to the straps. These tensioning systems can be applied to provide functional forces to the joint or parts of the limb, rather than just tightening the straps to fit the user. For example, the knee orthosis component may contain a strap that adjustably tightens by turning a rotary tensioning dial that attaches to either one end or both ends of the strap, and the strap attaches to either the brace or another strap. The strap can be able to gather tension and release tension by rotating the dial, releasing by pushing a button or pulling the dial. The strap may have a semi-rigid or rigid portion that partially conforms to the body part and that may distribute force on the body part when tightened. A dampening or tensioning element may be in-line with the tensioning system to achieve a more gradual onset of tension. One such use is in an ACL brace, for example.

One of many beneficial applications of a KAFO containing the adjustable tensioning system as described herein would be for patients recovering from ACL injury or ACL reconstruction. The tensioning system could be incorporated and adjusted as part of the lower portion of the knee orthosis component to dynamically apply a force to the tibia, which would increase with increasing extension of the knee, wherein a tensioning element is optionally in-line with the tensioning system so that the tensioning force is dampened.

Energy Storage Mechanism

Figure 6A:
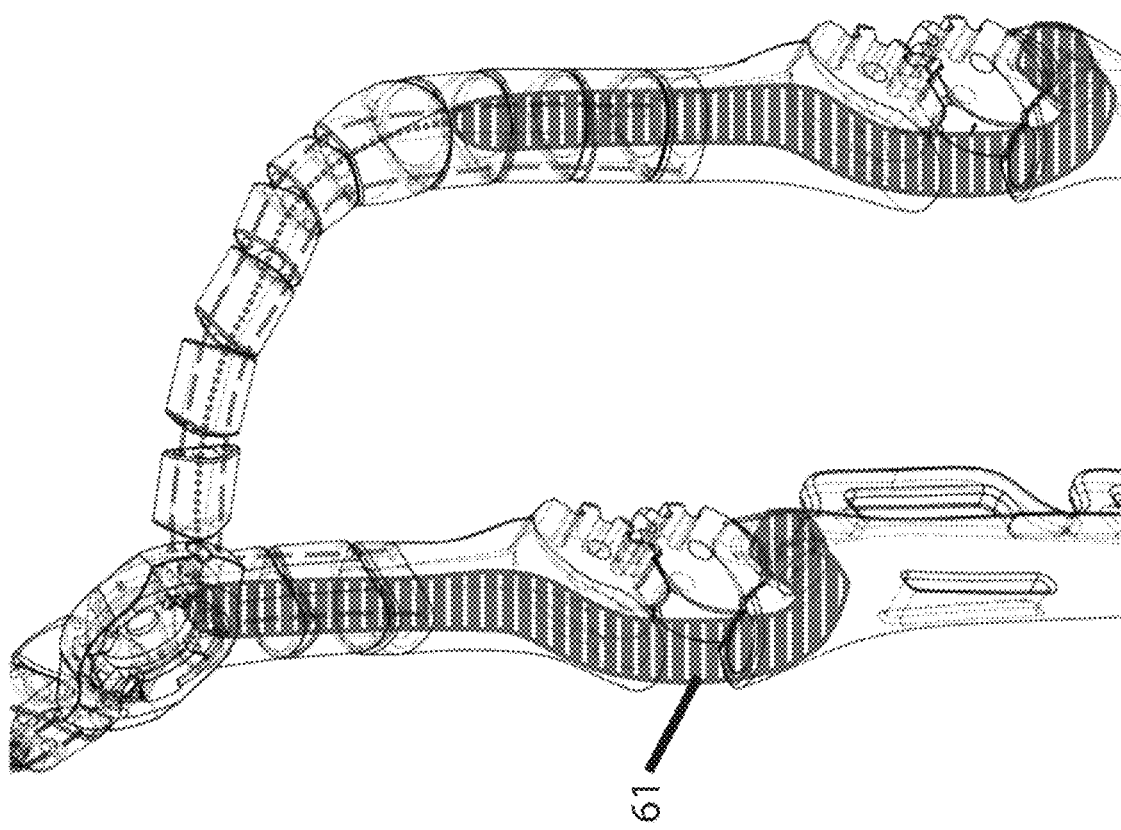
FIGS. 6a-6b are illustrations of a modular hinge and an adjustable tensioning system and exemplary components, according to the present invention.

As seen in FIG. 6a, components of the KAFO or HKAFO may contain individual or interconnected energy storage mechanisms (61), which control forces around, between or within the joint. (The energy storage mechanism may also be referred to herein as energy storage system.) Components of the KAFO or HKAFO may contain individual or interconnected energy storage mechanisms, which control forces around, between or within the joint. The energy storage mechanism may be adjustable by the user while wearing the product, or may be set to a specific setting by a professional, e.g. a doctor or orthotist. The energy storage mechanism may be a tensioning system or a compression system, or both, depending on whether the mechanism is typically under tension or compression during use. In embodiments, a tensioning system can be comprised of an adjustment mechanism, a rigid element (e.g., a cable or lace), and an energy storage element. In aspects, the energy storage element may be or comprise one or more elastic bands, springs, or liquids (e.g., pneumatic systems), and may also store and release energy in compression as well as tension. The energy storage element may be selected to have specific properties, for example a Young's Modulus that allows for discrete levels of force to be stored and applied around a given axis of the joint, such as an ankle joint. The energy storage system may be connected at one or more points to different regions of the distal portion of the orthosis component to direct force around the desired axis. The energy storage system may run across a hinge or a cam in order to generate a torque around a joint rather than providing a force between the joint.

Distracting Hinge

The KAFO may contain a distracting hinge (45) that generates a separation within either the knee, ankle or hip joint as a function of the range of motion of the joint.

Moving the effective pivot point forward or backward compared to the natural pivot point of the joint will distract or compress the joint. In the case of a traditional hinge the effective pivot coincides with the hinge pivot point. In the case of a polycentric hinge, the effective pivot point is the collective axis of rotation of the multiple hinge points.

In other aspects according to the present invention, changing the radius of curvature of the pivoting elements as a function of the angle of rotation can also provide a distraction force to unload the joint. For example, in a polycentric hinge that utilizes interlocking gears, the distance of the gear teeth from the rotation axis can be varied as described herein. As the wearer extends or flexes their joint (for example, their knee), the distance between the polycentric hinge centers changes. Depending on the gear design, the orthotic can push the joint apart in either flexion or extension, and specifically as a function of the range of flexion or extension depending on the path of the gear surfaces. To accommodate the increase in effective length of the orthotic, slots or cutouts can be placed in the gear faces, the hinge element, or both.

Keeping the gear teeth meshed when the hinge pulls the orthotic together can be accomplished by using a spring or elastic element to pull the polycentric hinge together. Alternatively, guide pins, bushings, tabs or the like can ride in recesses or cavities to help keep the gear teeth engaged at all times. If the amount of distraction is not too great, increasing the length of the gear teeth themselves (and corresponding valleys in the mating gear) can be sufficient to ensure that the two gears intermesh through the full rotation or the hinge.

Figure 4:
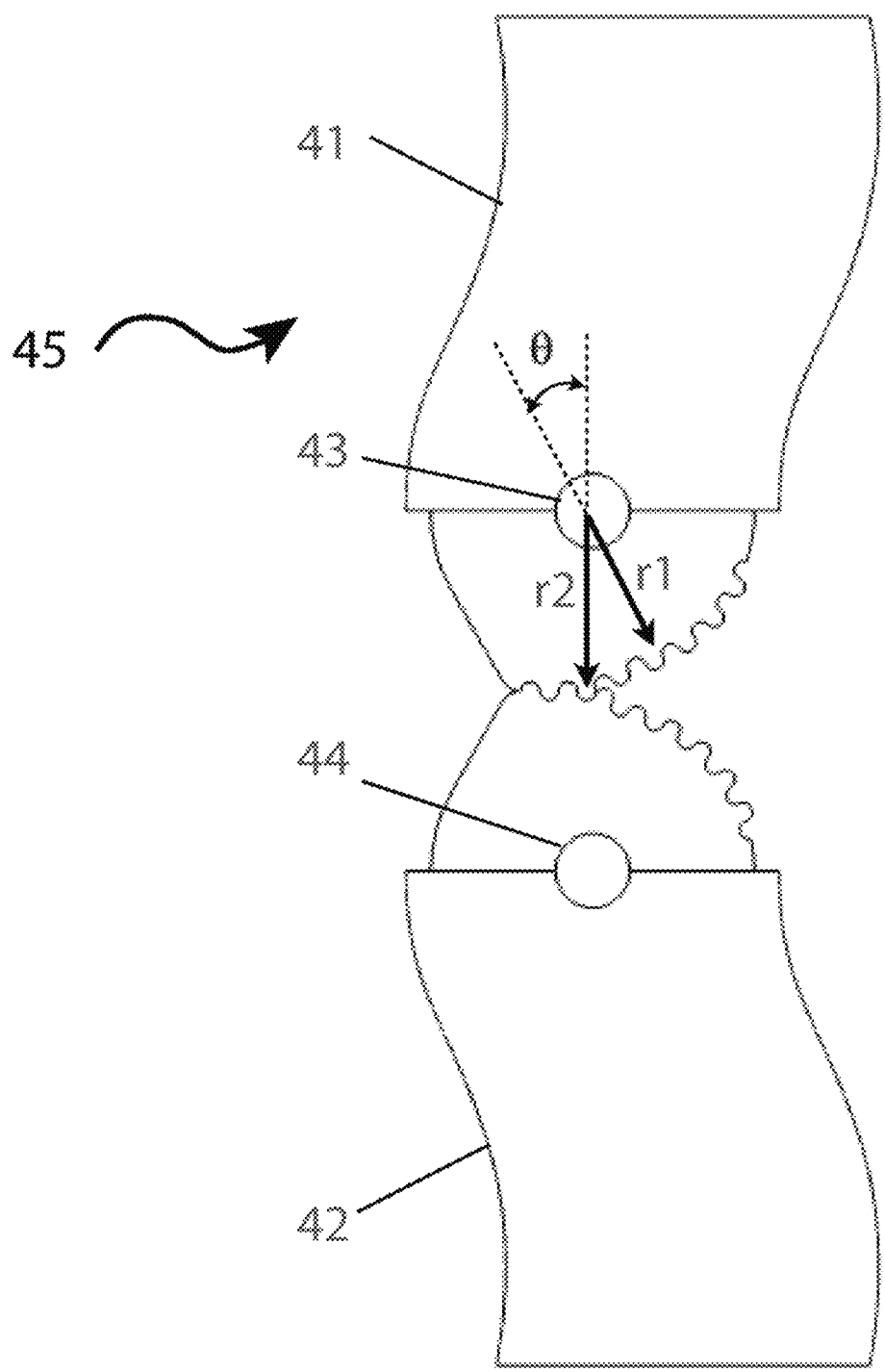
FIG. 4 is an illustration of a variable radius distracting hinge, according to the present invention.

FIG. 4 is an illustration of a variable radius polycentric distracting hinge apparatus 45. An upper arm 41 and lower arm 42 rotate around pivot points 43 and 44 respectively. The radius of the gear face is the distance from the pivot point to the face of the gear. As shown in FIG. 4, the radius, r1, of the upper arm 41 does not change from 120 to 30 degrees of flexion (which is the same as 60 to 15 degrees rotation of the upper arm 41). Leg flexion is defined as the included angle between the calf and thigh as pivoted about the knee. A total flexion of x degrees is obtained when the upper and lower leg pivot by x/2 degrees. In this manner, a flexion angle of 120 degrees corresponds to an upper arm rotation of 60 degrees. The distance from the pivot point 43 increases linearly from r1 to r2 between 15 and 0 degrees of rotation (which corresponds to 30 to 0 degrees of flexion).

Cams, ramps, wedges, gears or the like can be employed such that as the joint is flexed the two connecting arms are forced apart. The shape of the cam, ramp, wedge, gears or the like can be designed to control the amount of distraction versus angular position.

Figure 5B:
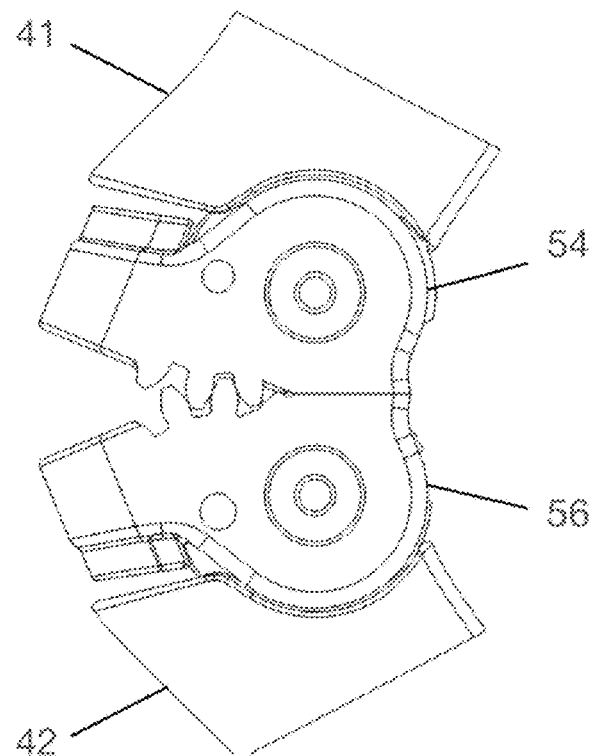
Figure 5C:
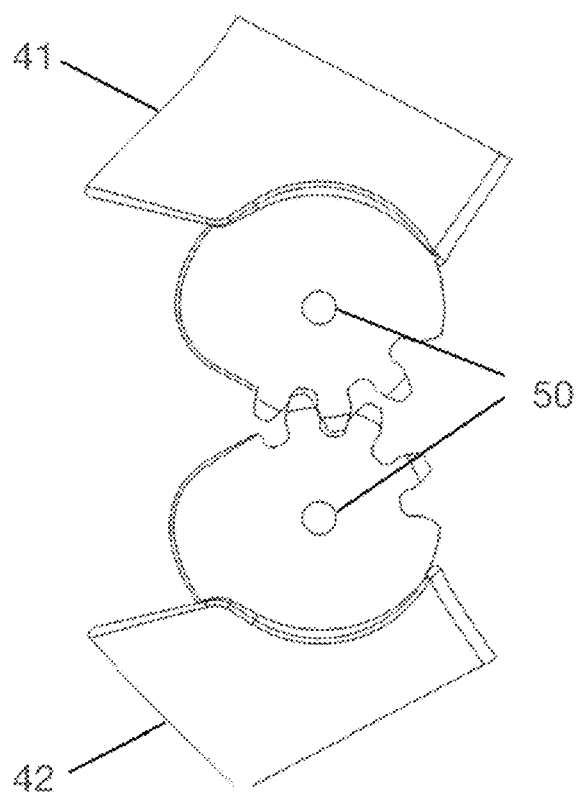

In another embodiment, a distraction hinge can be accomplished with a compound hinge, wherein there is more than one axis of rotation of the hinge, and wherein the axes of rotation are not co-axial. FIG. 5a shows an example of a two-axis hinge. The hinge rotates about pivot point 50 from 120 to 30 degrees. From 30 to 0 degrees the hinge rotates about pivot point 52. Because the two pivot points are not co-axial, there is a net vertical, y, and horizontal, x, distraction. In the example shown in FIG. 5b, the polycentric hinge elements 54, 56 and the upper and lower arms 41, 42, use gear teeth to keep the upper and lower arms in synchronous motion. The gear teeth pitch or module can be the same, as shown in FIGS. 5a and 5c for the two pivot points, or they could be different.

Further, FIG. 5a shows the orientation of a multi-axis hinge at 0 degrees of flexion. The hinge elements 54 and 56 (as shown in FIG. 5a) are engaged and the upper and lower arms are rotating about the axes of rotation 52 (as shown in FIG. 5a). FIG. 5b shows the orientation of a multi-axis hinge at 45 degrees flexion. Both sets of gears, the hinge elements 54 and 56 (in FIG. 5b) and the upper and lower arms 41, 42 (in FIG. 5b) are engaged. FIG. 5c shows the same orientation as FIG. 5b with the hinge elements 54 and 56 removed for clarity. In FIG. 5c, the engaged gears of the upper and lower arms 41, 42 are clearly shown. Increasing the angle of flexion now occurs around the pivot points 50.

The total amount of distraction is determined by the formulii:

$$Dx = Xoffset * \cos(theta) - Yoffset * \sin(theta) - Xoffset$$

$$Dy = 2 * [Yoffset * \sin(theta) + Yoffset * \cos(theta) - Yoffset]$$

Where Xoffset is the distance along the x-axis from the pivot point 50 to pivot point 52 (see FIG. 5a), Yoffset is the distance along the y-axis from pivot point 50 to pivot point 52 and theta is the angle at which the distraction begins. In FIGS. 5a-5c the distraction starts at 45 degrees of leg flexion, by way of example only.

Various means can be employed to keep the complex hinge in sync through its range of motion. Stops or catches can be employed that catch and release as the arms rotate through their range of motion. Elastic elements can compress the gear faces together.

The distraction hinge brace may be used to unload part of a joint postoperatively or post injury to improve healing and limit risk of reinjury. For example, it would be beneficial for a patient recovering from procedures such as a cartilage transplant (osteochondral allograft) or MACI procedure, during a range of motion, while also limiting flexion and extension so that injured part of the joint remains protected.

The brace can use a patellofemoral unloading system as described herein, combined with a distraction hinge that separates the tibiofemoral compartment to the desired amount. This type of brace can be more generally applied to other joints like the ankle, hip or elbow. A back brace or a neck brace may use similar distraction hinges where two components push against each other during articulation, resulting in a distraction or compressive force.

In other embodiments, the distraction brace may or may not articulate at the hinge in order to create a distraction force pushing away from the joint center. For example, a manually or electronically controlled telescoping brace frame could generate a distraction force by adjusting the length of the vertical members of the upper and/or lower portions of the knee orthosis component or of an AFO component. The mechanism may be extended or retracted using an adjustable dial while the user is wearing it. The telescoping mechanism can allow segments of the brace frame to collapse or slide within each other in order to increase or decrease the length of the overall portion of the brace. The mechanism may be further controlled by a series of motors, pistons, springs, elastomers or pneumatic systems, which control the amount of distraction. The amount can be controlled by the user, automatically based on sensory data, follow a preset program, or controllable in near- or real-time using a computer or mobile device application, or an interface (e.g., buttons) on the device itself. The brace itself may be powered using a battery contained on or within the device, which may be chargeable or replaceable.

The distracting brace mechanisms described may be used as a treatment for knee OA, pain relief, post operative or post injury recovery. The brace may be modified to distract different parts of a joint selectively or altogether, for example a knee joint may have both the tibiofemoral joint (medial and lateral compartments) distracted, or only one compartment, depending on how force is applied. The distraction hinge may distract using gears or components with variable effective radii, or may have different "gearing" wherein the range of motion utilizes a different gear pitch at a different degree of flexion or extension.

In another example, a medial or lateral force can be applied as a function of the range of motion of the hinge in order to unload the opposing tibiofemoral compartment of the joint. A hinge that provides displacement along the ML axis of the knee joint at a certain range of flexion could, in aspects, be comprised of a system of ramps which can be used to push off of each-other to generate an outward force, which may be used in "unloader" braces to apply a medial or lateral force between the hinge of the brace and the knee condyle. This configuration can be used on other body parts where pressure needs to be applied in correspondence with joint movement.

Any of the described exemplary distraction hinge embodiments, or any embodiments that would be deemed substantially equivalent by one skilled in the art, may be incorporated at any point in the KAFO or HKAFO. The distraction hinge may be present between the upper and lower portions of a hip orthosis component, between the upper and lower portions of a knee orthosis component, and/or between the upper and lower portions of an ankle-foot-orthosis component. The distraction hinge mechanism may be engaged or disengaged by the user or an orthotist, either during fabrication, during an adjustment, or while the user is wearing or using the joint brace. Similarly, while the mechanism may be turned on or off, it may be dynamically adjusted by the professional or the user. For example, in the embodiment of the dual pivot point distracting hinge, the gear centers of one of the articulating gears may be shifted to adjust the amount of joint distraction. Alternatively, the gears' radii may be adjusted by interchanging gears or adding/removing a component or material to the gear itself.

One skilled in the art would understand that the distraction hinge mechanisms described for the knee, hip, or ankle, as described herein, may be similarly applied to provide joint separation in other joints or body parts, such as the toes, shoulder, elbow, wrist, back, neck, or fingers, just by way of example.

Ankle-Foot-Orthosis Component

Figure 7:
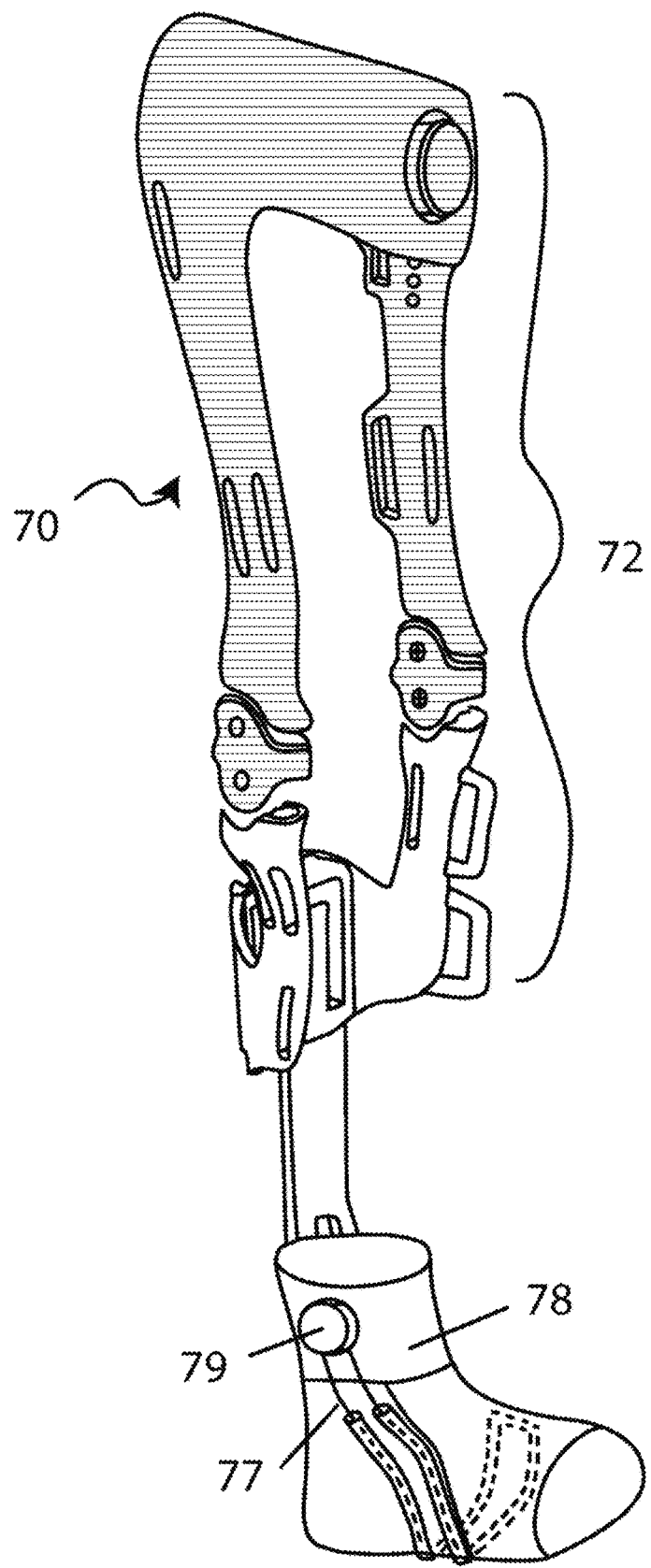
FIG. 7 is an illustration of a KAFO containing a multi-axis rotational control ankle foot orthosis (AFO), according to the present invention.

Embodiments of this invention comprise a KAFO 70 with a multi-axis rotational control ankle-foot orthosis (AFO), 78, as seen in FIG. 7, wherein the direction and amplitude of force can be controlled around, for example, 3 axes of the ankle joint through adjustable energy storage systems in tension or compression; rotational control is also envisioned in one axis of the ankle joint and two axes of the ankle joint. Embodiments comprise a KO component 72 connected to an AFO component 78, which is further comprised of a proximal portion and a distal portion, where the proximal portion is anchored above the ankle joint and optionally houses an adjustment mechanism 79. The proximal portion is connected to the distal portion by tensioning or compressive elements 77 through which forces can be controlled by the user via the adjustment mechanism. In other embodiments, the AFO component is comprised of one continuous mesh, sock, or sleeve, through which tension can be controlled by the user. In embodiments, the device is personalized to the user through multiple aspects including user-enabled adjustment of forces around the joint.

The AFO component may be comprised of a rigid or semi rigid proximal portion, a rigid or semi-rigid distal portion, an energy storage element connecting the proximal and distal portion, and an adjustment mechanism by which the user can control the force within the energy storage element. For example, a tensioning system connected to the medial side of the foot would prevent eversion while a tensioning system connected to the lateral side of the foot would prevent inversion. In this way, the device is modular and tunable to the specific user's need.

The energy storage element, for example an elastic band, may have different geometries to control the properties, amount of force applied, and positioning around the ankle joint, and may be in the form of a band or a web with properties based on the specific cross-sectional geometry. Rather than a rigid distal member 8 as shown in FIG. 1, the AFO component may be comprised of a sleeve or sock to which the tensioning system can be attached in many positions or orientations to direct the applied force under tension. In some embodiments, the tensioning system of the AFO component may be controlled automatically using a motor, which may be further activated by sensors in any part of the KAFO/HKAFO. One skilled in the art would understand that the multi-axis rotational control mechanism described for the ankle may be similarly applied to provide or control rotational forces in or around other joints or body parts, such as the knee, hip, shoulder, elbow, wrist, back, neck, toes, or fingers, just by way of example.

Hip Orthosis Component

Figure 8:
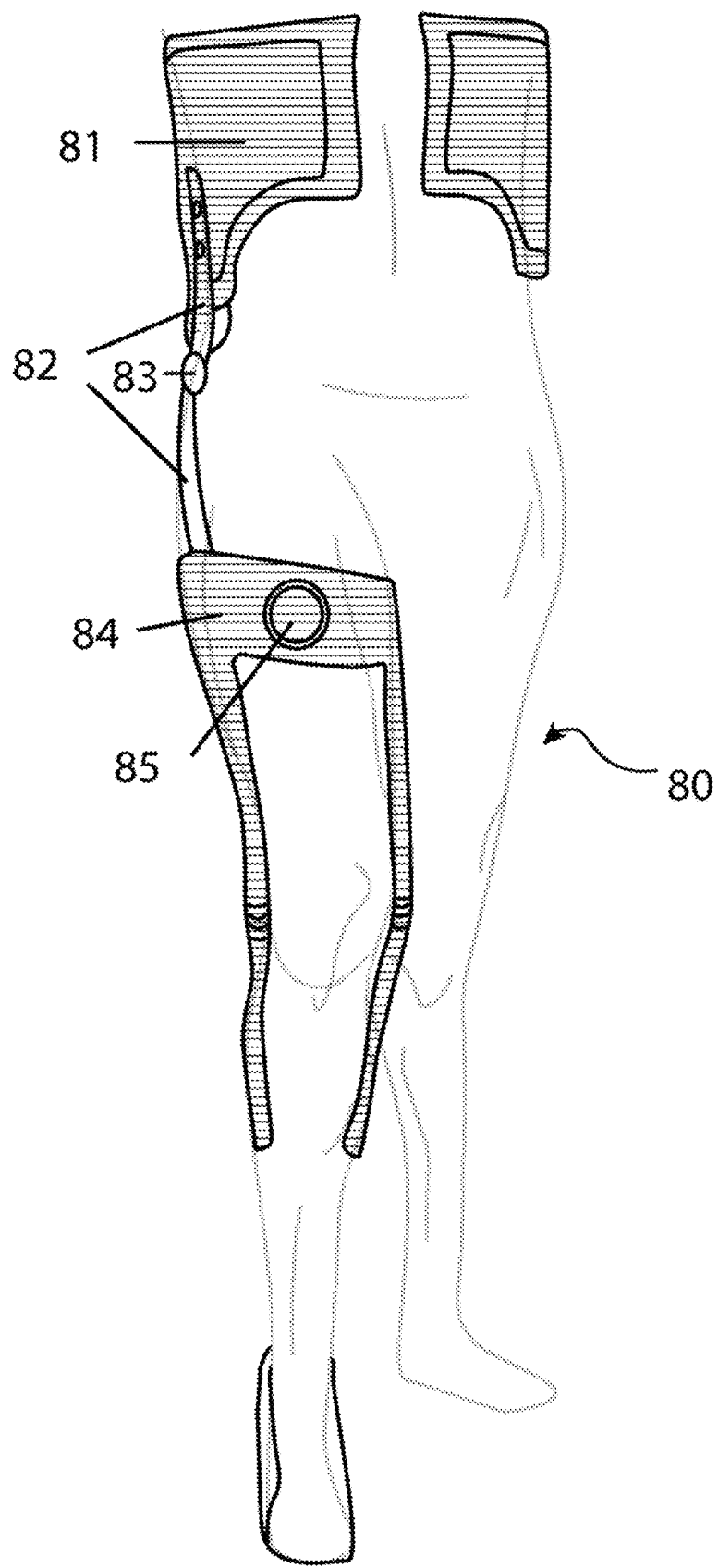
FIG. 8 is an illustration of a hip knee ankle foot orthosis (HKAFO) containing an adjustable tensioning system, according to the present invention.

Embodiments of this invention comprise a HKAFO 80, which may contain a separate or interconnected tensioning system in the hip orthosis component as seen in FIG. 8. The hip orthosis component can be comprised of a rigid or semi-rigid upper portion or belt 81, a rigid or semi-rigid lower portion 84, and connected by an energy storage system 85 in either tension or compression. The hip orthosis may optionally contain a hinge 83 and a vertical support 82. The energy storage system can be comprised of an adjustment mechanism, cable or lace, and optionally an energy storage element as described herein. The energy storage element can be any of the materials or components described previously in the KO or AFO tensioning systems herein, just by way of example. The energy storage system may apply a force between the upper and lower portions on more than one side of the hip to provide a compressive force on the hip, therefore preventing dislocation of the femur from the hip socket. Alternatively, the tensioning system may apply a force around one axis of the hip joint in combination with the hinge in a mechanistically similar fashion as the KO hinge described herein. Such an embodiment would provide for swing-assist of the hip joint, and may be used in combination with swing assist mechanisms in the knee and/or ankle joints.

Interconnected Energy Storage Systems

Figure 9:
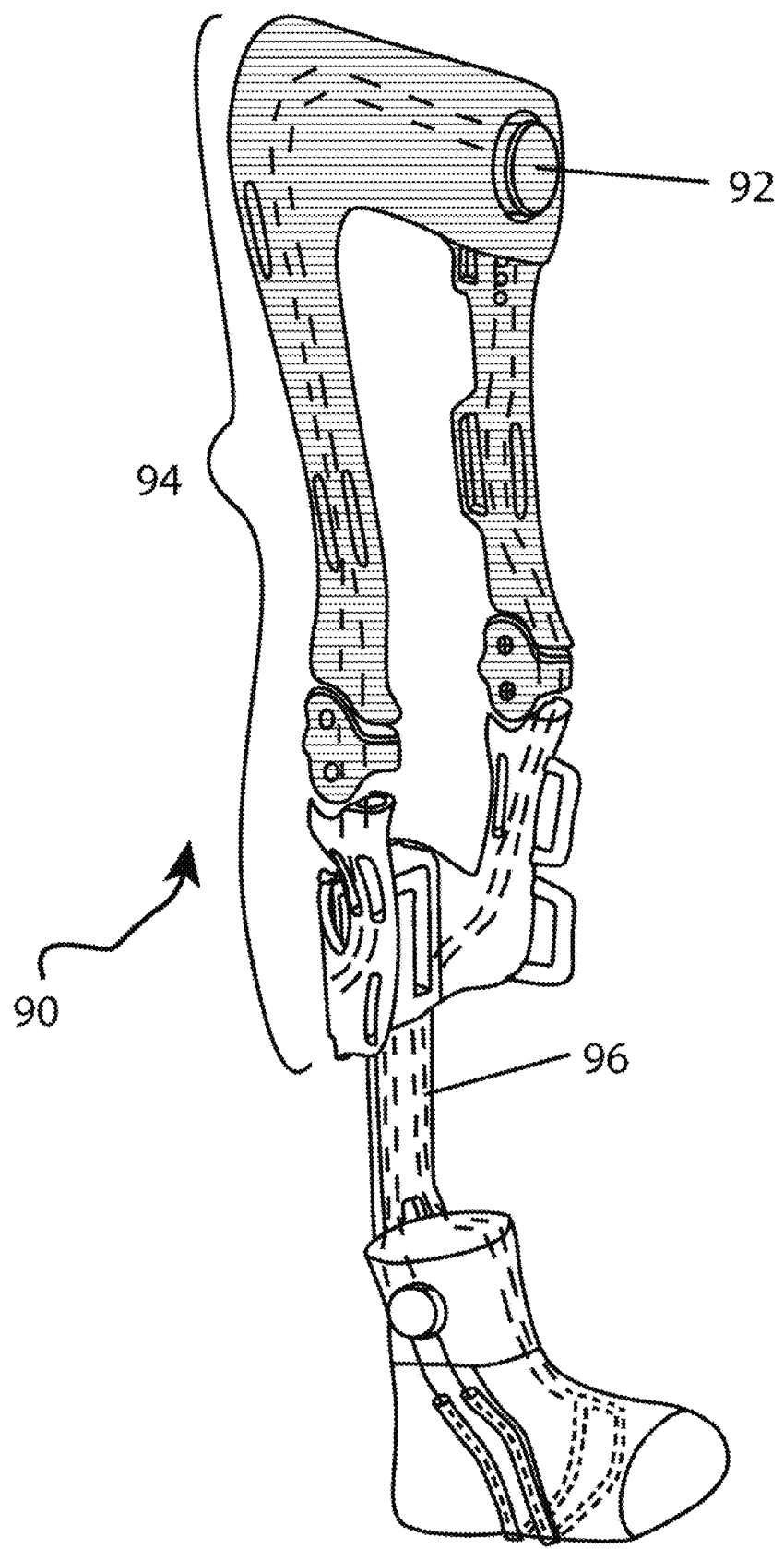
FIG. 9 is an illustration of a KAFO containing an integrated adjustable tensioning system that runs between the knee orthosis and AFO components, according to the present invention.

In embodiments, the tensioning systems of the HO, KO 94, and AFO may be interconnected as shown by the dashed lines 96 in FIG. 9. As shown, the KAFO 94 contains a tensioning system 92. It will be apparent to one skilled in the art based on the invention described herein that the individual tensioning systems, embodiments and applications described in each of the KO, AFO, and HO components could be combined in whole or in part in a continuous or semi-continuous system, as well as combinations of systems. In other embodiments, only one component may contain an active tensioning system. In other embodiments, one or more components may contain an adjustable tensioning system while other components may have a static tensioning system, for example a system where an elastic band is anchored on both ends and is not adjustable but provides a variable force depending on the range of motion of the joint.

The HKAFO may also comprise or be connected to a back support or back orthosis.

Modularity and Adapter Mechanisms

In embodiments, the KAFO or HKAFO is manufactured as a continuous unit. Other embodiments of the invention contain an adaptor mechanism, which connects the hip orthosis, KO, and AFO components together into one functional device. The adaptor mechanism is designed such that the initial fit and function of the individual orthosis components are maintained. In some cases, the connection of the devices via the adaptor mechanism is meant to be reversible; that is, for example, the AFO could be detached from the KO after an ankle injury has healed. In other cases, the connection may be permanently secured; for example, glue could be additionally used when attaching a lower limb prosthetic to an unloading knee orthotic via the adaptor mechanism. The adaptor mechanism can be designed to allow for modularity of the device: where different HO, KO, and AFO components can be selected based on the patient's need and component availability.

Figure 10:
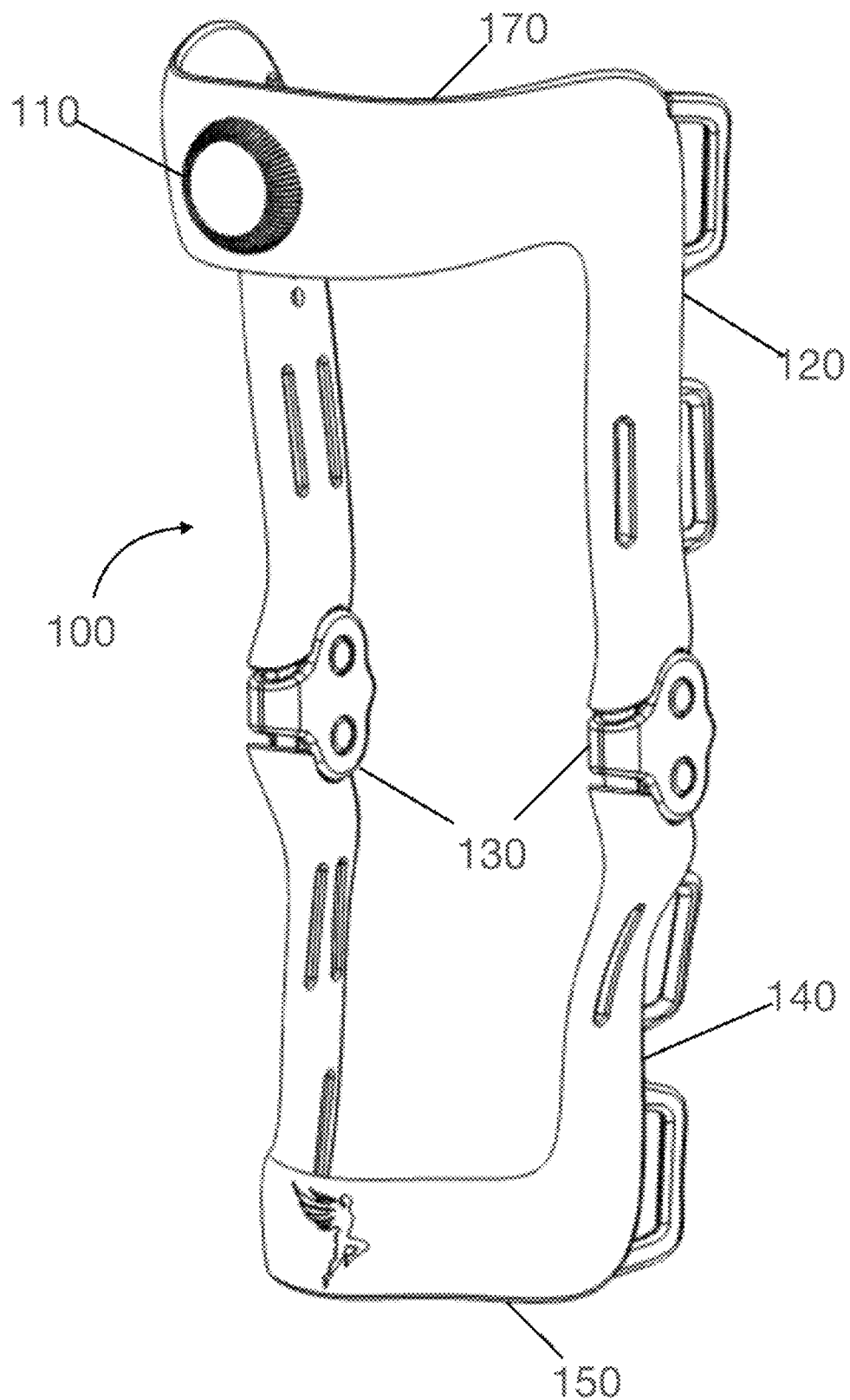
FIG. 10 is a depiction of an anterior view of an example of an adjustable tensioning unloading knee orthosis, according to the present invention.

FIG. 10 is an anterior view of an example of an adjustable tensioning unloading knee orthosis 100. This knee orthosis has an upper frame element 120 and a lower frame element 140 connected by an adjustable tensioning system (110) and hinge caps (130). Forces from the tensioning system are applied to the wearer's upper and lower leg (i.e., above and below the knee, respectively) via frame cuffs (150, 170) and straps (not shown) to provide stability and unload the wearer's weight off the knee joint.

An example of an AFO is the XTERN™ manufactured by TurboMed™ Orthotics. This ankle-foot brace is used to manage drop foot deficiencies. The XTERN™ has a lower leg holder that secures to the wearer's calf via a flexible cuff and strap, a lower leg strut, and a foot strut that wraps around the outside of the wearer's shoe. The lower leg strut and foot strut are flexible and apply a lifting force to an attachment point on the wearer's shoe that helps return the foot to the dorsiflexion position.

The XTERN™ lower leg holder and adjustable tensioning unloading knee Orthosis™ lower leg cuff/straps can be positioned such that they would interfere with each other on a typical wearer's lower leg. Yet both the XTERN™'s lower leg holder and adjustable tensioning unloading knee Orthosis™'s lower leg cuff/straps are essential for the proper transfer of forces to control the wearer's drop foot and unload the wearer's knee joint, respectively.

The XTERN™'s lower leg strut is detachably connected to the lower leg holder using a dovetail-like mechanical attachment system.

Figure 11:
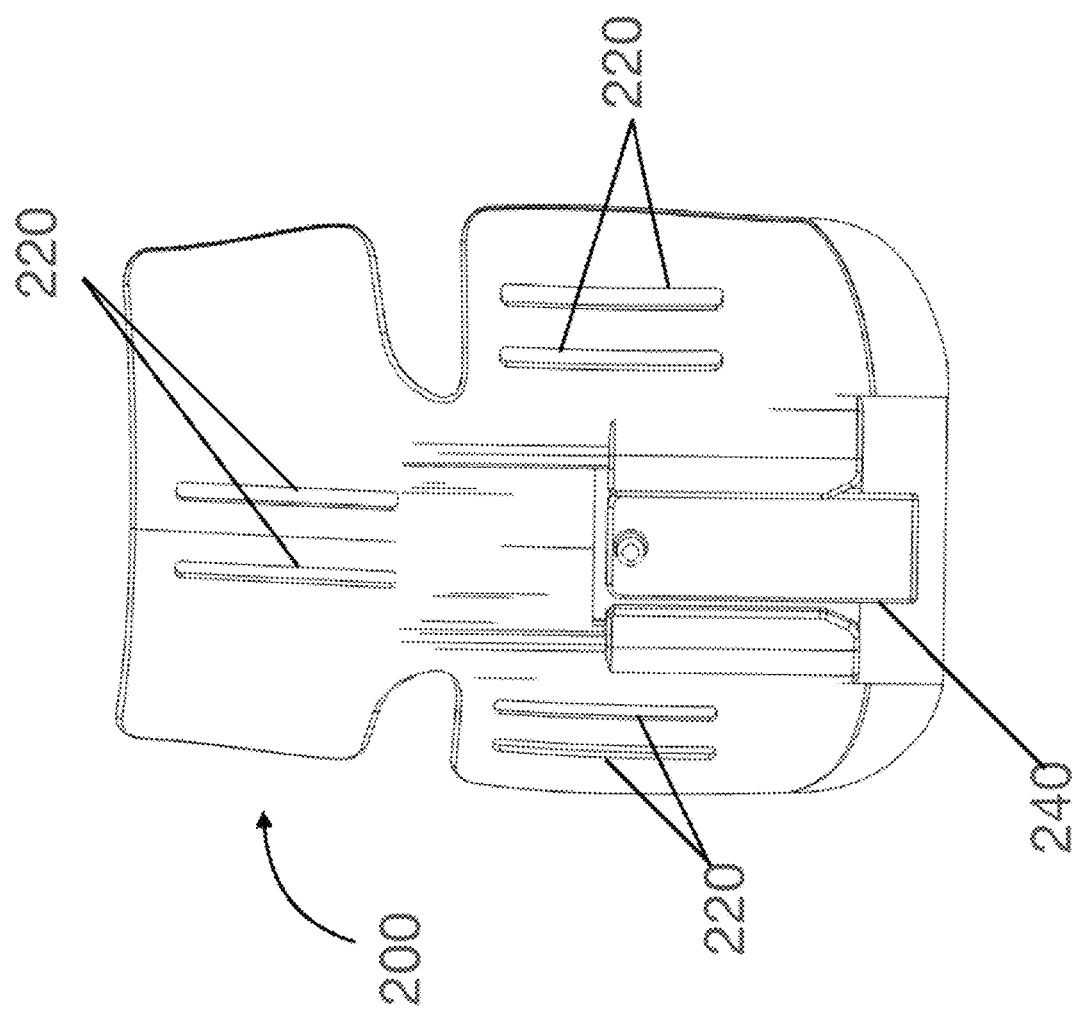
FIG. 11 illustrates an attachment mechanism(s) to combine the knee orthosis component with the ankle foot orthosis component, or the hip component with the knee orthosis component, according to the present invention.

FIG. 11 shows a lower load distribution (200) pad configured to attach to a knee orthosis's lower frame element (140 in FIG. 10) straps via strap slots (220). A lower load distribution pad is optionally employed with an Ascender™ brace (Ascender™ brace used as an example of a knee orthosis component only) to distribute the forces transferred from the lower frame element to the wearer's leg to improve the comfort and security of the orthotic. The lower load distribution pad can be worn on the posterior of the wearer's lower leg (the calf). Thus, its position on the wearer's calf can be situated to secure the lower leg strut of the XTERN™ ankle-foot orthotic. By incorporating a dovetail-like mechanical slot (240) that is dimensioned to accept the XTERN™'s lower leg strut, it is possible to provide the wearer the full functional benefits of an unloading knee orthotic and the XTERN™ drop-foot control ankle-foot orthotic at the same time.

Figure 12:
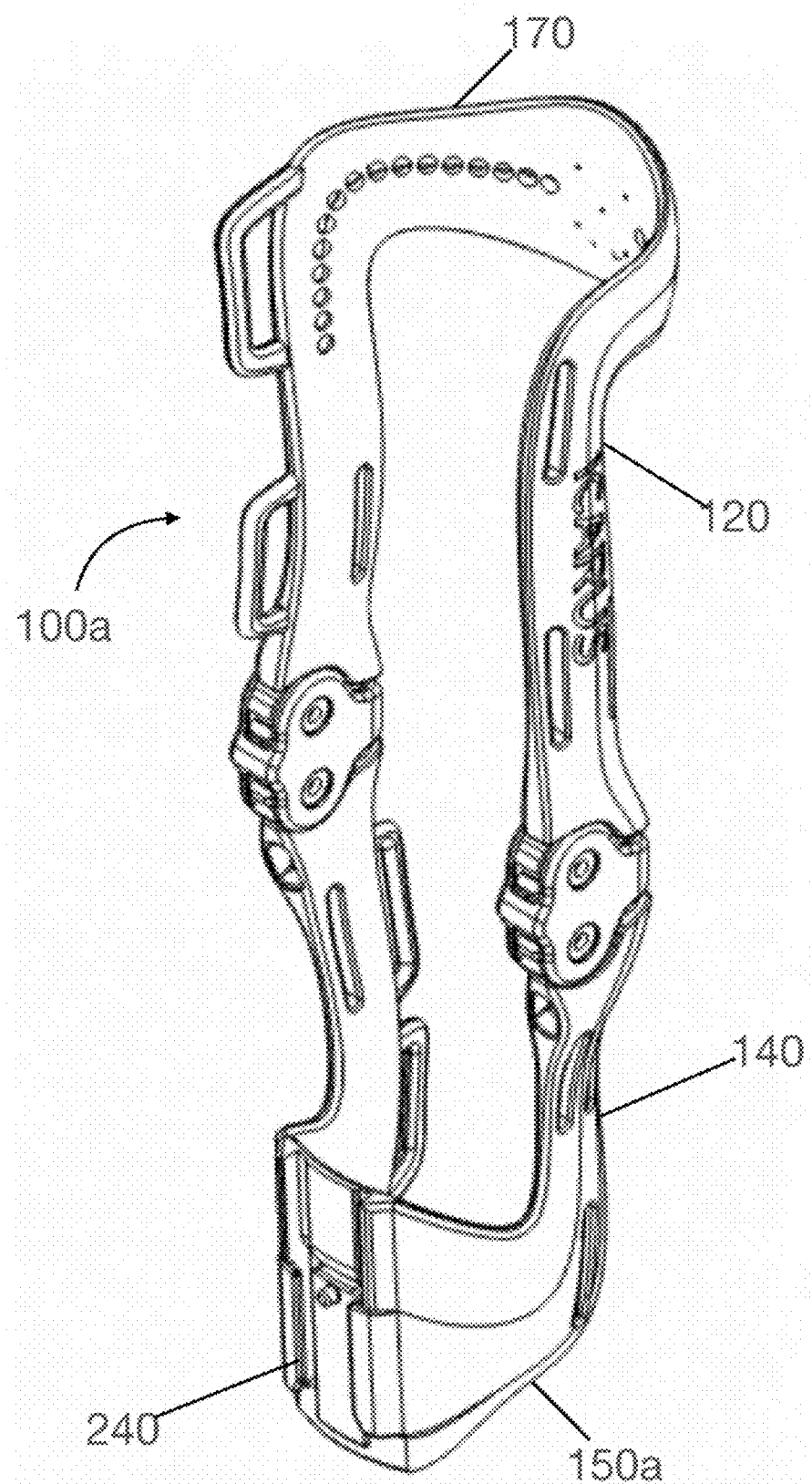
FIG. 12 illustrates an exemplary attachment mechanism(s) to combine the knee orthosis component with the ankle foot orthosis component, or the hip component with the knee orthosis component, according to the present invention.

Alternatively, the dovetail-like mechanical slot for the XTERN™ can be incorporated directly in the lower frame element of a variant of an adjustable tensioning unloading knee orthosis. FIG. 12 shows the posterior view of an unloader knee orthosis variant (100a) with an upper element (120) and a lower element (140). In this variant, the lower frame element leg cuff (150a) wraps around the calf of the wearer while the upper frame element leg cuff (170) is unchanged and wraps around the anterior thigh of the wearer. A dovetail-like mechanical slot (240) designed specifically for the dovetail-like shaped lower leg strut of the XTERN™ ankle-foot orthotic is incorporated into a knee orthosis lower cuff (150a).

In this example, the lower leg cuff (150a) mimics the function of the XTERN™ lower leg holder by securely attaching the lower leg strut to the wearer's calf. The dovetail-like attachment allows the length of the XTERN™ to be adjusted in the same fashion as the XTERN™ lower leg holder. The lower leg cuff (150a) also securely and comfortably holds the knee orthosis to the wearer's lower leg enabling the unloading function of the knee orthotic.

The examples shown in FIGS. 11 and 12 are specific to the XTERN™ drop-foot AFO and are not meant to be limiting. Other ankle-foot orthoses are known in the art that provide other functions such as the Re/aktiv™, the ExoSym™, the STEP™ manufactured by Neofect™, and the like. The dovetail-like mechanical attachment shown in FIGS. 11 and 12 would need to be replaced with another mechanical attachment system suitable to different brands/style of ankle-foot orthotic. This mechanical attachment mechanism could include a clip, buckle, or toggle that mates with an existing slot, cable, or post on the AFO component. The KO portion may also feature a slot, channel or groove in its lower portion that can securely couple to the distal upright of the AFO. Furthermore, a rivet, bolt, pin, or snap could connect the KO and AFO through overlapping holes present on both components or through a peg-slot lock, both allowing for angular adjustments during connection. Similarly, a post and hole, dowel joint, or threaded rod can be used to bond the structural elements. Adhesive, glue, epoxy, double sided bonding tape, thermosetting compounds or thermoplastic bonding film could be used to bond structural elements of the KO and AFO with no preexisting attachment features. A strap, lace, braid, or belt system that passes through a slot, buckle, D-ring, guideway or combinations thereof in the KO and AFO can be used to secure either the KO and AFO together or each to the wearer's leg. Lastly, an intermediate component could be permanently or temporarily joined to the KO and/or the AFO. This intermediate component can be used to set proper spatial orientation/distribution between the KO and AFO. An example of this piece would be a rigid element contoured to the back of the wearer's leg from the KO to AFO components.

If the desired AFO is known in advance, the attachment means can be designed directly into the brace as shown in FIG. 12. Although this is an elegant solution, it may not be readily possible to change the brand/style of the AFO once the knee orthosis has been fabricated.

Figure 13A:
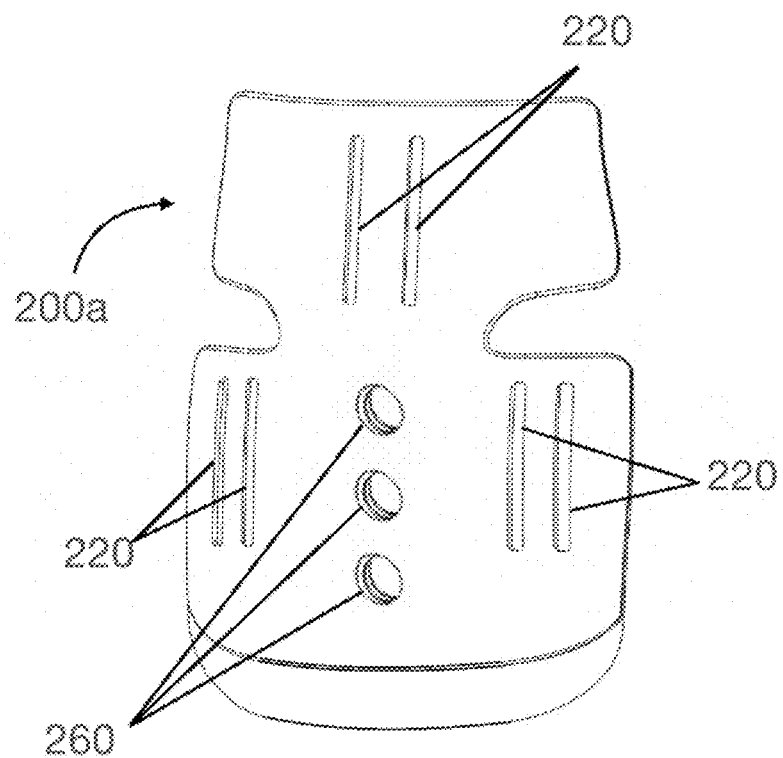
FIGS. 13a-13b illustrate exemplary attachment mechanism(s) to combine the knee orthosis component with the ankle foot orthosis component, or the hip component with the knee orthosis component, according to the present invention.

Alternatively, a generic or universal adapter could be employed such as the one shown in FIG. 13a.

In FIG. 13a, the dovetail-like mechanical attachment, of the lower load distribution pad (200a), has been replaced with a generic fastening mechanism shown as three threaded holes (260). (The three threaded holes are for illustrative purposes only. A different number of holes and/or other attachment mechanisms, or combinations of other mechanisms could be used, as described herein.)

Figure 13B:
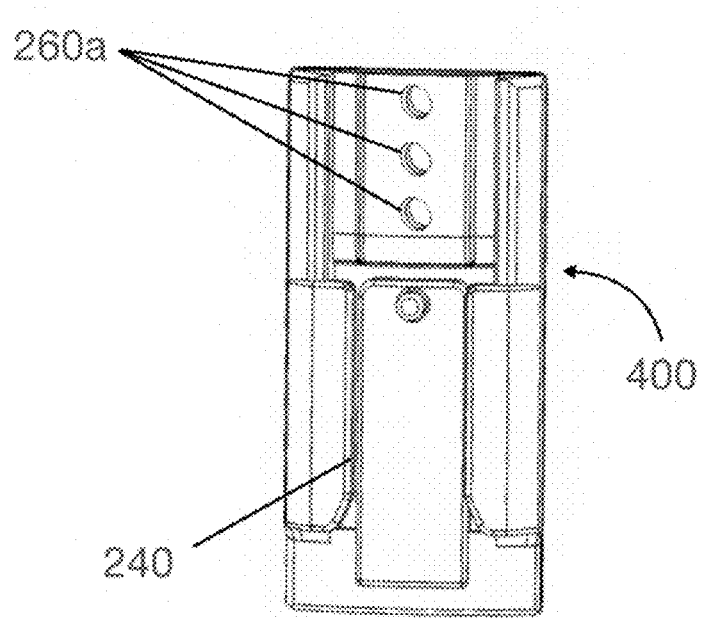

FIG. 13b shows a corresponding coupling mechanism (400). The coupling has three threaded holes (260a) to mate with the three threaded holes (260) of the lower load distribution pad of FIG. 13a and an XTERN™ lower leg strut via the dovetail-like mechanical slot (240).

This generic or universal coupling system would also be useful when directly incorporated into a KO such as an Ascender™ brace. The KO could be custom made to fit a particular wearer and would be adaptable—within limits, in aspects—to allow connection to any future AFO by means of an appropriate coupling/connection mechanism.

Figure 14:
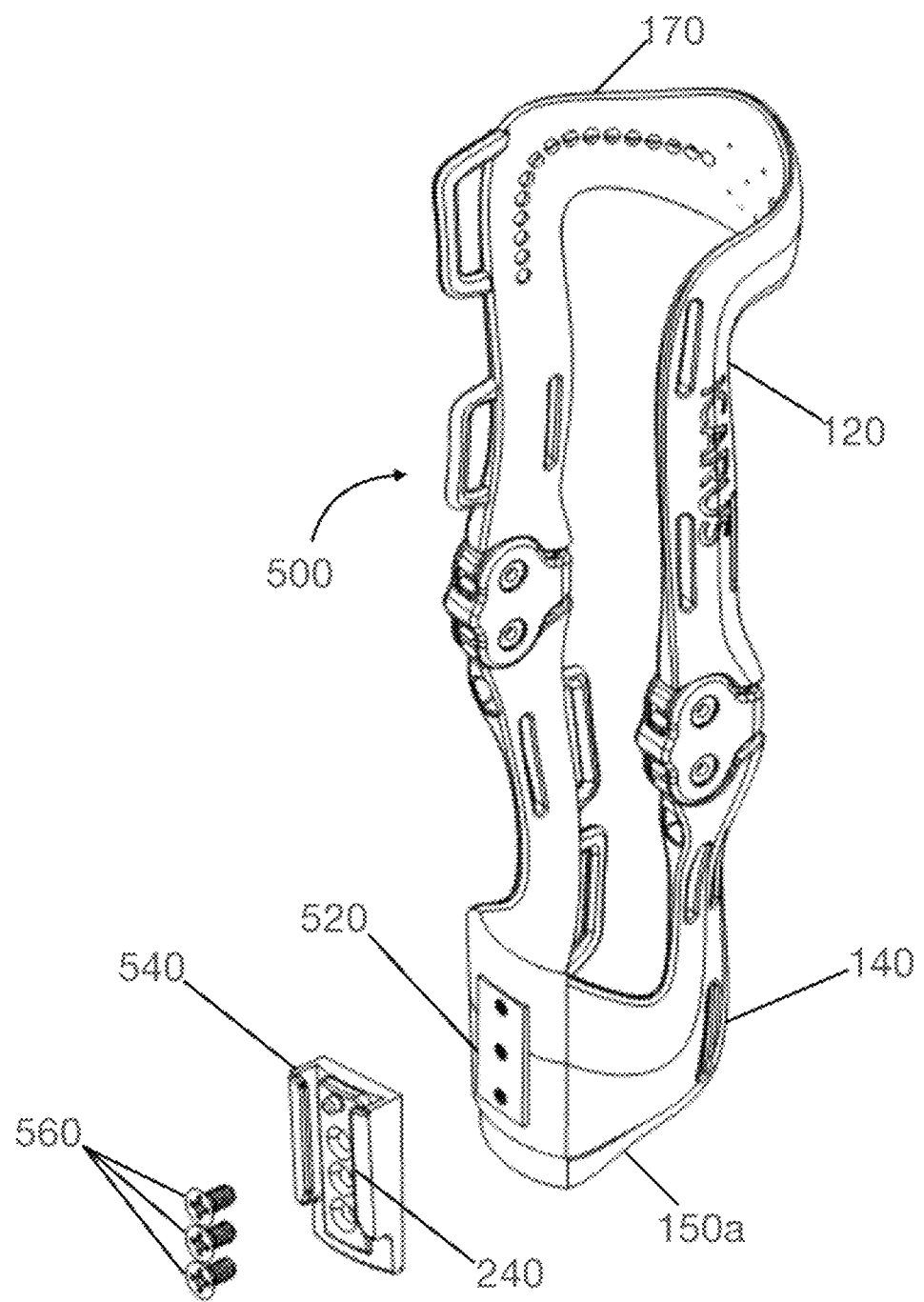
FIG. 14 illustrates exemplary attachment mechanism(s) to combine the knee orthosis component with the ankle foot orthosis component, or the hip component with the knee orthosis component, according to the present invention.

FIG. 14 is a modification of an adjustable tensioning unloading knee orthosis variant (100a) shown in FIG. 12. In this embodiment (500), a universal coupling system (520) has been manufactured into the lower frame element (140) leg cuff (150a). By way of a non-limiting but illustrative example, the attachment system shown is three threaded holes for the three screws (560). A coupling element (540) mates with the attachment system (520) of the knee orthosis variant (500) and the dovetail-like mechanical slot (240) for an XTERN™ drop-foot AFO. FIG. 14 also shows an upper leg frame element (120) and upper cuff element (170).

By changing the mechanical features of the coupling element (540) it is possible to securely connect a wide variety of AFOs to a variable tensioning unloading knee orthosis component, like an Ascender™ orthotic.

Figure 15:
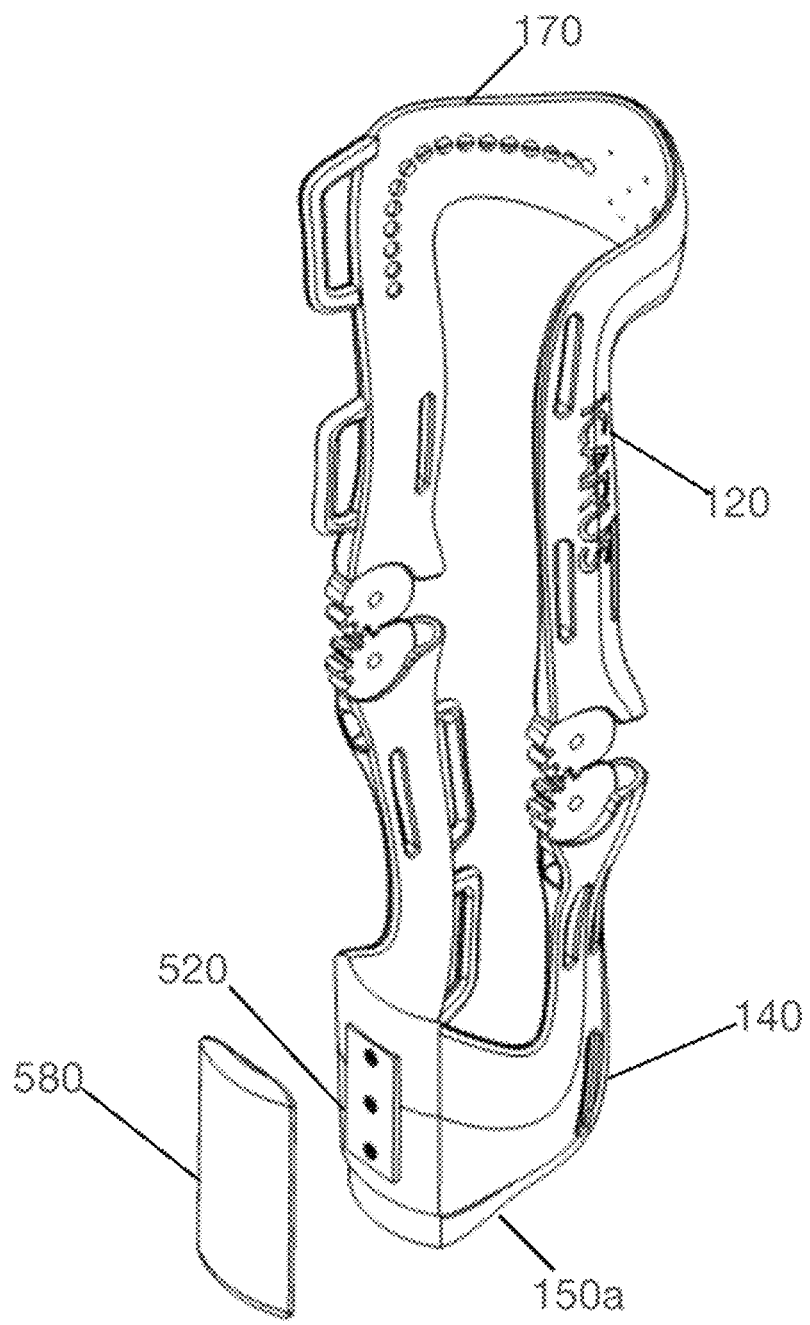
FIG. 15 illustrates exemplary attachment mechanism(s) to combine the knee orthosis component with the ankle foot orthosis component, or the hip component with the knee orthosis component, according to the present invention.

In some cases, but not all, when no coupling element (540) is attached to the universal coupling feature (520), it may not be visually appealing and could possibly detract from the overall aesthetic of KO or other orthotic. In addition, in the embodiment shown in FIG. 14, the sharp edges on the back of the lower leg cuff (150a) could catch on objects (e.g., chairs or seats) in an objectionable way to the wearer. It would be preferred, in embodiments, to have a non-functional cover (580) as shown in FIG. 15 with blind fasteners for the universal coupling feature that blends with the lines or other elements of a knee orthotic component. This could enable all Ascenders™ or other knee orthotics to be equipped with a universal coupling feature for future use—if and when—such a coupling was needed. (Other element numbers in FIG. 15 identical to FIG. 14.)

Figure 16A:
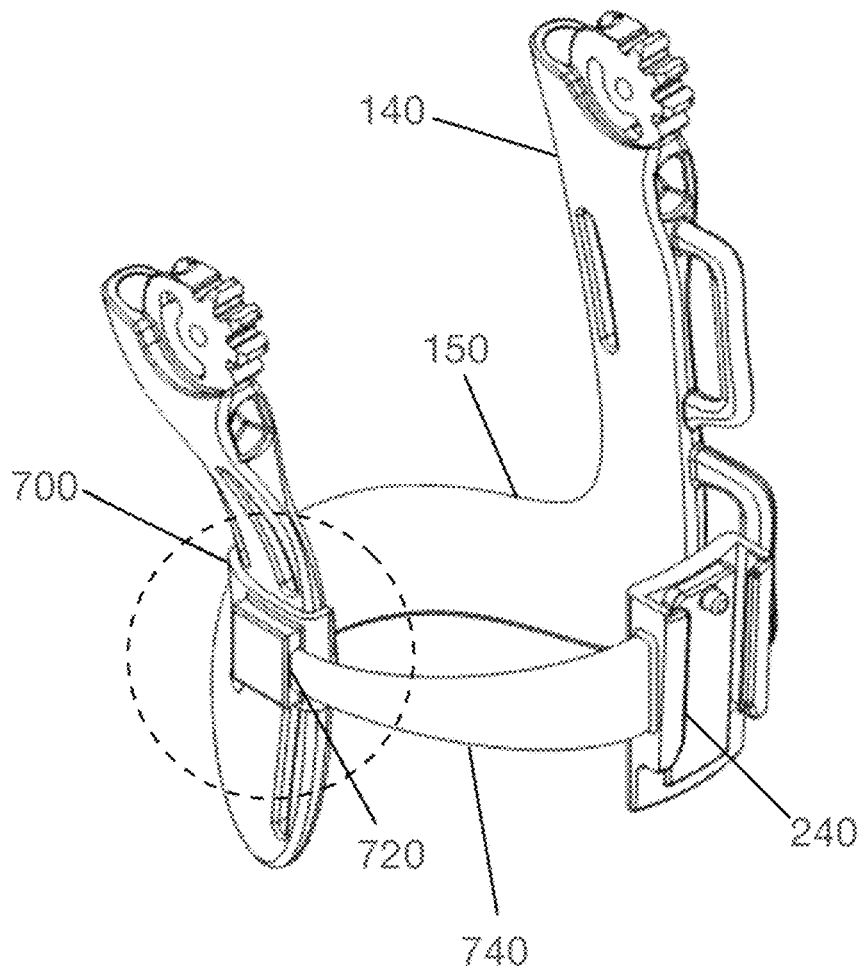
FIGS. 16-16b illustrate exemplary attachment mechanism(s) to combine the knee orthosis component with the ankle foot orthosis component, or the hip component with the knee orthosis component, according to the present invention.

FIG. 16a shows an alternative embodiment positioned on the lower frame element (140) of an Ascender™ KO or other knee orthotic. The universal attachment system in this embodiment is a low-profile clamp (700). (FIG. 16a shows the standard version of KO where the lower frame element cuff (150) is positioned on the anterior of the wearer's leg.)

Figure 16B:
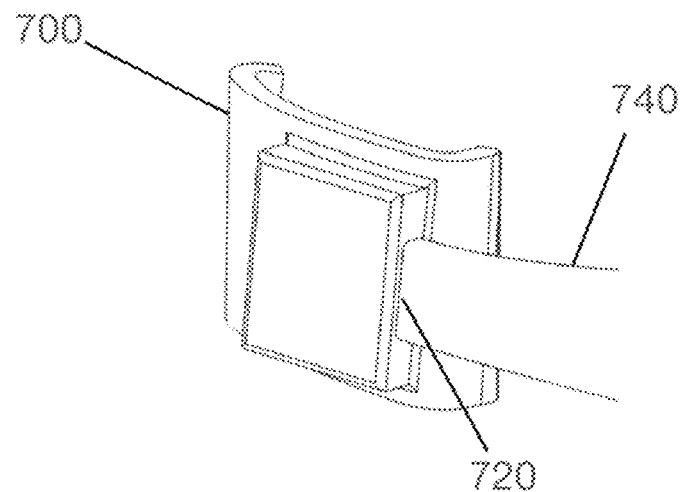

The clamp has an attachment point (720) with—as shown and for example only—a substantially rectangular opening to which various devices could be attached. As shown in FIG. 16b, the dovetail-like mechanical attachment shown previously in FIG. 13b (240) is connected to the clamp (700) via a rail (740) that is secured to the attachment point (720). (Identical element numbers 700, 720, and 740 used in FIG. 16a and FIG. 16b.)

Figure 17A:
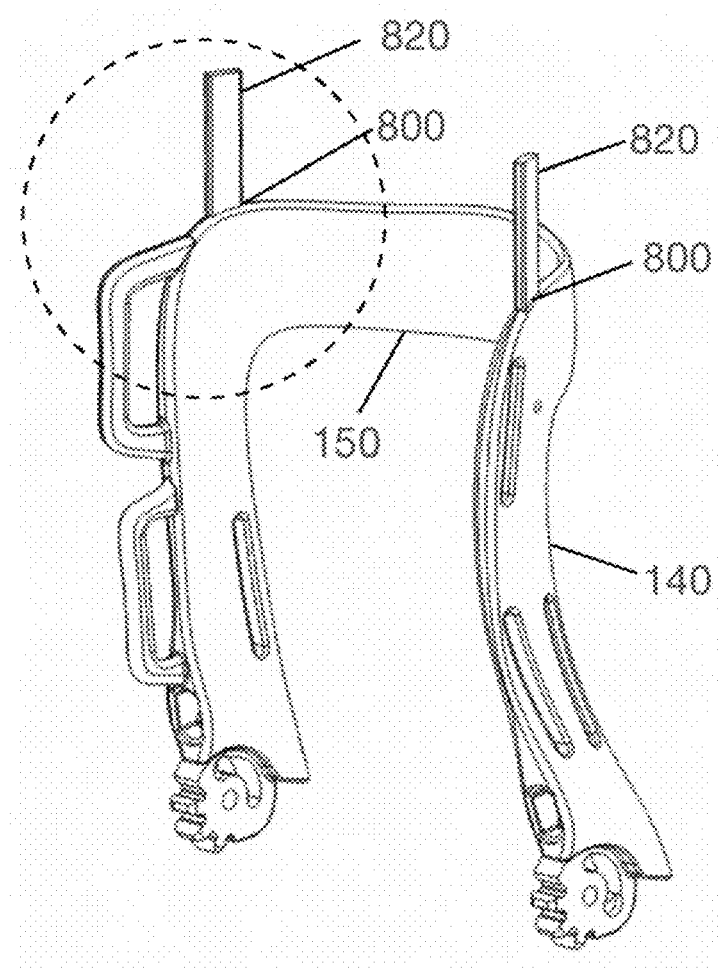
FIG. 17a-17b illustrate exemplary attachment mechanism(s) to combine the knee orthosis component with the ankle foot orthosis component, or the hip component with the knee orthosis component, according to the present invention.
Figure 17B:
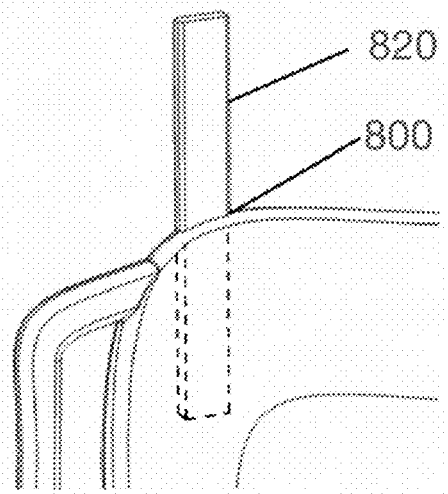

FIG. 17b shows an enlargement of the details of the universal attachment system drawn within the dashed circle in FIG. 17a. The lower frame element (140) of a knee orthosis is shown in FIG. 17a for clarity.

A rectangular shape of the attachment point (820) is illustrative only and not limiting. Other opening shapes such as an oval, square, polygon, 'H' shaped, circular, dovetail, or combinations thereof could be used. Likewise, the substantially C-shaped clamp is merely an example of a low-profile clamp and is not meant to be limiting.

The clamp could be attached reversible to a knee orthosis by a tight mechanical fit and/or by traditional fastening elements (e.g., screws) or attached permanently to the knee orthosis with the addition of a bonding agent (e.g., glue), mechanical fasteners (e.g., rivets), or otherwise bonded (e.g., sonic bonding) or the like. The clamp could be attached to the lower element of a knee orthosis, the upper element, or both depending on the intended use of the additional device. Likewise, multiple clamps could be employed for security or adjustability. Clamps like the one shown in FIG. 17a and FIG. 17b would be advantageous for securing a patella guidance mechanism or orthotic to a knee orthotic, by way of example only.

Further, FIG. 17a shows the lower leg element (140) with lower cuff (150) of a knee orthotic upside-down to reveal the universal coupling feature (820) located in a corresponding opening (800) in the sides of the lower frame element. The knee orthotic can be designed to conform to the wearer's leg with the result that the side elements have a thin direction (along the medial-lateral axis) and a wide direction (along the posterior-anterior axis), in aspects. The universal coupling feature can be embedded within one or both side elements and penetrates a prescribed distance within the lower frame element. (Shown in FIG. 17b with identical element numbers.)

One method of manufacturing a custom brace according to the present invention is to take a scan of the wearer's leg, customize the shape of the orthotic to the wearer, and 3D print the resulting custom orthotic. Materials which are both suitable for 3D printing and a lightweight custom knee orthotic are typically polymeric such as nylon, polypropylene, fiber filled thermoplastics, and the like.

The size and shape of the universal coupling feature is important to the proper function of the knee orthotic and the, for example, ankle-foot orthotic to be coupled. If the cross-sectional area of the coupling feature is too small, the coupling element will not position the ankle-foot orthotic securely. If the cross-sectional area of the coupling feature is too large, it will impede the ability of the knee orthotic to transfer forces to unload the knee as intended.

In an experiment, the shoe strut of an AFO was clamped in a vise. A force meter was attached to the lower leg strut at approximately the same location that the AFO leg cuff is situated. The AFO was pulled into a roughly 90 degree orientation to simulate the resting dorsiflexion position of a wearer's ankle. The force to flex the AFO strut was measured to be 34 N.

In experiments, several different coupling element shapes and resulting wall thickness for a knee orthotic were modeled using finite element analysis. It was found that a coupling element cross section of 0.125×0.4" when embedded at least 0.5" in a knee orthotic lower frame element would produce a safety factor of >2 under a static load of 34 N when the frame material was made of nylon.

In aspects, it can be preferable to routinely manufacture the knee orthotic with universal coupling features. In the embodiment shown in FIGS. 17a and 17b, these would be filled with a functioning or non-functioning (aesthetically pleasing) plug that could be removed from one or both sides when needed and replaced with a coupling feature (820).

The universal coupling element (820) shown in FIG. 17b can be a stub and is shown for illustrative purposes—as shown it does not connect to any other device or adapter. Other coupling mechanisms can be used. For example, as shown in FIG. 16a, the rail (740) and dovetail-like mechanical slot (240) could be modified to connect to the universal feature opening (800 in FIG. 17a) in this embodiment. Likewise, an oblong universal coupling opening could also be provided in one or both of the upper frame element side elements for use to secure an ankle-foot orthotic to a knee orthotic, or for uses other than the secure connection of an ankle-foot orthotic to a knee orthotic, such as connecting a lower limb prosthetic.

Lower limb prosthetics can be fabricated to be generally anatomically correct to mimic the size and shape of a missing lower leg. Other times, they can be fabricated for mainly functional needs and eschew the aesthetics of mimicking the missing limb. In the former case, the strapping and attachment means of a standard orthotic may be sufficient to provide its intended function. In the latter case, some kind of accommodation is often needed.

The adapters or universal connectors described herein have been shown to be advantageous to secure a knee orthotic with other devices and orthoses such as ankle-foot orthoses, patella motion control orthoses, upper leg and thigh orthoses, as well as various pads, supports, load distributors, etc. Such adapters or universal connectors may also be employed to connect a knee orthotic to a lower limb prosthetic. Instead of fitting the adapter or universal connector with a dovetail-like mechanical slot to mate with an ankle-foot orthotic (for example), another mechanical mechanism suitable to connect with a lower limb prosthetic could be employed, such as a socket, which may be a part of the KO component, or may be a separate, modular and optionally customizable adapter or universal connector.

Figure 6B:
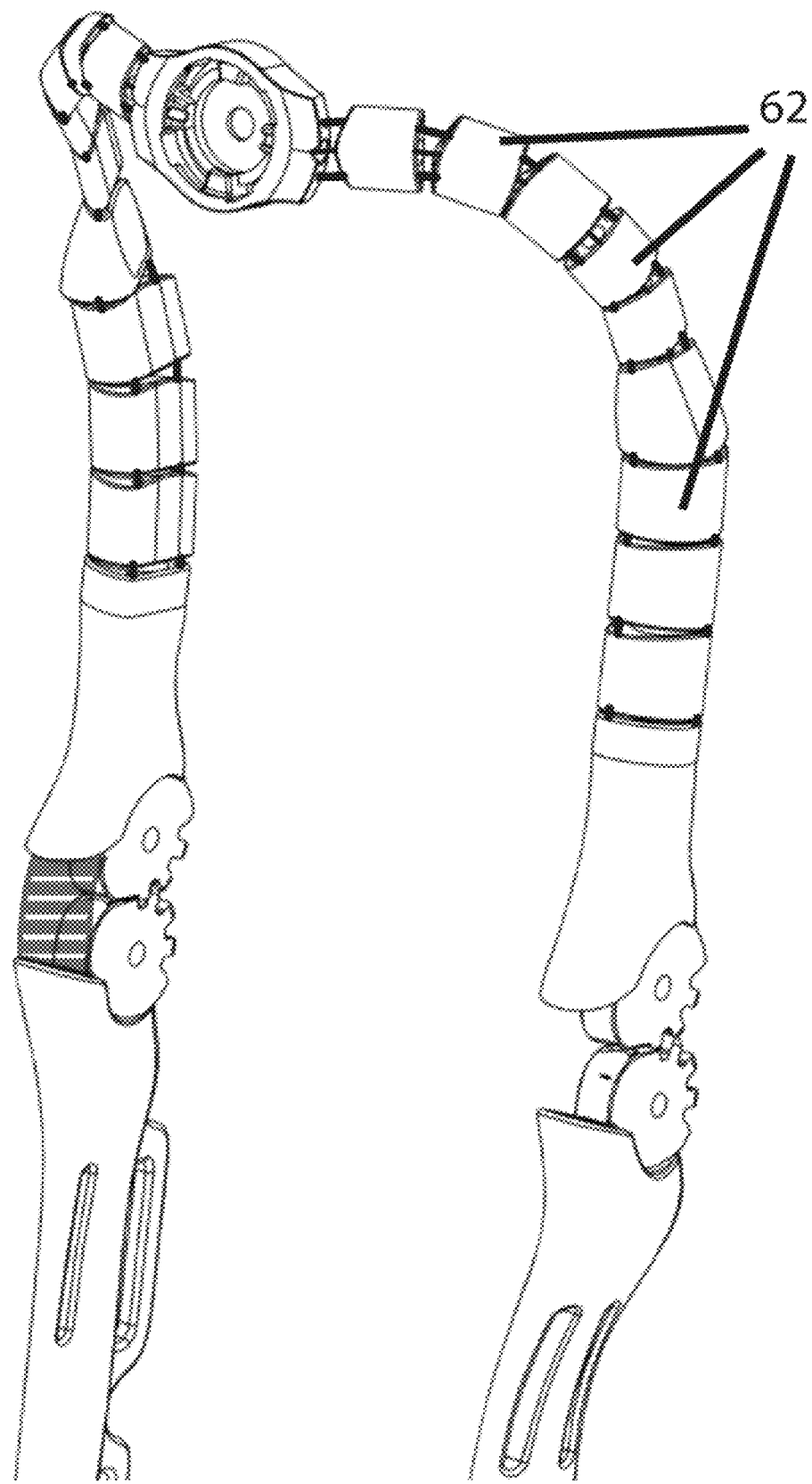

The attachment mechanism, or any portion of the orthosis including the upper and lower portions (e.g. brace frames), energy storage elements, hinges, or pads may be adjusted to better fit the user, alter gait pattern, or provide a different joint geometry. Such further modification may be achieved through thermoforming of the components, for example if the joint brace frames are composed of a nylon, polypropylene or other thermoplastic material. Regions or components of the brace may comprise a flexible chain of subunits, which can be set into a desired conformation, optionally added or removed, and then locked together into a rigid or semi-rigid conformation. As seen in FIG. 6b, regions or components of the brace may comprise a flexible chain of subunits (62), which can be set into a desired conformation, optionally added or removed, and then locked together into a rigid or semi-rigid conformation.

Figure 18:
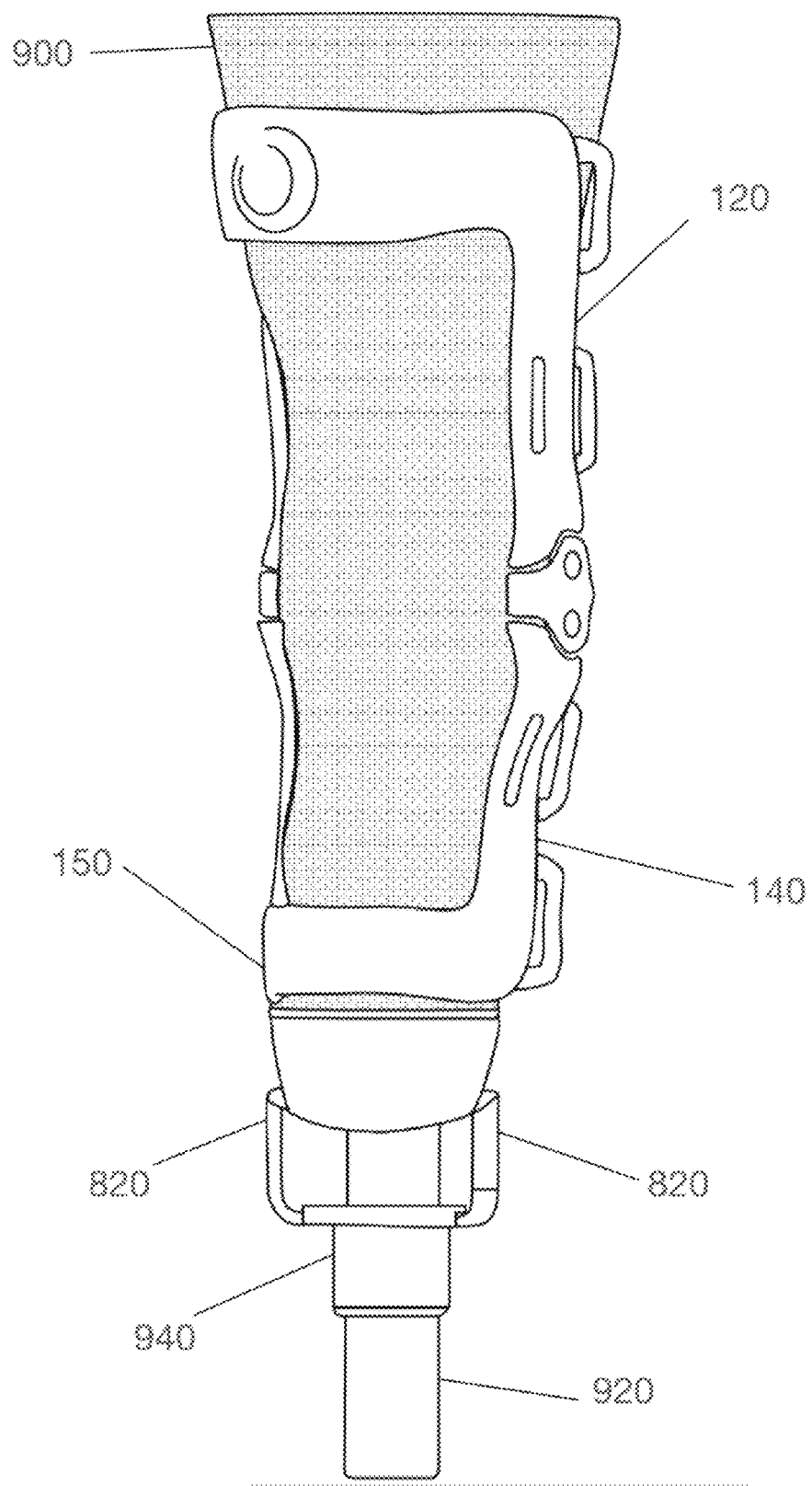
FIG. 18 illustrates exemplary attachment mechanism(s) to combine the knee orthosis component with a prosthesis, according to the present invention.

FIG. 18 shows a leg (900) fitted with a non-anatomically correct lower limb prosthetic (920). An upper leg frame element (120) is secured with a traditional strapping mechanism (not shown). The lower leg frame element (140) may be secured with a traditional strapping mechanism (not shown) and/or a fitting (940) designed for a prosthetic connected securely via any one or combinations of connection mechanisms described herein. For illustrative purposes, in FIG. 18, the universal connector mechanism shown in FIG. 17a (element 820) can employed to connect the prosthetic fitting (940) to the lower leg frame element (140). (Lower frame cuff also shown 150.)

Accessory Components

In aspects, the KAFO or HKAFO may contain other accessory components, either attached to or included with the device as needed by the patient. These components could be accessory to the main KO, AFO and HO components that comprise the KAFO or HKAFO itself. One example is a patellar tracking control device. The device would mount to approximately or mostly to centers of a brace (for example connected to the hinge caps of the KO component) rather than brace frames or arms so that a downward force is not generated on the patella into the trochlea. A semi-circular component can lay over the patella and can be tightened to pull the patella in one direction or combination of directions, as desired. The amount of force may also be adjusted by the user, for example if the device itself contained an adjustable tensioning system activated by a tensioning dial in order to provide a force in one or more of the ML plane and/or the AP plane. The device may be affixed to a rigid frame or to a soft material such as a flexible sleeve. Different padding materials such as a gel may be used. A purpose is to cup or scoop the patella and move it to a more biomechanically favorable position. The device may also be integrated within the strapping system. The tensioning system may be incorporated in-line with the KO component tensioning system as described herein. The inclusion of such accessories further expands the modularity of the device allowing for a greater range of patient-specific functions and improved resulting outcomes.

Software and Sensor-Enabled Devices

Embodiments of the invention that include one or more sensors on the device, and in aspects a processor on or off the device, also include a computer readable medium comprising one or more computer files comprising a set of computer-executable instructions for performing one or more of the calculations, steps, processes and operations described and/or depicted herein. In exemplary embodiments, the files may be stored contiguously or non-contiguously on the computer-readable medium. Embodiments may include a computer program product comprising the computer files, either in the form of the computer-readable medium comprising the computer files and, optionally, made available to a consumer through packaging, or alternatively made available to a consumer through electronic distribution. As used in the context of this specification, a "computer-readable medium" is a non-transitory computer-readable medium and includes any kind of computer memory such as floppy disks, conventional hard disks, CD-ROM, Flash ROM, non-volatile ROM, electrically erasable programmable read-only memory (EEPROM), and RAM. In exemplary embodiments, the computer readable medium has a set of instructions stored thereon which, when executed by a processor, cause the processor to perform tasks, based on data stored in the electronic database or memory described herein. The processor may implement this process through any of the procedures discussed in this disclosure or through any equivalent procedure.

In other embodiments of the invention, files comprising the set of computer-executable instructions may be stored in computer-readable memory on a single computer or distributed across multiple computers. A skilled artisan will further appreciate, in light of this disclosure, how the invention can be implemented, in addition to software, using hardware or firmware. As such, as used herein, the operations of the invention can be implemented in a system comprising a combination of software, hardware, or firmware.

Embodiments of this disclosure include one or more computers or devices loaded with a set of the computer-executable instructions described herein. The computers or devices may be a general purpose computer, a special-purpose computer, or other programmable data processing apparatus to produce a particular machine, such that the one or more computers or devices are instructed and configured to carry out the calculations, processes, steps, operations, algorithms, statistical methods, formulas, or computational routines of this disclosure. The computer or device performing the specified calculations, processes, steps, operations, algorithms, statistical methods, formulas, or computational routines of this disclosure may comprise at least one processing element such as a central processing unit (i.e., processor) and a form of computer-readable memory which may include random-access memory (RAM) or read-only memory (ROM). The computer-executable instructions can be embedded in computer hardware or stored in the computer-readable memory such that the computer or device may be directed to perform one or more of the calculations, steps, processes and operations depicted and/or described herein.

Additional embodiments of this disclosure comprise a computer system for carrying out the computer-implemented method of this disclosure. The computer system may comprise a processor for executing the computer-executable instructions, one or more electronic databases containing the data or information described herein, an input/output interface or user interface, and a set of instructions (e.g., software) for carrying out the method. The computer system can include a stand-alone computer, such as a desktop computer, a portable computer, such as a tablet, laptop, PDA, or smartphone, or a set of computers connected through a network including a client-server configuration and one or more database servers. The network may use any suitable network protocol, including IP, UDP, or ICMP, and may be any suitable wired or wireless network including any local area network, wide area network, Internet network, telecommunications network, Wi-Fi enabled network, or Bluetooth enabled network. In one embodiment, the computer system comprises a central computer connected to the internet that has the computer-executable instructions stored in memory that is operably connected to an internal electronic database. The central computer may perform the computer-implemented method based on input and commands received from remote computers through the internet. The central computer may effectively serve as a server and the remote computers may serve as client computers such that the server-client relationship is established, and the client computers issue queries or receive output from the server over a network.

The input/output interfaces may include a graphical user interface (GUI), which may be used in conjunction with the computer-executable code and electronic databases. The graphical user interface may allow a user to perform these tasks through the use of text fields, check boxes, pull-downs, command buttons, and the like. The software and GUI may provide for specific fabrication instructions, including but not limited to component selection, selection of adapter mechanisms, selection of accessories, methods for attachment and adjustment of components, instructions for device fitment, and instructions for patient use. A skilled artisan will appreciate how such graphical features may be implemented for performing the tasks of this disclosure. The user interface may optionally be accessible through a computer connected to the internet. In one embodiment, the user interface is accessible by typing in an internet address through an industry standard web browser and logging into a web page. The user interface may then be operated through a remote computer (client computer) accessing the web page and transmitting queries or receiving output from a server through a network connection. Additionally, in aspects, the brace will allow the user to interact with it using other interfaces, such as, but not limited to, foot pedals, physical buttons, haptic feedback, or projected interface elements, and may include multiple interface options in combination with one another, to allow maximum flexibility in the ways the user can interact with the brace.

The joint brace described may be fabricated according to an advanced digital design and selection method. For example, a clinician may select specific user inputs, either indications, radiographic data, biometric data, BMI, lifestyle data, or intended rehabilitation procedures and a computer implemented software will provide a selection of the knee orthosis device, the ankle foot orthosis device, the hip orthosis device, optionally an adapter mechanism, and the adjustable energy storage system, including aspects of positioning of the system around the joint, inclusion of the system on one or more of the orthosis components, amount of energy stored in the system (e.g. by selecting the geometry and polymer of the elastic material) and expected functional output of the device based on all included components. Any component may be custom fabricated, (e.g. using 3D printing technology) using a combination of a scan of the user, a database of dimensions of the intended orthosis components to be included in fabrication, other user inputs collected by either the clinician, or data from device sensors. The design method may also include the selection of components to be included in the fabrication and instructions for fabrication, including but not limited to any of the orthosis components, the energy storage systems, or the attachment mechanisms, presented to the fabricator (e.g., a prosthetist) in a decision tree with instructions for fabrication of the device. Alternatively, the brace may be provided as a kit of components to the clinician or the user to attach or fabricate. The invention provides components and instructions, as well as custom fabricated parts, which removes the complexity of traditional KAFO fabrication, thereby reducing the time, cost and potential for human error in the device production. This can ensure consistency in the delivered patient outcome, regardless of its specificity or complexity.

Based on this digital design method and its compatibility to provide instructions of fabrication for traditional analog methods, novel KO, AFO or HO components containing adjustable energy storage systems, distracting hinge systems or combinations thereof, may be combined with any existing off the shelf or custom KO, AFO, or HO component that the user or clinician may already have available. Such modularity provides a wide range of options for personalization of outcomes, which can be further down-selected by data collected on the outcomes of those combinations of products in the field.

The invention described herein also includes, by way of example, the following Aspects:

Aspect 1: An unloading joint brace comprising the components of:

a vertical support comprising an upper portion and a lower portion, wherein the upper portion comprises upper rigid, semi-rigid, or soft portions sized to fit a wearer's first body part adjacent to and above a wearer's joint; and wherein the lower portion comprises lower rigid, semi-rigid, or soft portions sized to fit a wearer's second body part adjacent to and below the wearer's joint;

at least one pivoting hinge assembly, wherein a hinge assembly proximal end is connected to the upper portion and a hinge assembly distal end is connected to the lower portion;

wherein the pivoting hinge assembly further comprises a proximal and a distal subunit with a posterior and anterior side, each subunit optionally housing a gear that intermeshes with an optional opposing gear during articulated joint movement;

at least one energy storage element extended between the proximal and distal hinge subunits, wherein the at least one energy storage element is on or integrated within the proximal and distal hinge subunits and partially, mostly, or completely covered by the proximal and/or distal hinge subunits, wherein a first end of the at least one tensioning element is directly or indirectly attached to the upper portion and a second end of the at least one tensioning element is directly or indirectly attached to the lower portion, and wherein the at least one tensioning element is capable of increasing a tension force within the at least one tensioning element when the hinge assembly is moved to a flexed position by applying a substantially equal pulling force or forces where the at least one energy storage element directly or indirectly attaches to the upper portion and where the at least one energy storage element directly or indirectly attaches to the lower portion, thereby reducing a load force or forces on a wearer's joint; and, wherein when the joint brace is a one-sided brace, then the hinge assembly is on one side of the wearer's joint; and, when the knee orthosis is a full brace, then the hinge assembly is on both sides of the wearer's joint.

Aspect 2: The unloading joint brace of Aspect 1, wherein the at least one energy storage element of the hinge assembly further comprises the at least one tensioning element extending between the subunits on an anterior side of the optionally housed gears, and wherein when there is more than one tensioning element, then the more than one tensioning elements are adjacent to one another and oriented in a longitudinal direction.

Aspect 3: The unloading joint brace of Aspect 1, wherein the unloading joint brace further comprises an unloading mechanism capable of enabling the wearer to engage and disengage, and/or increase and decrease the energy in, the at least one energy storage element.

Aspect 4: The unloading joint brace of Aspect 3, wherein the unloading mechanism comprises a slide member attached to the proximal end of the at least one energy storage element, and a knob or rotatable handle on an exterior surface of the hinge assembly, able to move the slide member and the at least one energy storage element proximal end upward upon a user rotating the knob or rotatable handle either clockwise or counter-clockwise, thereby increasing tension or compression in the at least one energy storage element; and able to release the tension or compression when the knob or rotatable handle is rotated in an opposite direction, wherein the knob or rotatable handle is able to be rotated to a plurality of positions that produce different levels of tension or compression.

Aspect 5: The unloading joint brace of Aspect 3, wherein the unloading mechanism comprises:

a rotatable ratchet-pawl system on a distal and/or a proximal end of the hinge assembly, able to anchor the at least one energy storage element to the rotating member, which upon rotation draws tension in the at least one energy storage element; and a disengagement member able to quickly release the ratchet-pawl system to reduce or release the tension or compression.

Aspect 6: The unloading joint brace of Aspect 3, wherein the unloading mechanism comprises a knob or rotatable handle attached to the at least one energy storage element, wherein the knob or rotatable handle is moved a first direction that increases tension or compression in the at least one energy storage element and can maintain tension or compression by locking into one or more positions, and wherein tension or compression can be reduced or released by moving the knob or rotatable handle into a second position.

Aspect 7: A joint brace with a pivoting hinge assembly, comprising, a proximal and a distal subunit, each subunit housing an optionally teethed gear;

a distal and a proximal optionally teethed gear, wherein if gears are present they are able to intermesh during an articulated joint movement;

at least one tensioning element with a proximal band end and a distal band end, wherein the at least one tensioning element extends between the subunits, with the distal band end affixed to the distal subunit and/or the proximal band end affixed to the proximal subunit; and, an adjustable unloading mechanism, wherein the hinge assembly is able to permanently and/or temporarily un-load a force or forces from a wearer's joint when the wearer moves back and forth between an extended and a flexed joint position, wherein the adjustable unloading mechanism is capable of allowing the wearer to increase and decrease the tension in the at least one tensioning element while the wearer is wearing the joint brace by shortening the at least one tensioning element, lengthening the at least one tensioning element, pulling on the at least one tensioning element, tightening the at least one tensioning element, releasing some or all tension on the at least one tensioning element, or combinations thereof.

Aspect 8: The joint brace with a pivoting hinge assembly of Aspect 7, wherein the unloading mechanism for extending the proximal end of the at least one tensioning element band comprises a slide member attached to the proximal end of the at least one tensioning element, and a rotatable handle on an exterior surface of the hinge assembly that is able to move the slide member and the at least one tensioning element proximal end upward upon a user rotating the rotatable handle, thereby increasing tension in the at least one tensioning element and able to release or decrease the tension when the rotatable handle is counter-rotated, wherein the rotatable handle is able to be rotated to a plurality of positions that produce different levels of tension.

Aspect 9: The joint brace with a pivoting hinge assembly of Aspect 7, wherein the unloading mechanism is attached to one or both ends of the at least one tensioning element, and the hinge assembly further comprises:

a rotatable ratchet-pawl system on a distal and/or a proximal end of the hinge assembly, able to impinge the at least one tensioning element to prevent the band from stretching and to increase the tension in the at least one tensioning element; and a disengagement member able to release the ratchet-pawl system to reduce the tension.

Aspect 10: The joint brace with a pivoting hinge assembly of Aspect 7, wherein the subunits are spaced apart, and further comprising a center cap member or members residing between or housing the subunits and able to cover and protect the at least one tensioning element. A center cap can be comprised of one or more rigid or semi-rigid components such as a support or prong that may or may not encase a tensioning element. A center cap may be located on one or more sides of the hinge assembly.

Aspect 11: The joint brace with a pivoting hinge assembly of Aspect 7, wherein the adjustable unloading mechanism comprises a ratcheting-pawl member capable of allowing the wearer to position, set, or adjust the at least one tensioning element at or to a wearer selected tension.

Aspect 12: A method of unloading a force or forces from a joint by a wearer of a joint brace, the steps comprising:

attaching the joint brace with a pivoting hinge assembly to a wearer's joint, wherein the pivoting hinge assembly comprises:

a proximal and a distal portion, each portion housing a gear;

a distal and a proximal gear able to intermesh during an articulated joint movement; and at least one energy storage element with a proximal end and a distal end, wherein the at least one energy storage element extends between the proximal and distal portions on an anterior side of the gears, with the distal band end affixed to the distal portion or the proximal band end affixed to the proximal portion; and wherein the joint brace comprises an adjustable unloading mechanism capable of increasing the tension or compression on the at least one energy storage element, and wherein tension or compression on the at least one energy storage element is created by applying a substantially equal pulling force or forces where the at least one energy storage element directly or indirectly attaches to the proximal portion and where the at least one energy storage element directly or indirectly attaches to the distal portion;

engaging the unloading mechanism when the wearer requires increased stability and/or tension or compression in the joint brace; and, disengaging or adjusting the unloading mechanism when the wearer no longer requires the increased stability and/or tension or compression, or when the wearer no longer requires the same amount of increased stability and/or tension or compression.

Aspect 13: The method of unloading a force or forces from a joint by a wearer of a joint brace of Aspect 12, wherein the unloading mechanism further comprises a slide member attached to the proximal end of the at least one energy storage element, and a rotatable handle on an exterior surface of the hinge assembly that is able to move the slide member and the at least one energy storage element proximal end upward upon a wearer rotating the rotatable handle, thereby increasing tension or compression in the at least one energy storage element, and wherein the unloading mechanism is able to release or lower the tension when the rotatable handle is counter-rotated, and wherein the rotatable handle is able to be rotated to a plurality of positions that produce different levels of tension or compression.

Aspect 14: The method of unloading a force or forces from a joint by a wearer of a joint brace of Aspect 12, wherein the unloading mechanism further comprises a rotatable ratchet-pawl system on a distal and/or a proximal end of the hinge assembly able to impinge the at least one energy storage element to prevent the at least one energy storage element from stretching and to increase the tension in the at least one energy storage element, and comprising a disengagement member able to release the ratchet-pawl system to reduce the at least one energy storage element tension or compression.

Aspect 15: The method of unloading a force or forces from a joint by a wearer of a joint brace of Aspect 12, wherein the joint brace further comprises:

a vertical support comprising an upper portion and a lower portion with a medial and a lateral side, wherein the upper portion comprises, an upper unit sized to fit a wearer's body part adjacent to and above a user's joint;

at least one strap capable of attaching the upper unit to the wearer's body part;

wherein the lower portion comprises, a lower unit sized to fit a wearer's body part adjacent to and below the wearer's joint;

at least one strap capable of attaching the lower unit to the wearer's body part;

wherein when the joint brace is a one-sided brace, then the hinge assembly is on the lateral or the medial side of the joint; and, wherein when the joint brace is a full brace, then the hinge assembly in on either or both the lateral or the medial side of the joint.

Aspect 16: The unloading joint brace of Aspect 1, wherein one or more of the components are three dimensionally printed, and/or the joint brace is custom sized using digital imaging of the wearer's joint or adjacent body part or parts.

Aspect 17: An unloading knee orthosis comprising the components of:

a vertical support comprising an upper portion and a lower portion, wherein the upper portion comprises an upper rigid or semi-rigid curved unit sized to fit a user's femur adjacent to and above a user's knee joint; and wherein the lower portion comprises a lower rigid or semi-rigid curved unit sized to fit a user's tibia adjacent to and below the user's knee joint;

at least one pivoting hinge assembly, wherein a hinge assembly proximal end is connected to the upper portion and a hinge assembly distal end is connected to the lower portion;

wherein the pivoting hinge assembly further comprises a proximal and a distal subunit with a posterior and anterior side, each subunit optionally housing a gear that intermeshes with an optional opposing gear during articulated joint movement;

at least one tensioning element integrated within and extending between the proximal and distal hinge subunits, wherein the at least one tensioning element is capable of increasing a tension force within the at least one tensioning element when the hinge assembly is moved to a flexed position, thereby reducing a load force or forces on a user's knee;

wherein when the knee orthosis is a one-sided brace, then the hinge assembly is on the lateral or the medial side of the knee; and, when the knee orthosis is a full brace, then the hinge assembly is on the lateral side of the user's knee, the medial side of the user's knee, or both the lateral side and the medial side of the user's knee; and wherein the hinge assembly further comprises:

a cam unit co-located with the optionally housed gear within the subunit, and upon which the at least one tensioning element is drawn over the cam unit and the optionally housed gear to increase tension during knee flexion; and wherein the hinge assembly is prevented from hyperextending anteriorly by the proximal and distal subunit connecting on the subunits' anterior side.

Aspect 18: An unloading joint brace comprising the components of:

a vertical support comprising an upper portion and a lower portion, wherein the upper portion comprises an upper rigid or semi-rigid curved unit sized to fit a user's femur adjacent to and above a user's knee joint; and wherein the lower portion comprises a lower rigid or semi-rigid curved unit sized to fit a user's tibia adjacent to and below the user's knee joint;

at least one pivoting hinge assembly, wherein a hinge assembly proximal end is connected to the upper portion and a hinge assembly distal end is connected to the lower portion;

wherein the pivoting hinge assembly further comprises a proximal and a distal subunit with a posterior and anterior side, each subunit optionally housing a gear that intermeshes with an optional opposing gear during articulated joint movement;

at least one tensioning element extended between the proximal and distal hinge subunits, wherein the at least one tensioning element is integrated within the proximal and distal hinge subunits and partially, mostly, or completely covered by the proximal and/or distal hinge subunits, wherein a first end of the at least one tensioning element is directly or indirectly attached to the upper portion and a second end of the at least one tensioning element is directly or indirectly attached to the lower portion, and wherein the at least one tensioning element is capable of increasing a tension force within the at least one tensioning element when the hinge assembly is moved to a flexed position by applying a substantially equal pulling force or forces where the at least one tensioning element directly or indirectly attaches to the upper portion and where the at least one tensioning element directly or indirectly attaches to the lower portion, thereby reducing a load force or forces on a user's knee;

wherein when the joint brace is a one-sided brace, then the hinge assembly is on the lateral or the medial side of the knee; and, when the joint brace is a full brace, then the hinge assembly is on the lateral side of the user's knee, the medial side of the user's knee, or both the lateral side and the medial side of the user's knee; and wherein the hinge assembly further comprises at least one connector positioned medial and lateral to the subunits, wherein the connector is capable of connecting the subunits together while enabling the optionally housed gears to rotate, and wherein if the subunits house an optional gear, the connector protects the optionally housed gears and the at least one tensioning element.

Aspect 19: An unloading joint brace comprising the components of:

a vertical support comprising an upper portion and a lower portion, wherein the upper portion comprises an upper rigid or semi-rigid curved unit sized to fit a user's femur adjacent to and above a user's knee joint; and wherein the lower portion comprises a lower rigid or semi-rigid curved unit sized to fit a user's tibia adjacent to and below the user's knee joint;

at least one pivoting hinge assembly, wherein a hinge assembly proximal end is connected to the upper portion and a hinge assembly distal end is connected to the lower portion;

wherein the pivoting hinge assembly further comprises a proximal and a distal subunit with a posterior and anterior side, each subunit optionally housing a gear that intermeshes with an optional opposing gear during articulated joint movement;

at least one tensioning element extended between the proximal and distal hinge subunits, wherein the at least one tensioning element is integrated within the proximal and distal hinge subunits and partially, mostly, or completely covered by the proximal and/or distal hinge subunits, wherein a first end of the at least one tensioning element is directly or indirectly attached to the upper portion and a second end of the at least one tensioning element is directly or indirectly attached to the lower portion, and wherein the at least one tensioning element is capable of increasing a tension force within the at least one tensioning element when the hinge assembly is moved to a flexed position by applying a substantially equal pulling force or forces where the at least one tensioning element directly or indirectly attaches to the upper portion and where the at least one tensioning element directly or indirectly attaches to the lower portion, thereby reducing a load force or forces on a user's knee;

wherein when the joint brace is a one-sided brace, then the hinge assembly is on the lateral or the medial side of the knee; and, when the joint brace is a full brace, then the hinge assembly is on the lateral side of the user's knee, the medial side of the user's knee, or both the lateral side and the medial side of the user's knee;

wherein the unloading joint brace further comprises an unloading mechanism capable of enabling the user to engage and disengage, and/or increase and decrease the tension in, the at least one tensioning element; and wherein the at least one tensioning element is connected on one end to the distal or proximal subunit, and the unloading mechanism comprises:

a substantially inelastic line or wire attached to the at least one tensioning element on a first end, and to a spool on a second end; and a spool operatively connected to an external rotatable knob;

wherein the user is able to increase the tension in the at least one tensioning element by rotating the knob in a first direction, and wherein the substantially inelastic line or wire is connected to the spool; and, wherein the user is able to decrease the tension by rotating the knob in an opposite or second direction, or by releasing a ratchet pawl system mechanism or a locking flange washer system operatively connected to the knob.

Aspect 20: A joint brace with a pivoting hinge assembly, comprising, a proximal and a distal subunit, each subunit housing a teethed gear;

a distal and a proximal teethed gear, wherein the gears are able to intermesh during an articulated joint movement;

at least one tensioning element with a proximal band end and a distal band end, wherein the at least one tensioning element extends between the subunits with the distal band end affixed to the distal subunit and/or the proximal band end affixed to the proximal subunit; and, an adjustable unloading mechanism, wherein the hinge assembly is able to permanently and/or temporarily un-load a force or forces from the user's knee when the user moves back and forth between an extended and a flexed knee position, wherein the adjustable unloading mechanism enables the user to increase and decrease the tension in the at least one tensioning element;

wherein the adjustable unloading mechanism comprises the ability to increase the tension by:
  pulling on the at least one tensioning element;
  adding more tensioning elements of a same or of a different level of tension and/or diameter as the at least one tensioning element, wherein when there is more than one tensioning element, then the tensioning elements are adjacent to one another in a longitudinal orientation;
  substituting the at least one tensioning element with one or more stiffer tensioning element(s);
  folding the at least one tensioning element and extending an tensioning element center point until the at least one tensioning element is taut or more taut; and/or
  using multiple tensioning elements set to engage at different degrees of flexion.

Aspect 21: A joint brace with a pivoting hinge assembly, comprising,
  a proximal and a distal subunit, each subunit housing a teethed gear;
  a distal and a proximal teethed gear, wherein the gears are able to intermesh during an articulated joint movement;
  at least one tensioning element with a proximal band end and a distal band end, wherein the at least one tensioning element extends between the subunits, with the distal band end affixed to the distal subunit and/or the proximal band end affixed to the proximal subunit; and,
  an adjustable unloading mechanism, wherein the hinge assembly is able to permanently and/or temporarily un-load a force or forces from the user's knee when the user moves back and forth between an extended and a flexed knee position, wherein the adjustable unloading mechanism enables the user to increase and decrease the tension in the at least one tensioning element;
  wherein the unloading mechanism comprises,
  the at least one tensioning element attached on either end of the one or more tensioning element to either the proximal subunit, the distal subunit, or both;
  a wire anchored to the at least one tensioning element connected to a spool;
  wherein the spool is connected to an external rotatable knob;
  wherein the user is able to increase the tension in the at least one tensioning element by rotating the knob in one direction, wherein the wire and the at least one tensioning element are pulled taut or more taut; and,
  wherein the user is able to decrease the tension by rotating the knob in a second direction, or by releasing a ratchet pawl mechanism or a locking flange washer system.

Aspect 22: A method of unloading a force or forces from a knee by a user of a joint brace, the steps comprising:
  attaching a joint brace with a pivoting hinge assembly to a user's knee, wherein the pivoting hinge assembly comprises:
  a proximal and a distal portion, each portion housing a gear;
  a distal and a proximal gear able to intermesh during an articulated joint movement; and
  at least one tensioning element with a proximal band end and a distal band end, wherein the at least one tensioning element extends between the proximal and distal portions on an anterior side of the gears, with the distal band end affixed to the distal portion or the proximal band end affixed to the proximal portion; and
  wherein the joint brace comprises an adjustable unloading mechanism capable of increasing the tension on the at least one tensioning element, and wherein tension on the at least one tensioning element is created by applying a substantially equal pulling force or forces where the at least one tensioning element directly or indirectly attaches to the proximal portion and where the at least one tensioning element directly or indirectly attaches to the distal portion;
  engaging the unloading mechanism when the user requires increased stability and/or tension in the joint brace; and,
  disengaging or adjusting the unloading mechanism when the user no longer requires the increased stability and/or tension, or when the user no longer requires the same amount of increased stability and/or tension;
  wherein the unloading mechanism comprises,
  the at least one tensioning element on a first end to the proximal portion or the at least one tensioning element attached on a first end to the distal portion;
  a wire attached on a second end of the at least one tensioning element, wherein the wire is attached to a spool;
  wherein the spool is connected to an external knob;
  wherein the user is able to increase the tension in the at least one tensioning element by rotating the knob in a first direction, wherein the wire and the at least one tensioning element are pulled taut or more taut; and,
  wherein the user is able to decrease the tension in the at least one tensioning element by rotating the knob in a second direction and/or by releasing a ratchet-pawl mechanism or a locking flange washer system.

Aspect 23: An unloading joint brace comprising:
  a proximal and a distal subunit, each subunit housing a pivot joint or teethed gear, wherein the gears are able to intermesh during an articulated joint movement;
  at least one tensioning element with a proximal band end and a distal band end, wherein the at least one tensioning element extends between the subunits with the distal band end affixed to the distal subunit and/or the proximal band end affixed to the proximal subunit; and,
  an adjustable unloading mechanism, wherein the pivot point is able to permanently and/or temporarily un-load a force or forces from a wearer's joint when the wearer moves back and forth between an extended and a flexed joint position, wherein the adjustable unloading mechanism enables the wearer to increase and decrease the tension in the at least one tensioning element;
  wherein the adjustable unloading mechanism comprises the ability to increase the tension by:
  pulling on the at least one tensioning element;
  adding more tensioning elements of a same or of a different level of tension and/or diameter as the at least one tensioning element, wherein when there is more than one tensioning element, then the tensioning elements are adjacent to one another in a longitudinal orientation;
  substituting the at least one tensioning element with one or more stiffer tensioning element(s);
  folding the at least one tensioning element and extending a tensioning element center point until the at least one tensioning element is taut or more taut; and/or
  using multiple tensioning elements set to engage at different degrees of flexion.

Aspect 24: A joint brace, comprising:
  an upper frame and lower frame, connected by at least one unicentric or bicentric hinge, comprising one or more tensioning elements capable of increasing torque in the hinge and generating a force that opposes flexion of the joint;
  wherein the hinge may optionally comprise intermeshing gears that interact when a wearer flexes the joint, and wherein the hinge is optionally adjacent to one or more side plates, caps, or hinge capsules that house the optional gears;

wherein the one or more tensioning elements are in series or parallel, and wherein the one or more the tensioning elements are connected to an adjustable tensioning mechanism, anchored to a point on the brace, contained within one or more tubes in either or both the upper frame or the lower frame, weaved through holes in either or both the upper frame or the lower frame, connected to each other when there are multiple tensioning elements, and/or connected to one or more wires that extend over the hinge of the brace; and wherein the brace may optionally comprise at least one tensioning element stretching over the hinge, and wherein the at least one optional tensioning element is drawn with increasing degrees of flexion or extension so that it is capable of being connected to a tensioning mechanism.

Aspect 25: The unloading joint brace of claim 23 or 24, wherein the one or more tensioning elements comprise one or more elastic bands or one or more springs.

Aspect 26: A joint brace, comprising:

an upper frame and lower frame comprising one or more tensioning elements, connected by at least one unicentric or bicentric hinge, comprising one or more tubes or holes integrated partially or completely within or on the upper or lower frame, wherein the one or more tubes or holes is capable of containing the one or more tensioning elements;

wherein the one or more tensioning elements are optionally secured or protected by the one or more tubes or holes;

wherein the one or more tensioning elements are optionally inserted or weaved through the one or more holes to secure the one or more tensioning elements to the upper frame or lower frame or to keep the one or more tensioning elements in place on the upper frame or lower frame;

wherein the one or more tensioning elements are connected to each other or anchored to the joint brace, connected to a tensioning mechanism, or connected to one or more wires that are positioned across the hinge of the brace, and wherein the one or more tensioning elements are capable of increasing torque in the hinge and generating equal forces on both the upper and lower side of the hinge that oppose flexion of the joint;

wherein the hinge may optionally comprise intermeshing gears that interact when a wearer flexes the joint, and wherein the hinge is optionally adjacent to one or more side plates, caps, or hinge capsules that house the optional gears; and wherein the one or more tensioning elements are optionally anchored to fixed points in the upper frame or the lower frame, or to an adjustable tensioning mechanism.

Aspect 27: A joint brace frame capable of generating torque in a hinge, comprising:

an upper frame and lower frame, that may operatively connect at a joint via a variety of interlocking mechanisms, such as a tongue and groove mechanism or intermeshing gears, wherein the upper frame and lower frame can rotate relative to each other a system of various tensioning elements either partially or fully integrated within tubes in the frame or operatively connected to the frame of the brace that generate tension upon either flexion or extension depending on the tensioning element orientation, and may optionally be combined with an adjustable tensioning mechanism;

a network of rings and holes incorporated within the frame of the brace to allow for the attachment of straps to secure the brace to a user's limb, such as a buckle method, where the female end may be located incorporated in the frame of the brace.

Aspect 28: The unloading joint brace of Aspect 1, where the tensioning element extends across the hinge of the brace.

Aspect 29: A brace frame for a human joint comprising a hinge and an at least two frame components, wherein the hinge comprises one or more slots on the distal and proximal end of frame components allowing for a degree of flexion or extension in a range of up to −5 to up to 160 degrees, wherein the one or more slots are capable of being used to control the amount of extension and flexion of the hinge, wherein the one or more slots circumscribe a pivot point for the hinge, and wherein inserts can be inserted in the one or more slots to restrict the degree of flexion and/or extension of the human joint.

Aspect 30: The brace frame for a human joint of Aspect 29, wherein the inserts comprise different sizes and wherein the different sizes cause varying amounts of extension or flexion limits based on their size.

Aspect 31: The brace frame for a human joint of Aspect 29, wherein the one or more slots are capable of securing the inserts in the one or more slots despite articulated joint movement, and wherein the inserts are held in place by one or more side plates, caps, hinge capsules, or combinations thereof.

Aspect 32: The brace frame for a human joint of Aspect 29, wherein the inserts are inserted below the hinge, and wherein the inserts provide flexion or extension limitation.

Aspect 33: The brace frame for a human joint of Aspect 29, further comprising padding for the brace, wherein the padding may be three-dimensionally printed, and wherein a lattice of the padding is capable of being tailored to provide a desired amount of cushion for a given user or application.

Aspect 34: The brace frame for a human joint of Aspect 33, wherein the padding comprises a hook-and-loop or mushroom pattern, which may be printed directly on the brace frame.

Aspect 35: A method of making a brace for a human joint, comprising:

three-dimensionally scanning the human joint and providing a three-dimensional scan or image;

automatically determining from the three-dimensional scan or image the brace, upper frame, or lower frame design, size, weight, or shape;

scaling the design, size, weight, or shape of the brace, upper frame, or lower frame design to fit the human joint based on the three-dimensional scan or image.

Aspect 36: The method of making a brace for a human joint of Aspect 35, further comprising automatically generating the brace, upper frame, or lower frame and fitting the brace, upper frame, or lower frame to a user's joint, and designing the brace, upper frame, or lower frame to compensate for injuries to the leg based on the three-dimensional scan or image, including adding or decreasing pressure on one or more sides of the human joint.

Aspect 37: The method of making a brace for a human joint of Aspect 35, wherein the design, size, weight, or shape of the brace, upper frame, or lower frame is tailored or formed by computer-implemented software to account for and treat an injury, including depending on a severity of an injury, a type of injury, an injury treatment, and/or needs of a wearer.

Aspect 38: The unloading joint brace of Aspect 1, wherein the upper frame and/or lower frame is three-dimensionally printed, injection molded, pultruded, extruded, machined, or a combination thereof.

Aspect 39: The unloading joint brace of Aspect 1, wherein the upper frame and/or lower frame is thermal molded to adapt to a wearer's leg size or shape, or wherein the brace comprises components or sections comprising material(s) capable of being molded or sculpted using heat or light.

Aspect 40: The unloading joint brace of Aspect 1, further comprising padding, wherein all of or parts of a material used for the padding are capable of being thermal molded to fit a wearer's leg.

Aspect 41: The unloading joint brace of Aspect 1, wherein additional force is applied on an opposing side or on a side opposite of unicompartmental osteoarthritis in a wearer, and wherein a resting position of the brace applies a force to treat unicompartmental osteoarthritis, and wherein the force applied may be a result of modifications to brace frame geometry.

Aspect 42: The unloading joint brace of Aspect 1, further comprising one or more side plates, caps, or hinge capsules, wherein the one or more side plates, caps, or hinge capsules are used for increasing force on a condyle opposite to unicompartmental osteoarthritis in the wearer.

Aspect 43: The unloading joint brace of Aspect 1, further comprising hinge cap(s), wherein the hinge cap(s) comprise a removeable cap and screws allowing for a variable number of condyle spacing pads to be placed within the hinge cap(s) to act as a condyle shim.

Aspect 44: The unloading joint brace of Aspect 43, wherein the hinge cap(s) comprise an additive shim that attaches to the hinge cap(s) to increase condyle spacing to be placed within the hinge cap(s) to act as a condyle shim.

Aspect 45: A joint brace comprising one or more tensioning elements and an adjustable tensioning mechanism, wherein the adjustable tensioning mechanism is coupled to the one or more tensioning elements, wherein the adjustable tensioning mechanism comprises an interface between the adjustable tensioning mechanism and a wearer, and may include a knob, slide, button, tab, digital screen, processor, controller, motor, microdrive, switch, pulley, block and tackle system, or lever, that the wearer can use to adjust an amount of tension in the one or more tensioning elements; wherein adjusting the adjustable tensioning mechanism increases or decreases tension; and wherein the adjustable tensioning mechanism is held in a static position until a wearer changes tension.

Aspect 46: The joint brace of Aspect 45, further comprising one or more sensors that measure and monitor the position of the brace, wherein the one or more sensors are optionally capable of measuring and monitoring velocity or acceleration, wherein the position data, velocity data, or acceleration data, are used as input to a processor or monitoring system for the joint brace, and wherein the position data, velocity data, or acceleration data is used to instruct a motor or other tensioning system on the joint brace to assist or support a joint by increasing or decreasing resistance in the joint brace, or tension in the one or more tensioning elements.

Aspect 47: The joint brace of Aspect 45, wherein the one or more sensors are capable of measuring and monitoring an amount of tension present in the joint brace or the one or more tensioning elements, or the amount of unloading force applied at a wearer's joint.

Aspect 48: The joint brace of Aspect 45, wherein an amount of unloading force at a wearer's joint includes a variable amount that changes as the wearer's joint is extended or flexed.

Aspect 49: The joint brace of Aspect 45, wherein an analog value of tension applied at a wearer's joint is converted to a digital signal.

Aspect 50: The joint brace of Aspect 49, wherein the digital signal informs a wearer of the joint brace regarding how much tension is present in the joint brace or as a change in tension is recognized by the one or more sensors.

Aspect 51: The joint brace of Aspect 45, wherein the one or more sensors are fabricated on or within the brace.

Aspect 52: The joint brace of Aspect 45, wherein the one or more sensors output a digital or electronic signal, and wherein the one or more sensors connect to one or more lights or other indicator, including a viewing port, that indicate information about the joint brace, including an amount of force or tension in the joint brace.

Aspect 53: The joint brace of Aspect 45, further comprising a motor and control processor system, and further optionally comprising a potentiometer, gear box or gearing system, controller, pulley, or block and tackle system, or one or more servo arms or levers.

Aspect 54: The joint brace of Aspect 53, wherein the motor is operatively connected to the one or more tensioning element through a system of gears or screw(s), which are capable of gathering or releasing tension based on inputs from the one or more sensors, wherein the system is managed by a controller or processor.

Aspect 55: The joint brace of Aspect 45, wherein the one or more sensors are connected to a screen on the brace that communicates information such as force generated within the joint brace or weight unloaded by the joint brace.

Aspect 56: The joint brace of Aspect 45, wherein the one or more sensors are synced to a computer-implemented software application on an electronic device to provide a wearer with feedback about an amount of force being applied by the joint brace, a direction a wearer's joint is being overloaded in, or a direction in which a wearer's joint is being flexed or extended, and wherein data from the one or more sensors is analyzed to identify patterns, and is capable of being used as inputs to a controller that determines how one or more motors on the joint brace should function in an assistive or supportive manner.

Aspect 57: The unloading joint brace of Aspect 1, further comprising a tension, acceleration, position, and/or velocity measurement sensor or mechanism, wherein the measurements from the measurement sensor or mechanism are optionally converted to a digital signal and displayed as visual or audio output on the brace or an external electronic device.

Aspect 58: The unloading joint brace of Aspect 57, wherein the digital signal is used to activate one or more lights on the brace to indicate an amount of tension.

Aspect 59: The unloading joint brace of Aspect 57, wherein the digital signal is used to activate a visual indicator on the joint brace showing colors or lights to indicate an amount of tension on the one or more tensioning element to communicate to the wearer an amount of tension in the joint brace.

Aspect 60: The joint brace of Aspect 1, further comprising a motor and control processor system, and further optionally comprising a potentiometer, gear box or gearing system, or one or more servo arms or levers.

Aspect 61: The joint brace of Aspect 1, further comprising one or more motors and one or more sensors, wherein the one or more motors are operatively connected to the one or more tensioning element through a system of gears or screws capable of gathering or releasing tension based on inputs from the one or more sensors, wherein the system is managed by a controller or processor.

Aspect 62: The joint brace of Aspect 1, further comprising one or more motors and one or more sensors, wherein the one or more sensors are connected to a screen on the joint brace that communicates information such as force generated within the joint brace or weight unloaded by the joint brace to the wearer.

Aspect 63: The joint brace of Aspect 1, further comprising one or more motors and one or more sensors, wherein the one or more sensors are synced to a computer-implemented software application on an electronic device to provide the wearer with information about an amount of force being applied by the joint brace, a direction the joint is being overloaded in, or a direction in which the joint is being flexed or extended.

Aspect 64: The joint brace of Aspect 1, further comprising one or more motors and one or more sensors, wherein information from the one or more sensors is automatically analyzed to identify patterns and to send inputs to a controller to control the one or more motors, wherein the one or more motors function in an assistive or supportive manner to the wearer.

Aspect 65: The joint brace of Aspect 1, further comprising a tension, acceleration, position, and/or velocity measurement sensor or mechanism, wherein measurements from the measurement sensor or mechanism are optionally converted to a digital signal and displayed as visual or audio output on the joint brace or an external electronic device.

Aspect 66: The joint brace of Aspect 65, wherein the digital signal is used to activate one or more lights on the joint brace to indicate an amount of tension.

Aspect 67: The joint brace of Aspect 1, further comprising a visual indicator using different colors or lights to indicate different tension in the one or more tensioning element to communicate to the wearer an amount of tension in the joint brace.

Aspect 68: The joint brace of Aspect 1, further comprising one or more sensors, one or more processors, one or more controllers, one or more motors, or combinations thereof, wherein the one or more processors are located on the brace or on an external electronic device, including a computer, a computer processing unit, a laptop computer, a tablet computer, a phone, a smartphone, a server, internet, cloud, or combinations thereof.

Aspect 69: A joint brace, comprising:
an upper portion connected to an appendage above the joint and a lower portion connected to an appendage below the joint;
one or more tensioning elements;
an adjustable tensioning mechanism capable of adjusting tension in the one or more tensioning elements; and
one or more sensors, one or more processors, one or more motors, one or more controllers, or combinations thereof;
wherein the one or more sensors measure tension in the one or more tension elements and/or the joint brace;
wherein the one or more processors are located on the brace or on an external electronic device;
wherein the one or more sensors, one or more processors, one or more motors, one or more controllers, or combinations thereof, are capable of adjusting the adjustable tensioning mechanism and/or the one or more tensioning elements.

Aspect 70: The unloading joint brace of Aspect 69, wherein the one or more sensors are tension measurement sensors capable of being used to restrict a wearer from over-tensioning the one or more tensioning elements, or wherein the tension measurement sensors are capable of sending tension information and/or directly or indirectly controlling the adjustable tensioning mechanism.

Aspect 71: The unloading joint brace of Aspect 69, wherein the one or more sensors measure tension on the one or more tensioning elements, wherein the one or more sensors send tension data to the one or more processors, and wherein the one or more processors send instructions to the one or more controllers and/or the one or more motors.

Aspect 72: The unloading joint brace of Aspect 69, wherein the one or more processors are located on the joint brace or on an external electronic device in communication with the joint brace or the one or more sensors, including a computer, a computer processing unit, a laptop computer, a tablet computer, a phone, a smartphone, a server, internet, cloud, or combinations thereof.

Aspect 73: The unloading joint brace of Aspect 69, wherein the one or more controllers or one or more motors is capable of adjusting tension in the joint brace and/or the one or more tensioning elements, and wherein the adjustment is based on data from the one or more sensors.

Aspect 74: The unloading joint brace of Aspect 69, wherein the one or more sensors, one or more processors, one or more motors, one or more controllers, or combinations thereof, are capable of automatically adjusting tension in the joint brace and/or the one or more tensioning elements.

Aspect 75: The unloading joint brace of Aspect 69, wherein the one or more sensors, one or more processors, one or more motors, one or more controllers, or combinations thereof, are capable of automatically adjusting tension in the joint brace and/or one or more tensioning elements based on a preset upper and/or lower range of tension.

Aspect 76: The unloading joint brace of Aspect 69, wherein the one or more sensors, one or more processors, one or more motors, one or more controllers, or combinations thereof, are capable of providing feedback to a wearer about tension on the joint brace and/or motion of the joint.

Aspect 77: The unloading joint brace of claim 69, wherein the one or more sensors, one or more processors, one or more motors, one or more controllers, or combinations thereof, are capable of informing a wearer and/or another person that the joint brace and/or the one or more tensioning elements are overloaded.

Aspect 78: The unloading joint brace of Aspect 69, wherein the one or more sensors, one or more processors, one or more motors, one or more controllers, or combinations thereof, are capable of informing a wearer and/or another person information related to the joint brace, tension, the one or more tensioning elements, the hinge, a prescribed treatment, a joint movement, joint health, an injury, treatment options, or combinations thereof.

Aspect 79: The unloading joint brace of Aspect 69, wherein information about the joint brace or use of the joint brace is communicated to a wearer or another person, wherein performance or function of the joint brace is capable of being modified based on the information.

Aspect 80: A joint brace, wherein the joint brace is used for rehabilitation or physical therapy, wherein the joint brace generates electric impulses that stimulate muscles to contract to strengthen or repair tissue, including strengthening or repairing muscles which have become shortened, weakened, or atrophied due to injury or disease.

Aspect 81: The joint brace of claim 80, wherein the joint brace integrates electrical muscle stimulation (EMS or E-STIM therapy) equipment or electromyostimulation (EMS) or neuromuscular electrical stimulation (NMES) equipment that is attached to or integrated within the joint brace.

Aspect 82: A joint brace, wherein the joint brace is used for rehabilitation or physical therapy, wherein the joint brace generates electric impulses that use transcutaneous electrical nerve stimulation (TENS) to stimulate nerves for managing or blocking pain signals to a brain of a wearer, wherein a battery and electrodes are attached to or integrated within the joint brace.

Aspect 83: A joint brace or joint wrap, wherein the joint brace or joint wrap is used as a non-invasive mechanism for physical therapy or to rehabilitate joint or tissue, or to reduce pain in a wearer, wherein the joint brace or wrap is attached to or contains an apparatus that generates sound waves which cause vibrations that may be pulsed on and off or continuously.

Aspect 84: In aspects, the braces and orthotics described herein may be used in conjunction with sensors and/or motors.

Aspect 85: The brace or orthotic tension may be modified in real time or another time based on the user's needs.

Aspect 86: In aspects, the braces and orthotics described herein have the ability to communicate wirelessly, via Bluetooth, via WiFi, or via direct connection.

Aspect 87: In aspects, a user's knee is profiled and the injury is characterized to approximate how much assistive force should be applied as a function of degree of flexion. The need for support on either side of the tibiofemoral compartments is also considered and used as a design input.

Aspect 88: In Aspects, 3D scanning, radiographic data (e.g., x-rays, MRIs), patient reported pain levels, and measurements are used to design and/or adjust the brace and/or components of the brace.

Aspect 89: In aspects, computer-implemented software calculates and estimates relative portions of soft and firm tissue based on input such as 3D scans, user height, user weight, user BMI, user age, user-reported pain levels, and other historical information on the user.

Aspect 90: In aspects, computer-implemented software models the user's gait based on positioning data and determines the amount of corrective and assistive force to improve joint function and/or user health. In aspects, computer-implemented software estimates user's assistive and corrective needs for different activities and generates outputs for brace design parameters and/or tensioning or adjustments. In aspects, brace design may be partially or fully automated based on these design parameters.

Aspect 91: In aspects, extension and flexion stops are built into the brace design as a continuous material connected to the upper and lower brace portions.

Figure 19:
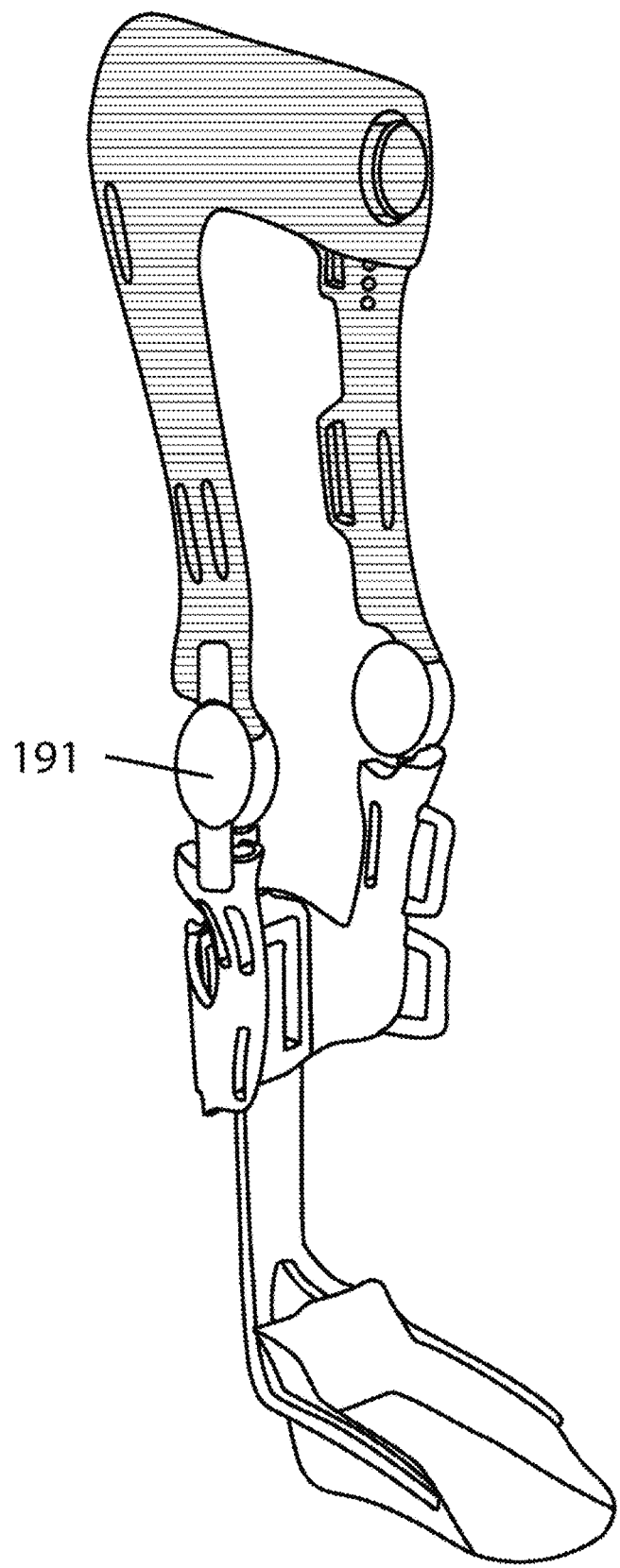
FIG. 19 is an illustration of an adjustable tensioning KAFO containing a drop lock mechanism, according to the present invention.

Aspect 92: In aspects, FIG. 19 shows a drop lock mechanism (191) is built into the knee orthosis hinge, so that at a specific degree of knee extension (or at a specific stage of gait) the hinge becomes either locked into place at the specific degree, or prevents any further flexion while still allowing for rotation through the remaining degrees of extension. This may be accomplished with extrusions built into the hinge that can be moved by an elastic element when triggered by the specific degree of knee extension. The extrusions would then become wedged into the rotating gears to prevent further hinge rotation. The same mechanism may be applied to cause a locking of the hinge once a specific degree of flexion is reached in order to stabilize the joint or prevent joint buckling. The drop lock mechanism may optionally be disengaged by hand, by rotation of the ankle foot orthosis, which may be directly or indirectly connected to the drop lock mechanism, or other similarly derived methods. The drop lock mechanism may be integrated with the unloading hinge element described in U.S. Pat. No. 10,806,619, to provide an unloading force on the knee until the drop lock mechanism is engaged, allowing for both knee unloading and stance control in a single hinge element. In aspects, the adjustable tensioning system may function in combination with the drop lock mechanism, for example driving extension of the KO during gait to a point in which the drop lock mechanism engages on the KO component. Traditional drop lock mechanisms may fail if the user is unable to achieve the degree of extension required to trigger the mechanism to engage. The extension assist mechanism would allow the hinge to fully extend into a range in which the drop lock mechanism would catch, therefore preventing buckling and protecting the joint of the user. In other embodiments, the adjustable tensioning system may completely replace the function of the traditional drop lock mechanism. If a high degree of torque is generated around the KO hinge, forcing extension of the joint, joint flexion and buckling may be prevented altogether, therefore providing the function of a drop lock. The tensioning system may engage, or the tension may increase significantly at a specific range of motion of the joint or stage of gait (e.g. 15° away from full extension), for example by incorporating a cam that engages with the tensioning element at a specific range of motion thereby increasing the effective radius around which the tensioning element generates a torque.

Aspect 93: In aspects, a brace manufactured with inputs from dynamic scanning and tracking software that can assess degree of varus or valgus, rotation of the joint, or gait pattern.

Although the above-recited examples are not to be construed as limiting the scope of the various embodiments of the present disclosure, the examples indicate that the joint brace and hinge assemblies can be constructed for use in an elbow brace. The dimensions of the brace and hinge assemblies can be modified according to the description of the invention herein to treat pain and inflammation associated with a variety of elbow disorders. The same is true of other joints.

The range of adjustability of the braces within the scope of the present invention can be modified by selecting materials of different elasticity for construction of the arm members, by selecting different longitudinal or cross-sectional dimensions for the arm members, or by selecting pads of different fixed thicknesses or different ranges of adjustable thicknesses.

It is further evident that although the joint brace and hinge assemblies of the present invention have been mostly described herein in terms of embodiments adapted to treat osteoarthritis, these embodiments are readily adaptable to treatment of pain associated with a variety of knee disorders. For example, additional embodiments comprise hinge assemblies with the user tension adjustment handle, knob, etc., on the user's tibia versus an exemplified embodiment on the user's femur.

Other aspects include the following:

Aspect 1B: A knee ankle foot orthosis comprising:
a knee orthosis component;
an ankle-foot orthosis component; and
at least one attachable or permanently affixed connection mechanism connecting the knee orthosis component to the ankle-foot orthosis component;
wherein the knee orthosis component is comprised of:
an upper portion and a lower portion connected by a hinge, and
an adjustable energy storage mechanism, wherein the adjustable energy storage mechanism generates a force having an amount of force, the force being directed at least one of: around, across, and between, the upper portion and the lower portion;

wherein the adjustable energy storage mechanism allows a wearer of the knee ankle foot orthosis to adjust the amount of the force generated by the adjustable energy storage mechanism relative to at least one of the upper portion, the lower portion, and the hinge.

Aspect 2B: The knee ankle foot orthosis of Aspect 1B, wherein the adjustable energy storage mechanism further allows the wearer to adjust the amount of force generated by the energy storage mechanism while the wearer is wearing the knee ankle foot orthosis.

Aspect 3B: The knee ankle foot orthosis of Aspect 1B, wherein the adjustable energy storage mechanism comprises one or more tensioning element, one or more compression element, or a combination thereof.

Aspect 4B: The knee ankle foot orthosis of Aspect 3B, wherein the one or more tensioning element, the one or more compression element, or both, is one or more elastomer, one or more spring, one or more rigid element, or a combination thereof.

Aspect 5B: The knee ankle foot orthosis of Aspect 1B, wherein the adjustable energy storage mechanism provides a capability of changing the amount of force by one or more magnitudes of force.

Aspect 6B: The knee ankle foot orthosis of Aspect 1B, wherein the adjustable energy storage mechanism comprises at least one of a ratchet and pawl mechanism, a lever, a dial, a pin and slot, a pulley, a sprag clutch, a worm gear, or a friction pad.

Aspect 7B: The knee ankle foot orthosis of Aspect 1B, wherein the adjustable energy storage mechanism is a first adjustable energy storage mechanism, and the ankle-foot orthosis component includes a second adjustable energy storage mechanism.

Aspect 8B: The knee ankle foot orthosis of Aspect 7B, wherein the first adjustable energy storage mechanism is mechanically connected to the second adjustable energy storage mechanism.

Aspect 9B: The knee ankle foot orthosis of Aspect 7B, wherein the first adjustable energy storage mechanism and the second adjustable energy storage mechanism are adjustable using a single adjustment component.

Aspect 10B: The knee ankle foot orthosis of Aspect 7B, wherein the first adjustable energy storage mechanism comprises a first amount of stored energy and the second adjustable storage mechanism comprises a second amount of stored energy.

Aspect 11B: The knee ankle foot orthosis of Aspect 1B, wherein the hinge is a polycentric hinge comprising one or more gears or cams of variable radii, and wherein the variable radii gears or cams generate a distraction force across or around a knee joint.

Aspect 12B: The knee ankle foot orthosis of Aspect 1B, wherein the hinge is a distracting hinge comprising more than one pair of gears or cams, and wherein the more than one pair of gears or cams upon articulation generate a variable degree of distance between the upper and the lower portion at a different ranges of motion of the knee orthosis component.

Aspect 13B: The knee ankle foot orthosis of Aspect 1B, wherein the upper portion and the lower portion of the knee orthosis component are connected by a center cap, and wherein at least one of the upper portion, the lower portion, or the center cap, are curved to fully or partially conform to a wearer's joint or limb.

Aspect 14B: The knee ankle foot orthosis of Aspect 1B, wherein at least one of an attachment mechanism or an attachment point between the knee orthosis component and the ankle-foot orthosis component is capable of withstanding at least 20 N of applied force.

Aspect 15B: The knee ankle foot orthosis of Aspect 1B, further comprising:
one or more sensors, one or more processors, one or more motors, one or more controllers, or combinations thereof;
wherein the one or more sensors, the one or more processors, the one or more motors, the one or more controllers, or the combinations thereof, are capable of adjusting the adjustable energy storage mechanism.

Aspect 16B: The joint brace of Aspect 1B, further comprising a tensioning element, wherein the tensioning element is drawn over the hinge, wherein the tensioning element is integrated within at least one of the upper portion or the lower portion, and wherein the tensioning element is connected to a lace or wire drawn over the hinge.

Aspect 17B: The knee ankle foot orthosis of Aspect 1B, wherein the adjustable energy storage mechanism is capable of changing the amount of force in a substantially continuous, gradual, incremental, or stepwise manner across a range or spectrum of magnitudes of force.

Aspect 18B: The knee ankle foot orthosis of Aspect 1B, wherein the knee orthosis component and the ankle-foot orthosis component are provided as separate components to be assembled or connected to one another.

Aspect 19B: The knee ankle foot orthosis of Aspect 1B, wherein the knee orthosis component and the ankle-foot orthosis component are capable of being modified to fit a shape of a wearer's joint or limb, and wherein once fitted the knee orthosis component and the ankle-foot orthosis component can be fixed into a rigid or semi-rigid shape.

Aspect 20B: A knee ankle foot orthosis comprising:
a knee orthosis component;
an ankle-foot orthosis component; and
at least one attachable or permanently affixed connection mechanism connecting the knee orthosis component to the ankle-foot orthosis component;
wherein the ankle foot orthosis component is comprised of:
an upper portion and a lower portion, and
an adjustable energy storage mechanism, wherein the adjustable energy storage mechanism generates a force having an amount of force, the force being directed at least one of: around, across, and between, the upper portion and the lower portion; and
wherein the adjustable energy storage mechanism allows a wearer of the knee ankle foot orthosis to adjust the amount of the force generated by the adjustable energy storage mechanism relative to at least one of the upper portion and the lower portion.

Aspect 21B: The knee ankle foot orthosis of Aspect 20B, wherein the adjustable energy storage mechanism further allows the wearer to adjust the amount of force generated by the energy storage mechanism while the wearer is wearing the knee ankle foot orthosis.

Aspect 22B: The knee ankle foot orthosis of Aspect 20B, wherein the adjustable energy storage mechanism comprises one or more tensioning element, one or more compression element, or a combination thereof.

Aspect 23B: The knee ankle foot orthosis of Aspect 22B, wherein the one or more tensioning element, the one or more compression element, or both, comprise at least one of an elastomer, a spring, or a rigid element.

Aspect 24B: The knee ankle foot orthosis of Aspect 20B, wherein the one or more adjustable energy storage mechanism provides a capability of changing the amount of force by one or more magnitudes of force.

Aspect 25B: The knee ankle foot orthosis of Aspect 20B, wherein the adjustable energy storage mechanism comprises at least one of a ratchet and pawl mechanism, a lever, a dial, a pin and slot, a pulley, a sprag clutch, a worm gear, or a friction pad.

Aspect 26B: The knee ankle foot orthosis of Aspect 20B, wherein the adjustable energy storage mechanism generates the force around one or more axes of a joint.

Aspect 27B: A hip knee ankle foot orthosis comprising:
a hip orthosis component;
a knee orthosis component;
an ankle-foot orthosis component; and
at least two attachable or permanently affixed connection mechanisms connecting the hip orthosis component to the knee orthosis component and the knee orthosis component to the ankle-foot orthosis component;
wherein the hip orthosis component is comprised of an upper portion and a lower portion connected by an adjustable energy storage mechanism, wherein the adjustable energy storage mechanism generates a force having an amount of force, the force being directed at least one of: around, across, and between, the upper portion and the lower portion; and
wherein the adjustable energy storage mechanism allows a wearer of the hip knee ankle foot orthosis to adjust the amount of the force generated by the adjustable energy storage mechanism relative to at least one of the upper portion and the lower portion.

Aspect 28B: A hip knee ankle foot orthosis comprising:
a hip orthosis component;
a knee orthosis component;
an ankle-foot orthosis component; and
at least two attachable or permanently affixed connection mechanisms connecting the hip orthosis component to the knee orthosis component and the knee orthosis component to the ankle-foot orthosis component;
wherein at least one of the hip orthosis component, the knee orthosis component, or the ankle-foot orthosis component, comprise an adjustable energy storage mechanism, wherein the adjustable energy storage mechanism generates a force having an amount of force, the force being directed at least one of: around, across, and between, an upper portion and a lower portion of the hip orthosis component, the knee orthosis component, or the ankle-foot orthosis component; and
wherein the adjustable energy storage mechanism allows a wearer of the hip orthosis component, the knee orthosis component, or the ankle-foot orthosis component, to adjust the amount of force generated by the adjustable energy storage mechanism relative to at least one of the upper portion and the lower portion of the hip orthosis component, the knee orthosis component, or the ankle-foot orthosis component.

The dimensions, materials, number and type of tensioning elements, and so forth, can be modified to achieve an equivalent level of pain relief as the embodiments disclosed herein.

Although various features of the invention may be described in the context of a single embodiment, the features may also be provided separately or in any suitable combination. Conversely, although the invention may be described herein in the context of separate embodiments for clarity, the invention may also be implemented in a single embodiment.

As used herein, the term "about" refers to plus or minus 5 units (e.g., percentage) of the stated value.

Reference in the specification to "some embodiments", "an embodiment", "one embodiment" or "other embodiments" means that a particular feature, structure, or characteristic described in connection with the embodiments is included in at least some embodiments, but not necessarily all embodiments, of the inventions.

"Attachable" as used herein can mean releasably attachable, such as a component that can be attached and then detached, or a component that is attached and remains attached.

As used herein, the term "substantial" and "substantially" refers to what is easily recognizable to one of ordinary skill in the art.

It is to be understood that the phraseology and terminology employed herein is not to be construed as limiting and are for descriptive purpose only.

It is to be understood that the details set forth herein do not construe a limitation to an application of the invention.

Furthermore, it is to be understood that the invention can be carried out or practiced in various ways and that the invention can be implemented in embodiments other than the ones outlined in the description above.

It is to be understood that the terms "including," "comprising," "consisting" and grammatical variants thereof do not preclude the addition of one or more components, features, steps, or integers or groups thereof and that the terms are to be construed as specifying components, features, steps or integers.

The invention claimed is:

1. A knee ankle foot orthosis comprising:
a knee orthosis component;
an ankle-foot orthosis component; and
at least one attachable or permanently affixed connection mechanism connecting the knee orthosis component to the ankle-foot orthosis component;
wherein the knee orthosis component is comprised of:
an upper portion and a lower portion having a hinge disposed between the upper portion and the lower portion, and an adjustable energy storage mechanism directly or indirectly connecting the upper portion to the lower portion, wherein the adjustable energy storage mechanism generates a tension or compression force having an amount of tension or compression force, the tension or compression force being directed at least one of: around, across, and between, the upper portion and the lower portion;

wherein the adjustable energy storage mechanism allows a wearer of the knee ankle foot orthosis to adjust the amount of the tension or compression force generated by the adjustable energy storage mechanism relative to at least one of the upper portion, the lower portion, and the hinge; and wherein the adjustable energy storage mechanism further allows the wearer to adjust the amount of the tension or compression force generated by the adjustable energy storage mechanism while the wearer is wearing the knee ankle foot orthosis.

2. The knee ankle foot orthosis of claim 1, wherein the adjustable energy storage mechanism comprises one or more tensioning element, one or more compression element, or a combination thereof.

3. The knee ankle foot orthosis of claim 2, wherein the one or more tensioning element, the one or more compression element, or both, is one or more elastomer, one or more spring, one or more rigid element, or a combination thereof.

4. The knee ankle foot orthosis of claim 1, wherein the adjustable energy storage mechanism provides a capability of changing the amount of the tension or compression force by one or more magnitudes of tension or compression force.

5. The knee ankle foot orthosis of claim 1, wherein the adjustable energy storage mechanism comprises at least one of a ratchet and pawl mechanism, a lever, a dial, a pin and slot, a pulley, a sprag clutch, a worm gear, or a friction pad.

6. The knee ankle foot orthosis of claim 1, wherein the adjustable energy storage mechanism is a first adjustable energy storage mechanism, and the ankle-foot orthosis component includes a second adjustable energy storage mechanism.

7. The knee ankle foot orthosis of claim 6, wherein the first adjustable energy storage mechanism is mechanically connected to the second adjustable energy storage mechanism.

8. The knee ankle foot orthosis of claim 6, wherein the first adjustable energy storage mechanism and the second adjustable energy storage mechanism are adjustable using a single adjustment component.

9. The knee ankle foot orthosis of claim 6, wherein the first adjustable energy storage mechanism comprises a first amount of stored energy and the second adjustable storage mechanism comprises a second amount of stored energy.

10. The knee ankle foot orthosis of claim 1, wherein the hinge is a polycentric hinge comprising one or more gears or cams of variable radii, and wherein the variable radii gears or cams generate a distraction force across or around a knee joint.

11. The knee ankle foot orthosis of claim 1, wherein the hinge is a distracting hinge comprising more than one pair of gears or cams, and wherein the more than one pair of gears or cams upon articulation generate a variable degree of distance between the upper and the lower portion at a different ranges of motion of the knee orthosis component.

12. The knee ankle foot orthosis of claim 1, wherein the upper portion and the lower portion of the knee orthosis component are further connected by a center cap, and wherein at least one of the upper portion, the lower portion, or the center cap, are curved to fully or partially conform to a wearer's joint or limb.

13. The knee ankle foot orthosis of claim 1, wherein at least one of an attachment mechanism or an attachment point between the knee orthosis component and the ankle-foot orthosis component is capable of withstanding at least 20 N of applied force.

14. The knee ankle foot orthosis of claim 1, further comprising:
one or more sensors, one or more processors, one or more motors, one or more controllers, or combinations thereof;
wherein the one or more sensors, the one or more processors, the one or more motors, the one or more controllers, or the combinations thereof, are capable of adjusting the adjustable energy storage mechanism.

15. The joint brace of claim 1, wherein the adjustable energy storage mechanism comprises a tensioning element, wherein the tensioning element is drawn over the hinge, wherein the tensioning element is integrated within at least one of the upper portion or the lower portion, and wherein the tensioning element is connected to a lace or wire drawn over the hinge.

16. The knee ankle foot orthosis of claim 1, wherein the adjustable energy storage mechanism is capable of changing the amount of the tension or compression force in a substantially continuous, gradual, incremental, or stepwise manner across a range or spectrum of magnitudes of tension or compression force.

17. The knee ankle foot orthosis of claim 1, wherein the knee orthosis component and the ankle-foot orthosis component are provided as separate components to be assembled or connected to one another.

18. The knee ankle foot orthosis of claim 1, wherein the knee orthosis component and the ankle-foot orthosis component are capable of being modified to fit a shape of a wearer's joint or limb, and wherein once fitted the knee orthosis component and the ankle-foot orthosis component can be fixed into a rigid or semi-rigid shape.

19. A knee ankle foot orthosis comprising:
a knee orthosis component;
an ankle-foot orthosis component; and
at least one attachable or permanently affixed connection mechanism connecting the knee orthosis component to the ankle-foot orthosis component;
wherein the ankle foot orthosis component is comprised of:
an upper portion and a lower portion, and
an adjustable energy storage mechanism directly or indirectly connecting the upper portion to the lower portion, wherein the adjustable energy storage mechanism generates a tension or compression force having an amount of tension or compression force, the tension or compression force being directed at least one of: around, across, and between, the upper portion and the lower portion; and
wherein the adjustable energy storage mechanism allows a wearer of the knee ankle foot orthosis to adjust the amount of the tension or compression force generated by the adjustable energy storage mechanism relative to at least one of the upper portion and the lower portion; and wherein the adjustable energy storage mechanism further allows the wearer to adjust the amount of the tension or compression force generated by the adjustable energy storage mechanism while the wearer is wearing the knee ankle foot orthosis.

20. The knee ankle foot orthosis of claim 19, wherein the adjustable energy storage mechanism comprises one or more tensioning element, one or more compression element, or a combination thereof.

21. The knee ankle foot orthosis of claim 20, wherein the one or more tensioning element, the one or more compression element, or both, comprise at least one of an elastomer, a spring, or a rigid element.

22. The knee ankle foot orthosis of claim 19, wherein the one or more adjustable energy storage mechanism provides a capability of changing the amount of the tension or compression force by one or more magnitudes of tension or compression force.

23. The knee ankle foot orthosis of claim 19, wherein the adjustable energy storage mechanism comprises at least one of a ratchet and pawl mechanism, a lever, a dial, a pin and slot, a pulley, a sprag clutch, a worm gear, or a friction pad.

24. The knee ankle foot orthosis of claim 19, wherein the adjustable energy storage mechanism generates the tension or compression force around one or more axes of a joint.

25. A hip knee ankle foot orthosis comprising:
a hip orthosis component;
a knee orthosis component;
an ankle-foot orthosis component; and
at least two attachable or permanently affixed connection mechanisms connecting the hip orthosis component to the knee orthosis component and the knee orthosis component to the ankle-foot orthosis component;
wherein the hip orthosis component is comprised of an upper portion and a lower portion directly or indirectly connected by an adjustable energy storage mechanism, wherein the adjustable energy storage mechanism generates a tension or compression force having an amount of tension or compression force, the tension or compression force being directed at least one of: around, across, and between, the upper portion and the lower portion; and
wherein the adjustable energy storage mechanism allows a wearer of the hip knee ankle foot orthosis to adjust the amount of the tension or compression force generated by the adjustable energy storage mechanism relative to at least one of the upper portion and the lower portion; and
wherein the adjustable energy storage mechanism further allows the wearer to adjust the amount of the tension or compression force generated by the adjustable energy storage mechanism while the wearer is wearing the hip knee ankle foot orthosis.

26. A hip knee ankle foot orthosis comprising:
a hip orthosis component;
a knee orthosis component;
an ankle-foot orthosis component; and
at least two attachable or permanently affixed connection mechanisms connecting the hip orthosis component to the knee orthosis component and the knee orthosis component to the ankle-foot orthosis component;
wherein at least one of the hip orthosis component, the knee orthosis component, or the ankle-foot orthosis component, comprise an adjustable energy storage mechanism;
wherein the adjustable energy storage mechanism generates a tension or compression force having an amount of tension or compression force, the tension or compression force being directed at least one of: around, across, and between, an upper portion and a lower portion of the hip orthosis component, the knee orthosis component, or the ankle-foot orthosis component, and wherein the adjustable energy storage mechanism directly or indirectly connects the upper portion to the lower portion; and
wherein the adjustable energy storage mechanism allows a wearer of the hip knee ankle foot orthosis to adjust the amount of the tension or compression force generated by the adjustable energy storage mechanism relative to at least one of the upper portion and the lower portion of the hip orthosis component, the knee orthosis component, or the ankle-foot orthosis component; and
wherein the adjustable energy storage mechanism further allows the wearer to adjust the amount of the tension or compression force generated by the adjustable energy storage mechanism while the wearer is wearing the hip knee ankle foot orthosis.

\* \* \* \* \*